United States Patent
Butlin et al.

(10) Patent No.: US 6,689,909 B1
(45) Date of Patent: Feb. 10, 2004

(54) SUBSTITUTED N-PHENYL 2-HYDROXY-2-METHYL-3,3,3-TRIFLUOROPROPANAMIDE DERIVATIVES WHICH ELEVATE PYRUVATE DEHYDROGENASE ACTIVITY

(75) Inventors: Roger John Butlin, Macclesfield Cheshire (GB); Janet Elizabeth Pease, Macclesfield Cheshire (GB); Michael Howard Block, Macclesfield Cheshire (GB); Thorsten Nowak, Macclesfield Cheshire (GB); Jeremy Nicholas Burrows, Macclesfield Cheshire (GB)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 10/069,994
(22) PCT Filed: Aug. 30, 2000
(86) PCT No.: PCT/GB00/03314
§ 371 (c)(1),
(2), (4) Date: Jun. 17, 2002
(87) PCT Pub. No.: WO01/17956
PCT Pub. Date: Mar. 15, 2001

(30) Foreign Application Priority Data

Sep. 4, 1999 (GB) .............................. 9920814
Mar. 21, 2000 (GB) .............................. 0006641

(51) Int. Cl.$^7$ ..................... C07C 233/05; C07C 231/02; A61K 31/16
(52) U.S. Cl. ................. 564/202; 514/227.5; 514/238.8; 514/239.5; 514/255; 514/328; 514/352; 514/603; 514/628; 544/58.1; 544/58.2; 544/159; 544/160; 544/358; 544/383; 546/219; 546/220; 546/309; 564/86
(58) Field of Search .................... 514/227.5, 255, 514/238.8, 239.5, 328, 352, 603, 628; 544/58.1, 58.2, 159, 160, 358, 383; 546/309, 219, 220; 564/86, 202.135

(56) References Cited

U.S. PATENT DOCUMENTS

| | | | |
|---|---|---|---|
| 4,537,618 A | 8/1985 | Schurter et al. | 544/321 |
| 5,248,693 A | 9/1993 | Gerspacher et al. | 548/511 |
| 5,486,515 A | 1/1996 | Brown et al. | |
| 5,510,386 A | 4/1996 | Empfield et al. | 546/89 |
| 6,369,273 B1 | 4/2002 | Butlin | |
| 6,498,275 B1 | 12/2002 | Butlin et al. | |

FOREIGN PATENT DOCUMENTS

| | | |
|---|---|---|
| CA | 1 228 355 | 10/1987 |
| EP | 0 002 309 | 6/1979 |
| EP | 0 002 892 | 7/1979 |
| EP | 0 040 932 | 12/1981 |
| EP | 0 079 191 | 5/1983 |
| EP | 0 096 002 | 12/1983 |
| EP | 0 100 172 | 2/1984 |
| EP | 0 253 500 | 1/1988 |
| EP | 0 253 503 | 1/1988 |
| EP | 0 524 781 A | 1/1993 |
| EP | 0 617 010 A | 9/1994 |
| EP | 0 625 511 | 11/1994 |
| EP | 0 625 516 | 11/1994 |
| GB | 2 278 054 | 11/1994 |
| WO | 93/10094 | 5/1993 |
| WO | 93/23358 | 5/1993 |
| WO | 94/26739 | 11/1994 |
| WO | 96/28151 | 9/1996 |
| WO | 97/38124 | 10/1997 |
| WO | 99/47508 | 9/1999 |
| WO | 99/62506 | 12/1999 |

OTHER PUBLICATIONS

Aicher et al., (R)–3,3,3–Trifluoro–2–hydroxy–2–methyl–propionamides Are Orally Active Inhibitors of Pyruvate Dehydrogenase Kinase, J. Med. Chem., 1999, vol. 42, pp. 2741–2746.

Aicher et al., "Secondary Amides of (R)–3,3,3–Trifluoro–2–hydroxy–2–methylpropionic Acid as Inhibitors of Pyruvate Dehydrogenase Kinase", J. Med. Chem., 2000, vol. 43, No. 2, pp. 236–249.

Bayles et al., "A Smiles Rearrangement Involving Non–Activated Aromatic Systems; the Facile Conversion of Phenols to Anilines", Synthesis, 1977, vol. 1. pp. 33–34.

Bayles et al.,, "The Smiles Rearrangement of 2–Aryloxy–2–methylpropanamides. Synthesis of N–Aryl–2–hydroxy–2–methyl–propanamides", Synthesis, 1977, vol. 1, pp. 31–33.

Bebernitz et al., "Anilides of (R)–Trifluoro–2–hydroxy–2–methylpropionic Acid as Inhibitors of Pyruvate Dehydrogenase Kinase", J. Med. Chem., 2000, vol. 43, No. 11, pp. 2257–2266.

(List continued on next page.)

Primary Examiner—Shailendra Kumar
(74) Attorney, Agent, or Firm—Morgan, Lewis & Bockius LLP

(57) ABSTRACT

A compound of formula (I) wherein: n is 1 or 2; $R^1$ is chloro, fluoro, bromo, methyl or methoxy; $R^2$ is as defined within; $R^3$ is as defined within; and $R^4$ is hydrogen or fluoro; or a pharmaceutically acceptable salt or an in vivo hydrolysable ester thereof is described. The use of compounds of formula (I) in the production of an elevation of PDH activity in a warm-blooded animal such as a human being are also described. Pharmaceutical compositions, methods and processes for preparation of compounds of formula (I) are detailed.

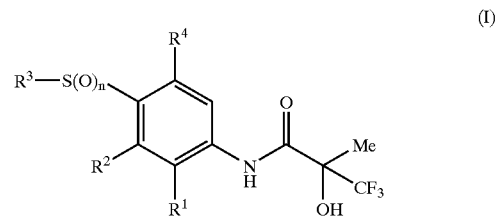

(I)

13 Claims, No Drawings

OTHER PUBLICATIONS

Empfield et al., "4–sulfonamidoanilide Tertiary Carbinols: A Novel Series Of Potassium Channel Openers", Bioorg Med. Chem. Letters, 1997, vol. 7, No. 7, pp. 775–778, XP004136128 see table I, compounds e, f.

Fenwick, "The Synthesis of 2,2–Bis(Trifluoromethyl)Benzopyran Derivatives: A New Route to an Import Class of Postassium Channel Activators", Tetrahedron Letters, vol. 34, No. 11, 1993, pp. 1993.

Furr et al., "A Novel Non–Steroidal, Peripherally Selective Antiandrogen", J. Endrocrinol., 1987, vol. 113 (3), R7–R9.

Glen et al., Structure–Activity Relationships among Non–steriodal Antiandrogens, Third SCI–RSC Medicinal Chemistry Symposium, 1986, vol. 55, pp. 345–361.

Morris et al., "Non–Steroidal Antiandrogens. Design of Novel Compounds Based on an Infrared Study of the Dominant Conformationand Hydrogen–Bonding Properties of a Series of Anilide Antiandrogens", J. Med. Chem. 1991, vol. 34, pp. 447–455.

Russell, "Crystal Receptor Models In Medicinal Chemistry: Application To The Generation of Highly Potent Potassium Channel Openers", Bioorg. Med. Chem. Lett. 1996, vol. 6 (7), pp. 913–918.

Tenthorey et al.; "New Antiarrhythmic Agents. 3. Primary β–Amino Anilides", J. Med. Chem. 1979, vol. 22 (10), pp. 1182–1186.

Trivedi et al., "K–Channel Opening Activity of ZD6169 and Its Analogs: Effect on $^{86}$Rb Efflux and $^{3}$H–1075 Binding in Bladder Smooth Muscle", Pharmacology, 1995, vol. 50 (6), pp. 388–397.

Tucker et al., "Nonsteroidal Antiandrogens. Synthesis and Structure–Activity Relationships of 3–Substituted Derivatives of 2–Hydroxypropionanilides", J. Med. Chem., 1988, vol. 31, pp. 954–959.

Tucker et al., "Resolution of the Nonsteriodal Anti-androgen 4'–Cyano–3–[(4–fluorophenyl)sulfonyl]–2–hydroxy–2–methyl–3'–(trifluoromethyl)–propionanilide and the Determination of the Absolute Configuration of the Active Enantiomer", J. Med. Chem. 1988. vol. 31 (4), pp. 885–887.

Wakeling et al., "Receptor Binding And Biological Activity Of Steriodal and Nonsteriodal Antiandrogens", J. Steriod Biochem., 1981, vol. 15, pp. 355–359.

Ohmacht et al., "N–Aryl–3,3,3–trifluoro–2–hydroxy–2–methyl propanamides: KATP pastassium channel openers. Modifications on the western region", Journal of Medicinal Chemistry, vol. 32, No. 23, Nov. 1996, XP002110510.

SUBSTITUTED N-PHENYL 2-HYDROXY-2-METHYL-3,3,3-TRIFLUOROPROPANAMIDE DERIVATIVES WHICH ELEVATE PYRUVATE DEHYDROGENASE ACTIVITY

This application is a 371 of PCT/GB00/03314, filed Aug. 30, 2000.

The present invention relates to compounds which elevate pyruvate dehydrogenase (PDH) activity, processes for their preparation, pharmaceutical compositions containing them as active ingredient, methods for the treatment of disease states associated with reduced PDH activity, to their use as medicaments and to their use in the manufacture of medicaments for use in the elevation of PDH activity in warm-blooded animals such as humans, in particular the treatment of diabetes mellitus, peripheral vascular disease and myocardial ischaemia in warm-blooded animals such as humans, more particularly to their use in the manufacture of medicaments for use in the treatment of diabetes mellitus in warm-blooded animals such as humans.

Within tissues adenosine triphosphate (ATP) provides the energy for synthesis of complex molecules and, in muscle, for contraction. ATP is generated from the breakdown of energy-rich substrates such as glucose or long chain free fatty acids. In oxidative tissues such as muscle the majority of the ATP is generated from acetyl CoA which enters the citric acid cycle, thus the supply of acetyl CoA is a critical determinant of ATP production in oxidative tissues. Acetyl CoA is produced either by β-oxidation of fatty acids or as a result of glucose metabolism by the glycolytic pathway. The key regulatory enzyme in controlling the rate of acetyl CoA formation from glucose is PDH which catalyses the oxidation of pyruvate to acetyl CoA and carbon dioxide with concomitant reduction of nicotinamide adenine dinucleotide (NAD) to NADH.

In disease states such as both non-insulin dependent (NIDDM) and insulin-dependent diabetes mellitus (IDDM), oxidation of lipids is increased with a concomitant reduction in utilisation of glucose, which contributes to the hyperglycaemia. Reduced glucose utilisation in both IDDM and NIDDM is associated with a reduction in PDH activity. In addition, a further consequence of reduced PDH activity may be that an increase in pyruvate concentration results in increased availability of lactate as a substrate for hepatic gluconeogenesis. It is reasonable to expect that increasing the activity of PDH could increase the rate of glucose oxidation and hence overall glucose utilisation, in addition to reducing hepatic glucose output. Another factor contributing to diabetes mellitus is impaired insulin secretion, which has been shown to be associated with reduced PDH activity in pancreatic β-cells (in a rodent genetic model of diabetes mellitus Zhou et al. (1996) Diabetes 45: 580–586).

Oxidation of glucose is capable of yielding more molecules of ATP per mole of oxygen than is oxidation of fatty acids. In conditions where energy demand may exceed energy supply, such as myocardial ischaemia, intermittent claudication, cerebral ischaemia and reperfusion, (Zaidan et al., 1998; J. Neurochem. 70: 233–241), shifting the balance of substrate utilisation in favour of glucose metabolism by elevating PDH activity may be expected to improve the ability to maintain ATP levels and hence function.

An agent which is capable of elevating PDH activity may also be expected to be of benefit in treating conditions where an excess of circulating lactic acid is manifest such as in certain cases of sepsis.

The agent dichloroacetic acid (DCA) which increases the activity of PDH after acute administration in animals, (Vary et al., 1988; Circ. Shock, 24: 3–18), has been shown to have the predicted effects in reducing glycaemia, (Stacpoole et al., 1978; N. Engl. J. Med. 298: 526–530), and as a therapy for myocardial ischaemia (Bersin and Stacpoole 1997; American Heart Journal, 134: 841–855) and lactic acidaemia, (Stacpoole et al., 1983; N. Engl. J. Med. 309: 390–396).

PDH is an intramitochondrial multienzyme complex consisting of multiple copies of several subunits including three enzyme activities E1, E2 and E3, required for the completion of the conversion of pyruvate to acetyl CoA (Patel and Roche 1990; FASEB J., 4: 3224–3233). E1 catalyses the non-reversible removal of $CO_2$ from pyruvate; E2 forms acetyl CoA and E3 reduces NAD to NADH. Two additional enzyme activities are associated with the complex: a specific kinase which is capable of phosphorylating E1 at three serine residues and a loosely-associated specific phosphatase which reverses the phosphorylation. Phosphorylation of a single one of the three serine residues renders the E1 inactive. The proportion of the PDH in its active (dephosphorylated) state is determined by a balance between the activity of the kinase and phosphatase. The activity of the kinase may be regulated in vivo by the relative concentrations of metabolic substrates such as NAD/NADH, CoA/acetylCoA and adenine diphosphate (ADP)/ATP as well as by the availability of pyruvate itself.

European Patent Publication Nos. 617010 and 524781 describes compounds which are capable of relaxing bladder smooth muscle and which may be used in the treatment of urge incontinence. We have found that the compounds of the present invention are very good at elevating PDH activity, a property nowhere disclosed in EP 0617010 and EP 524781.

The present invention is based on the surprising discovery that certain compounds elevate PDH activity, a property of value in the treatment of disease states associated with disorders of glucose utilisation such as diabetes mellitus, obesity, (Curto et al., 1997; Int. J. Obes. 21: 1137–1142), and lactic acidaemia. Additionally the compounds may be expected to have utility in diseases where supply of energy-rich substrates to tissues is limiting such as peripheral vascular disease, (including intermittent claudication), cardiac failure and certain cardiac myopathies, muscle weakness, hyperlipidaemias and atherosclerosis (Stacpoole et al., 1978; N. Engl. J. Med. 298: 526–530). A compound that activates PDH may also be useful in treating Alzheimer's disease (AD) (J Neural Transm (1998) 105, 855–870).

Accordingly the present invention provides a compound of formula (I):

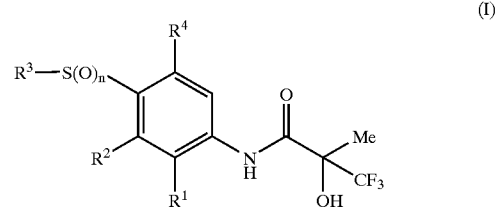

(I)

wherein:

n is 1 or 2;

$R^1$ is chloro, fluoro, bromo, methyl or methoxy;

$R^2$ is selected from one of the following three groups:
  i) halo, nitro, hydroxy, amino or cyano;
  ii) —$X^1$—$R^5$ wherein $X^1$ is a direct bond, —O—, —S—, —SO—, —$SO_2$—, —$NR^6$—, —CO—, —$CONR^6$—, —$NR^6CO$—, —$NR^6SO_2$— or NR⁶CONR⁷—; wherein R⁶ and R⁷ are independently hydrogen or $C_{1-4}$alkyl optionally substituted with one or more A; and R⁵ is selected from $C_{1-6}$alkyl optionally substituted with one or more A, $C_{3-7}$cycloalkyl optionally substituted with one or more A, $C_{3-7}$cycloalkyl$C_{1-6}$alkyl optionally substituted with one or more A, $C_{2-6}$alkenyl optionally substituted with one or more A, $C_{2-6}$alkynyl optionally substituted with one or more A, phenyl optionally substituted with one or more D, phenyl$C_{1-6}$alkyl optionally substituted with one or more D, heteroaryl ring optionally substituted on a ring carbon by one or more D or (heteroaryl ring)$C_{1-6}$alkyl optionally substituted on a ring carbon with one or more D; wherein said heteroaryl ring is a carbon linked 6-membered ring containing 1–2 nitrogen atoms or a carbon linked 5-membered ring containing 1–3 heteroatoms selected independently from O, N and S; and wherein if said 5-membered heteroaryl ring contains an —NH— moiety that nitrogen may be optionally substituted with a group selected from G;
iii) a nitrogen-linked 4–8 membered heterocyclic group optionally substituted on a ring carbon by one or more D and wherein if said heterocyclic group contains an —NH— moiety that nitrogen may be optionally substituted with a group selected from G;

R³ is $C_{1-6}$alkyl optionally substituted with one or more A, $C_{3-7}$cycloalkyl optionally substituted with one or more A, phenyl optionally substituted with one or more D, a carbon-linked 6-membered heteroaryl ring containing 1–2 nitrogen atoms optionally substituted on a ring carbon by one or more D, or a carbon linked 5-membered heteroaryl ring containing 1–3 heteroatoms selected independently from O, N and S optionally substituted on a ring carbon by one or more D and wherein if said 5-membered heteroaryl ring contains an —NH— moiety that nitrogen may be optionally substituted with a group selected from G;

A is selected from hydroxy, amino, halo, carboxy, N—($C_{1-4}$alkyl)amino, N,N-di-($C_{1-4}$alkyl)amino, carbamoyl and $C_{1-6}$alkoxy;

D is selected from:
i) —$X^a$—$R^c$ wherein $X^a$ is a direct bond, —O—, —S—, —SO—, —SO₂—, —CO—, —$NR^d$SO₂—, —$NR^d$CO—, —$NR^d$CONR^e$—, —$NR^d$— or —CONR$^d$—; wherein $R^d$ and $R^e$ are independently hydrogen or $C_{1-4}$alkyl optionally substituted with one or more hydroxy or $C_{1-4}$alkoxy; and $R^c$ is selected from hydrogen or $C_{1-6}$alkyl optionally substituted with one or more hydroxy or $C_{1-4}$alkoxy;
ii) a 4–8 membered Het which is optionally substituted on a ring carbon with one or more groups selected from hydroxy, halo, $C_{1-4}$alkoxy, $C_{1-4}$alkyl or cyano and wherein if said 4–8 membered Het contains an —NH— moiety that nitrogen may be optionally substituted with a group selected from G;
iii) —$X^a$—$C_{1-6}$alkyl-$X^b$—$W^c$ wherein $X^a$ and $R^c$ are as defined hereinbefore and $X^b$ is —S—, —SO— or —SO₂—;
iv) cyano or halo; and
v) —$X^c$—$R^f$ wherein $X^c$ is —C(O)— or —SO₂— and $R^f$ is a nitrogen-linked 4–8 membered heterocyclic group optionally substituted on a ring carbon by one or more groups selected from hydroxy, halo, $C_{1-4}$alkoxy, $C_{1-4}$alkyl or cyano and wherein if said heterocyclic group contains an —NH— moiety that nitrogen may be optionally substituted with a group selected from G;

G is selected from $C_{1-6}$alkyl optionally substituted with one or more A, $C_{1-6}$alkanoyl optionally substituted with one or more A, $C_{1-4}$alkylsulphonyl optionally substituted with one or more A, $C_3$alkoxycarbonyl optionally substituted with one or more A, carbamoyl, N—($C_{1-6}$alkyl)carbamoyl optionally substituted with one or more A, N—($C_{1-6}$alkyl)₂carbamoyl optionally substituted with one or more A and benzoyl optionally substituted with one or more A; and R⁴ is hydrogen or fluoro;

or a pharmaceutically acceptable salt or an in vivo hydrolysable ester thereof.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, $C_{2-4}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. The term "halo" refers to fluoro, chloro, bromo and iodo.

Suitable values for "a carbon-linked 6-membered heteroaryl ring containing 1–2 nitrogen atoms" include pyridyl, pyrimidyl, pyrazinyl and pyridazinyl. Preferably "a carbon-linked 6-membered heteroaryl ring containing 1–2 nitrogen atoms" is pyridyl. In another aspect of the invention preferably "a carbon-linked 6-membered heteroaryl ring containing 1–2 nitrogen atoms" is pyridazinyl.

Suitable values for "a carbon-linked 5-membered heteroaryl ring containing 1–3 heteroatoms" include pyrrolyl, furyl, thienyl, pyrazolyl, oxazolyl, oxadiazolyl, imidazolyl and triazolyl.

A "nitrogen-linked 4–8 membered heterocyclic group" is a saturated, partially saturated or unsaturated, monocyclic ring containing 4–8 atoms of which at least one is a nitrogen atom with optionally 1–3 further heteroatoms selected independently from O, N and S wherein a —CH₂— group can optionally be replaced by a —C(O)— and a ring nitrogen and/or sulphur atom may be optionally oxidised to form the N-oxide and or the S-oxides. It will be appreciated that in forming this nitrogen link, the nitrogen atom is not quaternised, i.e. a neutral compound is formed. Suitable values for "nitrogen-linked 4–8 membered heterocyclic group" include morpholino, piperidyl, piperazinyl, pyrrolidinyl, thiomorpholino, pyrrolinyl, homopiperazinyl, pyrrolyl, pyrazolyl, pyrazolinyl, imidazolyl, imidazolinyl, imidazolidinyl, pyrazolidinyl and triazolyl. Further suitable values for "nitrogen-linked 4–8 membered heterocyclic group" include azetidinyl, morpholino, piperidyl, piperazinyl, pyrrolidinyl, thiomorpholino, pyrrolinyl, homopiperazinyl, pyrrolyl, pyrazolyl, pyrazolinyl, imidazolyl, imidazolinyl, imidazolidinyl, pyrazolidinyl and triazolyl. Preferably a "nitrogen-linked 4–8 membered heterocyclic group" is morpholino, piperidyl, piperazinyl, pyrrolidinyl, thiomorpholino, pyrrolinyl or homopiperazinyl. More preferably a "nitrogen-linked 4–8 membered heterocyclic group" is azetidinyl, morpholino, piperidyl, piperazinyl, pyrrolidinyl, thiomorpholino, pyrrolinyl or homopiperazinyl. Additional suitable values for "nitrogen-linked 4–8 membered heterocyclic group" include azetidinyl, morpholino, piperidyl, piperazinyl, pyrrolidinyl, thiomorpholino, 1-oxothiomorpholino, 1,1-dioxothiomorpholino, pyrrolinyl, homopiperazinyl, pyrrolyl, pyrazolyl, pyrazolinyl, inidazolyl, imidazolinyl, imidazolidinyl, pyrazolidinyl and triazolyl. Preferably a "nitrogen-linked 4–8 membered heterocyclic group" is morpholino, 1-oxothiomorpholino, 1,1-dioxothiomorpholino, piperidyl, piperazinyl, pyrrolidinyl, thiomorpholino, pyrrolinyl or homopiperazinyl. More preferably a "nitrogen-linked 4–8 membered heterocyclic group" is azetidinyl, morpholino, piperidyl, piperazinyl, pyrrolidinyl, thiomorpholino, 1-oxothiomorpholino, 1,1-dioxothiomorpholino, pyrrolinyl or homopiperazinyl. Particularly $R^f$ as a "nitrogen-linked 4–8 membered heterocyclic group" is azetidinyl, morpholino or pyrrolidinyl. Particularly when $R^2$ is a "nitrogen-linked 4–8 membered heterocyclic group" it is thiomorpholino. In another aspect of the invention, particularly when $R^2$ is a "nitrogen-linked 4–8 membered heterocyclic group" it is thiomorpholino, piperazinyl, 1-oxothiomorpholino, 1,1-dioxothiomorpholino or morpholino.

A "nitrogen-linked 4–6 membered heterocyclic group" is a saturated, partially saturated or unsaturated, monocyclic ring containing 4–6 atoms of which at least one is a nitrogen atom with optionally 1–3 further heteroatoms selected independently from O, N and S wherein a —CH$_2$— group can optionally be replaced by a —C(O)— and a ring nitrogen and/or sulphur atom may be optionally oxidised to form the N-oxide and or the S-oxides. It will be appreciated that in forming this nitrogen link, the nitrogen atom is not quaternised, i.e. a neutral compound is formed. Suitable values for a "nitrogen-linked 4–6 membered heterocyclic group" include azetidinyl, morpholino, piperidyl, piperazinyl, pyrrolidinyl, thiomorpholino, pyrrolinyl, pyrrolyl, pyrazolyl, pyrazolinyl, imidazolyl, imidazolinyl, imidazolidinyl, pyrazolidinyl and triazolyl. Preferably a "nitrogen-linked 4–6 membered heterocyclic group" is azetidinyl, morpholino or pyrrolidinyl.

A "nitrogen-linked 5 or 6 membered heterocyclic group" is a saturated, partially saturated or unsaturated, monocyclic ring containing 5 or 6 atoms of which at least one is a nitrogen atom with optionally 1–3 further heteroatoms selected independently from O, N and S wherein a —CH$_2$— group can optionally be replaced by a —C(O)— and a ring nitrogen and/or sulphur atom may be optionally oxidised to form the N-oxide and or the S-oxides. It will be appreciated that in forming this nitrogen link, the nitrogen atom is not quaternised, i.e. a neutral compound is formed. Suitable values for a "nitrogen-linked 5 or 6 membered heterocyclic group" include morpholino, piperidyl, piperazinyl, pyrrolidinyl, thiomorpholino, pyrrolinyl, pyrrolyl, pyrazolyl, pyrazolinyl, imidazolyl, imidazolinyl, imidazolidinyl, pyrazolidinyl and triazolyl. Preferably a "nitrogen-linked 5 or 6 membered heterocyclic group" is morpholino, piperidyl, piperazinyl, pyrrolidinyl, thiomorpholino or pyrrolinyl.

A "nitrogen-linked 6 membered heterocyclic group" is a saturated, partially saturated or unsaturated, monocyclic ring containing 6 atoms of which at least one is nitrogen atom with optionally 1–3 further heteroatoms selected independently from O, N and S wherein a —CH$_2$— group can optionally be replaced by a —C(O)— and a ring nitrogen and/or sulphur atom may be optionally oxidised to form the N-oxide and or the S-oxides. It will be appreciated that in forming this nitrogen link, the nitrogen atom is not quaternised, i.e. a neutral compound is formed. Suitable values for a "nitrogen-linked 6 membered heterocyclic group" include morpholino, piperidyl, piperazinyl, thiomorpholino.

A "4–8 membered Het" is a saturated, partially saturated or unsaturated monocyclic ring containing 48 atoms including 1–4 heteroatoms selected independently from O, N and S, which may be carbon or nitrogen linked, wherein a —CH$_2$— group can optionally be replaced by a —C(O)— and a ring nitrogen and/or sulphur atom may be optionally oxidised to form the N-oxide and or the S-oxides. Suitable values for "4–8 membered Het" are morpholino, piperidyl, pyridyl, pyranyl, pyrrolyl, isothiazolyl, thienyl, thiadiazolyl, piperazinyl, thiazolidinyl, pyrrolidinyl, thiomorpholino, pyrrolinyl, homopiperazinyl, tetrahydropyranyl, imidazolyl, pyrimidyl, pyrazinyl, pyridazinyl, isoxazolyl, 4-pyridone, 2-pyrrolidone, 4-thiazolidone, pyridine-N-oxide and quinoline-N-oxide.

A "5 or 6 membered Het" is a saturated, partially saturated or unsaturated monocyclic ring containing 4–8 atoms including 1–4 heteroatoms selected independently from O, N and S, which may be carbon or nitrogen linked, wherein a —CH$_2$— group can optionally be replaced by a —C(O)— and a ring nitrogen and/or sulphur atom may be optionally oxidised to form the N-oxide and or the S-oxides. Suitable values for "5 or 6 membered Het" are morpholino, piperidyl, pyridyl, pyranyl, pyrrolyl, isothiazolyl, thienyl, thiadiazolyl, piperazinyl, thiazolidinyl, pyrrolidinyl, thiomorpholino, pyrrolinyl, tetrahydropyranyl, imidazolyl, pyrimidyl, pyrazinyl, pyridazinyl, isoxazolyl, 4-pyridone, 2-pyrrolidone, 4-thiazolidone, pyridine-N-oxide and quinoline-N-oxide.

Examples of "$C_{1-6}$alkoxycarbonyl" include methoxycarbonyl, ethoxycarbonyl, n- and t-butoxycarbonyl. Examples of "$C_{1-6}$alkoxy" include $C_{1-4}$alkoxy, methoxy, ethoxy and propoxy. Examples of "$C_{1-14}$alkylsulphinyl" include methylsulphinyl and ethylsulphinyl. Examples of "$C_{1-6}$alkylsulphonyl" include $C_{1-4}$alkylsulphonyl, mesyl and ethylsulphonyl. Examples of "$C_{1-6}$alkanoyl" include $C_{1-4}$alkanoyl, propionyl and acetyl. Examples of "$C_{3-7}$cycloalkyl" are cyclopropyl and cyclohexyl. Examples of "$C_{2-6}$alkenyl" are vinyl, allyl and 1-propenyl. Examples of "$C_{2-6}$alkynyl" are ethynyl, 1-propynyl and 2-propynyl. Examples of "N—($C_{1-6}$alkyl)carbamoyl" are methylaminocarbonyl and ethylaminocarbonyl. Examples of "N—($C_{1-6}$ alkyl)$_2$carbamoyl" are dimethylaminocarbonyl and methylethylaminocarbonyl. Examples of "N—($C_{1-4}$alkyl) amino" include methylamino and ethylamino. Examples of "N—($C_{1-4}$alkyl)$_2$amino" include di-N-methylamino, di-(N-ethyl)amino and N-ethyl-N-methylamino. Examples of "phenyl$C_{1-4}$alkyl" include phenyl$C_{1-4}$alkyl, benzyl and phenethyl. Examples of "$C_{3-7}$cycloalkyl$C_{1-6}$alkyl" include cyclopropylmethyl, cyclopentylethyl and 2-cyclohexylpropyl. Examples of "(heteroaryl ring)$C_{1-6}$alkyl" include pyridylmethyl, pyrazinylethyl and imidazolylpropyl.

According to a further aspect of the present invention there is provided a compound of formula (I) (as depicted above) wherein:

n is 1 or 2;

$R^1$ is chloro, fluoro, bromo, methyl or methoxy;

$R^2$ is selected from one of the following three groups:
  i) halo, nitro, hydroxy, amino or cyano;
  ii) —$X^1$—$R^5$ wherein $X^1$ is a direct bond, —O—, —S—, —SO—, —SO$^2$—, —NR$^6$—, —CO—, —CONR$^6$—, —NR$^6$CO—, —NR$^6$SO$_2$— or NR$^6$CONR$^7$—; wherein $R^6$ and $R^7$ are independently hydrogen or $C_{1-4}$alkyl optionally substituted with one or more A; and $R^5$ is selected from $C_{1-4}$alkyl optionally substituted with one or more A, $C_{3-7}$cycloalkyl optionally substituted with one or more A, $C_{2-6}$alkenyl optionally substituted with one or more A, $C_{2-6}$alkynyl optionally substituted with one or more A, phenyl optionally substituted with one or more D, a carbon linked 6-membered heteroaryl ring containing 1–2 nitrogen atoms optionally substituted on a ring carbon by one or more D or a carbon linked 5-membered heteroaryl ring containing 1–3 heteroatoms selected independently from O, N and S optionally substituted on a ring carbon by one or more D and wherein if said 5-membered heteroaryl ring contains an —NH— moiety that nitrogen may be optionally substituted with a group selected from G;

iii) a nitrogen-linked 4–8 membered heterocyclic group optionally substituted on a ring carbon by one or more D and wherein if said heterocyclic group contains an —NH— moiety that nitrogen may be optionally substituted with a group selected from G;

$R^3$ is $C_{1-6}$alkyl optionally substituted with one or more A, $C_{3-7}$cycloalkyl optionally substituted with one or more A, phenyl optionally substituted with one or more D, a carbon-linked 6-membered heteroaryl ring containing 1–2 nitrogen atoms optionally substituted on a ring carbon by one or more D, or a carbon linked 5-membered heteroaryl ring containing 1–3 heteroatoms selected independently from O, N and S optionally substituted on a ring carbon by one or more D and wherein if said 5-membered heteroaryl ring contains an —NH— moiety that nitrogen may be optionally substituted with a group selected from G;

A is selected from hydroxy, amino, halo, carboxy and $C_{1-6}$alkoxy;

D is selected from:
i) —$X^a$—$R^c$ wherein $X^a$ is a direct bond, —O—, —S—, —SO—, —SO$_2$—, —CO—, —NR$^d$SO$_2$—, —NR$^d$CO—, —NR$^d$CONR$^e$—, —NR$^d$— or —CONR$^d$—; wherein $R^d$ and $R^e$ are independently hydrogen or $C_{1-4}$alkyl optionally substituted with one or more hydroxy or $C_{1-4}$alkoxy; and $R^c$ is selected from hydrogen or $C_{1-4}$alkyl optionally substituted with one or more hydroxy or $C_{1-4}$alkoxy;
ii) a 4–8 membered Het which is optionally substituted on a ring carbon with one or more groups selected from hydroxy, halo, $C_{1-4}$alkoxy, $C_{1-4}$alkyl or cyano and wherein if said 4–8 membered Het contains an —NH— moiety that nitrogen may be optionally substituted with a group selected from G;
iii) —$X^a$—$C_{1-6}$alkyl-$X^b$—$R^c$ wherein $X^a$ and $R^c$ are as defined hereinbefore and $X^b$ is —S—, —SO— or —SO$_2$—; and
iv) cyano or halo;

G is selected from $C_{1-6}$alkyl optionally substituted with one or more A, $C_{1-6}$alkanoyl optionally substituted with one or more A, $C_{1-6}$alkylsulphonyl optionally substituted with one or more A, $C_{1-6}$alkoxycarbonyl optionally substituted with one or more A, carbamoyl, N—($C_{1-6}$alkyl)carbamoyl optionally substituted with one or more A, N—($C_{1-6}$alkyl)$_2$carbamoyl optionally substituted with one or more A and benzoyl optionally substituted with one or more A; and $R^4$ is hydrogen or fluoro;

or a pharmaceutically acceptable salt or an in vivo hydrolysable ester thereof.

Accordingly to an additional aspect of the present invention there is provided a compound of formula (I) (as depicted above) wherein:

n is 1 or 2;
$R^1$ is chloro, fluoro, bromo, methyl or methoxy;
$R^2$ is selected from one of the following three groups:
i) halo, nitro, hydroxy, amino or cyano;

ii) —$X^1$—$R^5$ wherein $X^1$ is a direct bond, —O—, —S—, —SO—, —SO$_2$—, NR$^6$—, —CO—, —CONR$^6$—, —NR$^6$CO—, —NR$^6$SO$_2$— or NR$^6$CONR$^7$—; wherein $R^6$ and $R^7$ are independently hydrogen or $C_{1-4}$alkyl optionally substituted with one or more A; and $R^5$ is selected from $C_{1-4}$alkyl optionally substituted with one or more A, $C_{3-7}$cycloalkyl optionally substituted with one or more A, $C_{2-6}$alkenyl optionally substituted with one or more A, $C_{2-4}$alkynyl optionally substituted with one or more A, phenyl optionally substituted with one or more D, a carbon linked 6-membered heteroaryl ring containing 1–2 nitrogen atoms optionally substituted on a ring carbon by one or more D or a carbon linked 5-membered heteroaryl ring containing 1–3 heteroatoms selected independently from O, N and S optionally substituted on a ring carbon by one or more D and wherein if said 5-membered heteroaryl ring contains an —NH— moiety that nitrogen may be optionally substituted with a group selected from G;

iii) a nitrogen-linked 4–8 membered heterocyclic group optionally substituted on a ring carbon by one or more D and wherein if said heterocyclic group contains an —NH— moiety that nitrogen may be optionally substituted with a group selected from G;

$R^3$ is $C_{1-6}$alkyl optionally substituted with one or more A, $C_{3-7}$cycloalkyl optionally substituted with one or more A, phenyl optionally substituted with one or more D, a carbon-linked 6-membered heteroaryl ring containing 1–2 nitrogen atoms optionally substituted on a ring carbon by one or more D, or a carbon linked 5-membered heteroaryl ring containing 1–3 heteroatoms selected independently from O, N and S optionally substituted on a ring carbon by one or more D and wherein if said 5-membered heteroaryl ring contains an —NH— moiety that nitrogen may be optionally substituted with a group selected from G;

A is selected from hydroxy, amino, halo, carboxy, N—($C_{1-4}$alkyl)amino, N,N-di-($C_{1-4}$alkyl)amino and $C_{1-6}$alkoxy;

D is selected from:
i) —$X^a$—$R^c$ wherein $X^a$ is a direct bond, —O—, —S—, —SO—, —SO$_2$—, —CO—, —NR$^d$SO$_2$—, NR$^d$CO—, —NR$^d$CONR$^e$—, —NR$^d$— or —CONR$^d$—; wherein $R^d$ and $R^e$ are independently hydrogen or $C_{1-4}$alkyl optionally substituted with one or more hydroxy or $C_{1-4}$alkoxy; and $R^c$ is selected from hydrogen or $C_{1-6}$alkyl optionally substituted with one or more hydroxy or $C_{1-4}$alkoxy;
ii) a 4–8 membered Het which is optionally substituted on a ring carbon with one or more groups selected from hydroxy, halo, $C_{1-4}$alkoxy, $C_{1-4}$alkyl or cyano and wherein if said 4–8 membered Het contains an —NH— moiety that nitrogen may be optionally substituted with a group selected from G;
iii) —$X^a$—$C_{1-6}$alkyl-$X^b$—$R^c$ wherein $X^a$ and $R^c$ are as defined hereinbefore and $X^b$ is —S—, —SO— or —SO$_2$—;
iv) cyano or halo; and
v) —$X^c$—$R^f$ wherein $X^c$ is —C(O)— or —SO$_2$— and $R^f$ is a nitrogen-linked 4–8 membered heterocyclic group optionally substituted on a ring carbon by one or more groups selected from hydroxy, halo, $C_{1-4}$alkoxy, $C_{1-4}$alkyl or cyano and wherein if said heterocyclic group contains an —NH— moiety that nitrogen may be optionally substituted with a group selected from G;

G is selected from $C_{1-6}$alkyl optionally substituted with one or more A, $C_{1-6}$alkanoyl optionally substituted with one or more A, $C_{1-6}$alkylsulphonyl optionally substituted with one or more A, $C_{1-6}$alkoxycarbonyl optionally substituted with one or more A, carbamoyl, N—($C_{1-6}$alkyl)carbamoyl optionally substituted with one or more A, N—($C_{1-6}$alkyl)$_2$Carbamoyl optionally substituted with one or more A and benzoyl optionally substituted with one or more A; and $R^4$ is hydrogen or fluoro;

or a pharmaceutically acceptable salt or an in vivo hydrolysable ester thereof.

Preferred values of $R^1$, $R^2$, $R^3$ and $R^4$ are as follows. Such values may be used where appropriate with any of the definitions, claims or embodiments defined hereinbefore or hereinafter.

In one aspect of the invention preferably n is 1.
In another aspect of the invention preferably n is 2.
Preferably $R^1$ is chloro, fluoro or bromo.
More preferably $R^1$ is chloro or fluoro.
Particularly $R^1$ is chloro.
In another aspect of the invention, preferably $R^1$ is methyl, chloro, fluoro or bromo.
In another aspect of the invention, more preferably $R^1$ is methyl, chloro or fluoro.
In another aspect of the invention, particularly $R^1$ is methyl or chloro.

Where $R^2$ is Selected From Group i):
Preferably group i) is halo or hydroxy.
More preferably group i) is halo.
Particularly group i) is chloro or fluoro.
More particularly group i) is chloro.

In Another Aspect of the Invention, Where $R^2$ is Selected From Group i):
Preferably group i) is nitro, halo, amino or hydroxy.
More preferably group i) is nitro, amino or halo.
Particularly group i) is nitro, bromo, iodo, amino, chloro or fluoro.

Where $R^2$ is Selected From Group ii):
Preferably in group ii) $X^1$ is —S—, —SO—, —SO$_2$—, NR$^6$ or —NR$^6$CO—; preferably $R^6$ is hydrogen; and preferably $R^5$ is selected from $C_{1-6}$alkyl optionally substituted with one or more A, phenyl optionally substituted with one or more D or a carbon linked 6-membered heteroaryl ring containing 1–2 nitrogen atoms optionally substituted on a ring carbon by one or more D.

More preferably in group ii) $X^1$ is —S—, —SO—, —SO$_2$— or —NR$^6$CO—; more preferably $R^6$ is hydrogen; and more preferably $R^5$ is selected from $C_{1-4}$alkyl optionally substituted with one or more A, phenyl optionally substituted with one or more D or a carbon linked pyridyl optionally substituted on a ring carbon by one or more D.

Particularly in group ii) $X^1$ is —S— or —NR$^6$CO—; particularly $R^6$ is hydrogen; and particularly $R^5$ is selected from methyl optionally substituted with one or more A, ethyl optionally substituted with one or more A, phenyl optionally substituted with one or more D or a carbon linked pyridyl optionally substituted on a ring carbon by one or more D. In another aspect of the invention, where $R^2$ is selected from group ii):

Preferably in group ii) $X^1$ is —S—, —SO—, —SO$_2$—, —NR$^6$— or —NR$^6$CO—; preferably $R^6$ is hydrogen; and preferably $R^5$ is selected from $C_{1-6}$alkyl optionally substituted with one or more A or phenyl optionally substituted with one or more D.

More preferably in group ii) $X^1$ is —S—, —SO—, —SO$_2$— or —NR$^6$CO—; more preferably $R^6$ is hydrogen; and more preferably $R^5$ is selected from $C_{1-4}$alkyl optionally substituted with one or more A or phenyl optionally substituted with one or more D.

Particularly in group ii) $X^1$ is —S— or —NR$^6$CO—; particularly $R^6$ is hydrogen; and particularly $R^5$ is selected from methyl optionally substituted with one or more A, ethyl optionally substituted with one or more A or phenyl optionally substituted with one or more D.

In another aspect of the invention, where $R^2$ is selected from group ii):
Preferably in group ii) $X^1$ is —O—, —S—, —SO—, —SO$_2$—, NR$^6$ or —NR$^6$CO—; preferably $R^6$ is hydrogen; and preferably $R^5$ is selected from $C_{1-6}$alkyl optionally substituted with one or more A, phenyl optionally substituted with one or more D or phenyl$C_{1-6}$alkyl optionally substituted with one or more D.

More preferably in group ii) $X^1$ is —O—, —S—, —SO—, —SO$_2$— or —NR$^6$CO—; more preferably $R^6$ is hydrogen; and more preferably $R^5$ is selected from $C_{1-4}$alkyl optionally substituted with one or more A, phenyl optionally substituted with one or more D or phenyl$C_{1-4}$alkyl optionally substituted with one or more D.

Where $R^2$ is Selected From Group iii):
Preferably group iii) is a nitrogen-linked 5 or 6 membered heterocyclic group optionally substituted on a ring carbon by one or more D and wherein if said heterocyclic group contains an —NH— moiety that nitrogen may be optionally substituted with a group selected from G.

More preferably group iii) is a nitrogen-linked 6 membered heterocyclic group optionally substituted on a ring carbon by one or more D and wherein if said heterocyclic group contains an —NH— moiety that nitrogen may be optionally substituted with a group selected from G.

Particularly group iii) is morpholino optionally substituted on a ring carbon by one or more D, piperidin-1-yl optionally substituted on a ring carbon by one or more D or piperazin-1-yl optionally substituted on a ring carbon by one or more D and optionally substituted on the —NH— moiety by a group selected from G.

In Another Aspect of the Invention, Where $R^2$ is Selected From Group iii):
Particularly group iii) is morpholino optionally substituted on a ring carbon by one or more D, thiomorpholino optionally substituted on a ring carbon by one or more D, piperidin-1-yl optionally substituted on a ring carbon by one or more D or piperazin-1-yl optionally substituted on a ring carbon by one or more D and optionally substituted on the —NH— moiety by a group selected from G.

More particularly group iii) is thiomorpholino.

In Another Aspect of the Invention, Where $R^2$ is Selected From Group iii):
Particularly group iii) is morpholino, thiomorpholino, 1-oxothiomorpholino, 1,1-dioxothiomorpholino or piperazin-1-yl optionally substituted on the —NH— moiety by a group selected from G.

Preferably A is hydroxy, amino, halo, carboxy and methoxy.

More preferably A is hydroxy.

In another aspect of the invention, preferably A is hydroxy, amino, dimethylamino, halo, carboxy and methoxy.

In another aspect of the invention, more preferably A is hydroxy, methoxy and dimethylamino.

In another aspect of the invention, preferably A is hydroxy, amino, dimethylamino, halo, carboxy, methoxy and carbamoyl.

Where D is Selected From Group i):

Preferably $X^a$ in group i) is —S—, —SO—, —SO$_2$—, —NR$^d$—, —NR$^d$CONR$^e$— or —CONR$^d$—; preferably R$^d$ is hydrogen or C$_{1-4}$alkyl optionally substituted with one or more hydroxy; and preferably R$^e$ is selected from hydrogen or C$_{1-6}$alkyl optionally substituted with one or more hydroxy.

More preferably $X^a$ in group i) is —S—, —SO—, —SO$_2$—, —NR$^d$— or —CONR$^d$—; more preferably R$^d$ is hydrogen, methyl or ethyl optionally substituted with hydroxy; and more preferably R$^e$ is selected from hydrogen or C$_{1-4}$alkyl optionally substituted with one or more hydroxy.

More preferably $X^a$ in group i) is —SO—, —SO$_2$—, —NR$^d$— or —CONR$^d$—; more preferably R$^d$ is hydrogen, methyl or ethyl optionally substituted with hydroxy; and more preferably R$^e$ is selected from hydrogen, methyl or ethyl optionally substituted with hydroxy.

In another aspect of the invention, where D is selected from group i):

Preferably $X^a$ in group i) is —SO—, —SO$_2$—, —NR$^d$— or —CONR$^d$—; more preferably R$^d$ is hydrogen, methyl or ethyl optionally substituted with hydroxy; and more preferably R$^e$ is selected from hydrogen, methyl, ethyl or butyl optionally substituted with hydroxy.

Where D is Selected From Group ii):

Preferably group ii) is a 5 or 6 membered Het which is optionally substituted on a ring carbon with one or more groups selected from hydroxy, halo, C$_{1-4}$alkoxy, C$_{1-4}$alkyl or cyano and wherein if said 5 or 6 membered Het contains an —NH— moiety that nitrogen may be optionally substituted with a group selected from G.

More preferably group ii) is a 5 or 6 membered Het which is optionally substituted on a ring carbon with one or more groups selected from hydroxy, halo, methyl, ethyl, methoxy, ethoxy or cyano and wherein if said 5 or 6 membered Het contains an —NH— moiety that nitrogen may be optionally substituted with a group selected from G.

Particularly group ii) is morpholino, morpholinyl, piperidinyl or piperazinyl optionally substituted on the —NH— moiety by a group selected from G.

Where D is Selected From Group iii):

Preferably group iii) is —$X^a$—C$_{2-4}$alkyl-$X^b$—R$^c$ wherein $X^a$ and R$^c$ are as defined hereinbefore and $X^b$ is preferably —SO— or —SO$_2$—.

Where D is Selected From Group iv):

Preferably group iv) is cyano, fluoro or chloro.

More preferably group iv) is fluoro or chloro.

In Another Aspect of the Invention, Where D is Selected From Group iv):

Preferably group iv) is fluoro.

Where D is Selected From Group v):

Preferably $X^c$ is —C(O)— and R$^f$ is a nitrogen-linked 4–6 membered heterocyclic group optionally substituted by hydroxy.

More preferably $X^c$ is —C(O)— and R$^f$ is azetidinyl, morpholino or pyrrolidinyl (optionally substituted by hydroxy).

Particularly $X^c$ is —C(O)— and R$^f$ is azetidinyl, morpholino or 3-hydroxypyrrolidinyl.

Preferably G is C$_{1-6}$alkanoyl optionally substituted with one or more A or C$_{1-6}$alkyl optionally substituted by one or more A.

More preferably G is C$_{1-4}$alkanoyl optionally substituted with one or more A or C$_{1-4}$alkyl optionally substituted by one or more A.

Particularly G is acetyl or C$_{2-4}$alkyl substituted by one or more A.

More particularly G is acetyl.

Preferably R$^2$ is chloro, fluoro, methylthio, acetylamino, hydroxy, C$_{1-4}$alkylsulphinyl (optionally substituted with hydroxy), C$_{1-4}$alkylsulphonyl (optionally substituted with hydroxy), phenylsulphonyl [optionally substituted with halo, amino, N—(C$_{1-4}$alkyl)$_2$carbamoyl (optionally substituted with hydroxy), N—(C$_{1-4}$alkyl)carbamoyl (optionally substituted with hydroxy), N—(C$_{1-4}$alkyl)amino (optionally substituted with hydroxy), N—(C$_{1-4}$alkyl)$_2$amino (optionally substituted with hydroxy), C$_{1-4}$alkylsulphinyl (optionally substituted with hydroxy), C$_{1-4}$alkylsulphonyl (optionally substituted with hydroxy), 4acetylpiperazin-1-yl, 4-methylpiperazin-1-yl, 4-(2-hydroxyethyl)piperazin-1-yl, 4-(3-hydroxypropyl)-piperazin-1-yl or 4-(2-hydroxypropyl)piperazin-1-yl], pyridylsulphonyl [optionally substituted with halo, amino, N—(C$_{1-4}$alkyl)$_2$amino (optionally substituted with hydroxy), N—(C$_{1-4}$alkyl)$_2$carbamoyl (optionally substituted with hydroxy), N—(C$_{1-4}$alkyl)carbamoyl (optionally substituted with hydroxy), N—(C$_{1-4}$alkyl)amino (optionally substituted with hydroxy), C$_{1-4}$alkylsulphinyl (optionally substituted with hydroxy), C$_{1-4}$alkylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl)piperazin-1-yl], N—(C$_{1-4}$alkyl)amino (optionally substituted with hydroxy), morpholino, 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl)piperazin-1-yl.

More preferably R$^2$ is chloro, fluoro, methylthio, acetylamino, hydroxy, methylsulphinyl, ethylsulphinyl (optionally substituted with hydroxy), mesyl, ethylsulphonyl (optionally substituted with hydroxy), phenylsulphonyl [optionally substituted with halo, amino, N,N-dimethylcarbamoyl, N,N-diethylcarbamoyl (optionally substituted with hydroxy), N-methyl-N-ethylcarbamoyl (optionally substituted with hydroxy), N-methylcarbamoyl, N-ethylcarbamoyl (optionally substituted with hydroxy), methylamino, ethylamino (optionally substituted with hydroxy), N,N-dimethylamino, N,N-diethylamino (optionally substituted with hydroxy), N-methyl-N-ethylamino (optionally substituted with hydroxy), methylsulphinyl, ethylsulphinyl (optionally substituted with hydroxy), mesyl, ethylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl)-piperazin-1-yl or 4-(2-hydroxypropyl)piperazin-1-yl], pyridylsulphonyl [optionally substituted with halo, amino, N,N-dimethylcarbamoyl, N,N-diethylcarbamoyl (optionally substituted with hydroxy), N-methyl-Nethylcarbamoyl (optionally substituted with hydroxy), N-methylcarbamoyl, Nethylcarbamoyl (optionally substituted with hydroxy), N,N-dimethylamino, N,N-diethylamino (optionally substituted with hydroxy), N-methyl-N-ethylamino (optionally substituted with hydroxy), methylsulphinyl, ethylsulphinyl (optionally substituted with hydroxy), methylamino, ethylamino (optionally substituted with hydroxy), mesyl, ethylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl)piperazin-1-yl], methylamino, ethylamino (optionally substituted with hydroxy), morpholino, 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl)piperazin-1-yl.

Particularly R$^2$ is chloro, fluoro, methylthio, acetylamino or hydroxy.

In another aspect of the invention, preferably R$^2$ is chloro, fluoro, bromo, iodo, nitro, amino, methylthio, acetylamino, hydroxy, $C_{1-4}$alkylsulphanyl (optionally substituted with hydroxy), $C_{1-4}$alkylsulphinyl (optionally substituted with hydroxy), $C_{1-4}$alkylsulphonyl (optionally substituted with hydroxy), N—($C_{1-4}$alkyl)amino (optionally substituted with hydroxy, methoxy or dimethylamino), phenylsulphonyl [optionally substituted with halo, amino, N—($C_{1-4}$alkyl)$_2$ carbamoyl (optionally substituted with hydroxy), N—($C_{1-4}$ alkyl)carbamoyl (optionally substituted with hydroxy), N—($C_{1-4}$alkyl)amino (optionally substituted with hydroxy), N—($C_{1-4}$alkyl)$_2$amino (optionally substituted with hydroxy), $C_{1-4}$alkylsulphinyl (optionally substituted with hydroxy), $C_{1-4}$alkylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl)-piperazin-1-yl or 4-(2-hydroxypropyl)piperazin-1-yl], pyridylsulphonyl [optionally substituted with halo, amino, N—($C_{1-4}$alkyl)$_2$amino (optionally substituted with hydroxy), N—($C_{1-4}$alkyl)$_2$carbamoyl (optionally substituted with hydroxy), N—($C_{1-4}$alkyl)carbamoyl (optionally substituted with hydroxy), N—($C_{1-4}$alkyl)amino (optionally substituted with hydroxy), $C_{1-4}$alkylsulphinyl (optionally substituted with hydroxy), $C_{1-4}$alkylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl) piperazin-1-yl], N—($C_{1-4}$alkyl)amino (optionally substituted with hydroxy), morpholino, 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl) piperazin-1-yl], thiomorpholino, phenylsulphanyl (optionally substituted with N—($C_{1-4}$alkyl)$_2$carbamoyl) or phenylsulphinyl (optionally substituted with N—($C_{1-4}$ alkyl)$_2$carbamoyl).

In a further aspect of the invention preferably $R^2$ is chloro, fluoro, bromo, iodo, nitro, hydroxy, amino, methylthio, acetylamino, $C_{1-4}$alkylsulphanyl (optionally substituted with hydroxy), $C_{1-4}$alkylsulphinyl, $C_{1-4}$alkylsulphonyl, N—($C_{1-4}$alkyl)amino (optionally substituted with hydroxy, methoxy or dimethylamino), thiomorpholino, phenylsulphanyl (optionally substituted with N—($C_{1-4}$alkyl)$_2$carbamoyl) or phenylsulphinyl (optionally substituted with N—($C_{1-4}$alkyl)$_2$carbamoyl).

In another aspect of the invention, more preferably $R^2$ is chloro, fluoro, bromo, iodo, nitro, amino, methylthio, acetylamino, hydroxy, methylsulphanyl, ethylsulphanyl (optionally substituted with hydroxy), methylsulphinyl, ethylsulphinyl (optionally substituted with hydroxy), mesyl, ethylsulphonyl (optionally substituted with hydroxy), methylamino, ethylamino (optionally substituted with hydroxy, methoxy or dimethylamino), phenylsulphonyl [optionally substituted with halo, amino, N,N-dimethylcarbamoyl, N,N-diethylcarbamoyl (optionally substituted with hydroxy), N-methyl-N-ethylcarbamoyl (optionally substituted with hydroxy), N-methylcarbamoyl, N-ethylcarbamoyl (optionally substituted with hydroxy), methylamino, ethylamino (optionally substituted with hydroxy), N,N-dimethylamino, N,N-diethylamino (optionally substituted with hydroxy), N-methyl-N-ethylamino (optionally substituted with hydroxy), methylsulphinyl, ethylsulphinyl (optionally substituted with hydroxy), mesyl, ethylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl)-piperazin-1-yl or 4-(2-hydroxypropyl)piperazin-1-yl], pyridylsulphonyl [optionally substituted with halo, amino, N,N-dimethylcarbamoyl, N,N-diethylcarbamoyl (optionally substituted with hydroxy), N-methyl-N-ethylcarbamoyl (optionally substituted with hydroxy), N-methylcarbamoyl, Nethylcarbamoyl (optionally substituted with hydroxy), N,N-dimethylamino, N,N-diethylamino (optionally substituted with hydroxy), N-methyl-N-ethylamino (optionally substituted with hydroxy), methylsulphinyl, ethylsulphinyl (optionally substituted with hydroxy), methylamino, ethylamino (optionally substituted with hydroxy), mesyl, ethylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl) piperazin-1-yl or 4-(2-hydroxypropyl)piperazin-1-yl], methylamino, ethylamino (optionally substituted with hydroxy), morpholino, 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl) piperazin-1-yl], thiomorpholino or phenylsulphanyl [optionally substituted with N,N-dimethylcarbamoyl, N,N-diethylcarbamoyl (optionally substituted with hydroxy), N-methyl-Nethylcarbamoyl (optionally substituted with hydroxy)].

In another aspect of the invention, particularly $R^2$ is fluoro, chloro, bromo, iodo, nitro, amino, hydroxy, methylthio, ethylsulphinyl, mesyl, 2-hydroxyethylamino, 2-methoxyethylamino, 2-dimethylaminoethylamino, 2,3-dihydroxypropylamino, 2-hydroxyethylsulphanyl, acetylamino, 4-N,N-dimethylcarbamoylphenylsulphanyl, 4-N,N-dimethylcarbamoylphenylsulphinyl or thiomorpholino.

In another aspect of the invention, preferably $R^2$ is chloro, fluoro, bromo, iodo, nitro, amino, methoxy, acetylamino, hydroxy, $C_{1-4}$alkylsulphanyl (optionally substituted with hydroxy), $C_{1-4}$alkylsulphinyl, $C_{1-4}$alkylsulphonyl, N—($C_{1-4}$ alkyl)amino (optionally substituted with hydroxy, methoxy, dimethylamino or carbamoyl), morpholino, 4-acetylpiperazin-1-yl, thiomorpholino, 1-oxothiomorpholino, 1,1-dioxothiomorpholino, benzylamino, phenoxy, phenylsulphanyl (optionally substituted with N—($C_{1-4}$alkyl)$_2$carbamoyl) or phenylsulphinyl (optionally substituted with N—($C_{1-4}$alkyl)$_2$carbamoyl).

In another aspect of the invention, more preferably $R^2$ is chloro, fluoro, bromo, iodo, nitro, amino, methoxy, acetylamino, hydroxy, methylthio, 2-hydroxyethylthio, methylsulphinyl, mesyl, 2-hydroxyethylamino, 2-methoxyethylamino, carbamoylmethylamino, 2-dimethylaminoethylamino, 2,3-dihydroxypropylamino, morpholino, 4-acetylpiperazin-1-yl, thiomorpholino, 1-oxothiomorpholino, 1,1-dioxothiomorpholino, benzylamino, phenoxy, 4-(N,N-dimethylcarbamoyl) phenylsulphanyl or 4-(N,N-dimethylcarbamoyl) phenylsulphinyl.

In another aspect of the invention, particularly $R^2$ is methylthio, morpholino, 4-acetylpiperazin-1-yl, 1-oxothiomorpholino or 1,1-dioxothiomorpholino.

In a further aspect of the invention more preferably $R^2$ is amino, 2-hydroxyethylamino or 2-methoxyethylamino.

In an additional aspect of the invention more preferably $R^2$ is fluoro or chloro.

Preferably $R^3$ is $C_{1-6}$alkyl optionally substituted with one or more A, phenyl optionally substituted with one or more D or a carbon-linked 6-membered heteroaryl ring containing 1–2 nitrogen atoms optionally substituted on a ring carbon by one or more D.

More preferably $R^3$ is $C_{1-4}$alkyl optionally substituted with one or more A, phenyl optionally substituted with one or more D or a carbon-linked pyridyl optionally substituted on a ring carbon by one or more D.

Particularly $R^3$ is methyl optionally substituted with one or more A, ethyl optionally substituted with one or more A, phenyl optionally substituted with one or more D or a carbon-linked pyridyl optionally substituted on a ring carbon by one or more D.

Particularly $R^3$ is methyl, ethyl optionally substituted with A, phenyl optionally substituted with one or more D or a carbon-linked pyridyl optionally substituted on a ring carbon by one or more D.

Therefore, in another aspect of the invention preferably $R^3$ is $C_{1-4}$alkyl optionally substituted with one or more hydroxy, phenyl [optionally substituted with halo, amino, N—($C_{1-4}$alkyl)$_2$carbamoyl (optionally substituted with hydroxy), N—($C_{1-4}$alkyl)carbamoyl (optionally substituted with hydroxy), N—($C_{1-4}$alkyl)amino (optionally substituted with hydroxy), N—($C_{1-4}$alkyl)$_2$amino (optionally substituted with hydroxy), $C_{1-4}$alkylsulphinyl (optionally substituted with hydroxy), $C_{1-4}$alkylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl)piperazin-1-yl], or carbon-linked pyridyl [optionally substituted with halo, amino, N—($C_{1-4}$alkyl)$_2$amino (optionally substituted with hydroxy), N—($C_{1-4}$alkyl)$_2$carbamoyl (optionally substituted with hydroxy), N—($C_{1-4}$alkyl)carbamoyl (optionally substituted with hydroxy), N—($C_{1-4}$alkyl)amino (optionally substituted with hydroxy), $C_{1-4}$alkylsulphinyl (optionally substituted with hydroxy), $C_{1-4}$alkylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl)piperazin-1-yl].

Particularly $R^3$ is methyl, ethyl optionally substituted with hydroxy, phenyl [optionally substituted with halo, amino, N,N-dimethylcarbamoyl, N,N-diethylcarbamoyl (optionally substituted with hydroxy), N-methyl-N-ethylcarbamoyl (optionally substituted with hydroxy), N-methylcarbamoyl, N-ethylcarbamoyl (optionally substituted with hydroxy), methylamino, ethylamino (optionally substituted with hydroxy), N,N-dimethylamino, N,N-diethylamino (optionally substituted with hydroxy), N-methyl-N-ethylamino (optionally substituted with hydroxy), methylsulphinyl, ethylsulphinyl (optionally substituted with hydroxy), mesyl, ethylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl)piperazin-1-yl] or carbon-linked pyridyl [optionally substituted with halo, amino, N,N-dimethylcarbamoyl, N,N-diethylcarbamoyl (optionally substituted with hydroxy), N-methyl-N-ethylcarbamoyl (optionally substituted with hydroxy), N-methylcarbamoyl, N-ethylcarbamoyl (optionally substituted with hydroxy), methylamino, ethylamino (optionally substituted with hydroxy), N,N-dimethylamino, N,N-diethylamino (optionally substituted with hydroxy), N-methyl-N-ethylamino (optionally substituted with hydroxy), methylsulphinyl, ethylsulphinyl (optionally substituted with hydroxy), mesyl, ethylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl)piperazin-1-yl].

More particularly $R^3$ is methyl, ethyl optionally substituted with hydroxy, or phenyl (optionally substituted with halo).

Particularly preferred $R^3$ is ethyl or 4-fluorophenyl.

Therefore, in another aspect of the invention preferably $R^3$ is $C_{1-4}$alkyl (optionally substituted with one or more hydroxy), phenyl [optionally substituted with halo, amino, N—($C_{1-4}$alkyl)$_2$carbamoyl (optionally substituted with hydroxy), N—($C_{1-4}$alkyl)carbamoyl (optionally substituted with hydroxy), N—($C_{1-4}$alkyl)amino (optionally substituted with hydroxy), N—($C_{1-4}$alkyl)$_2$amino (optionally substituted with hydroxy), $C_{1-4}$alkylsulphinyl (optionally substituted with hydroxy), $C_{1-4}$alkylsulphonyl (optionally substituted with hydroxy), 4-acetylpiperazin-1-yl, 4-methylpiperazin-1-yl, 4-(2-hydroxyethyl)-piperazin-1-yl, 4-(3-hydroxypropyl)piperazin-1-yl, 4-(2-hydroxypropyl) piperazin-1-yl, azetidinylcarbonyl, morpholinocarbonyl or pyrrolidinylcarbonyl (optionally substituted with hydroxy)], or carbon-linked pyridyl [optionally substituted with halo, amino, N—($C_{1-4}$alkyl)$_2$amino (optionally substituted with hydroxy), N—($C_{1-4}$alkyl)$_2$carbamoyl (optionally substituted with hydroxy), N—($C_{1-4}$allyl)carbamoyl (optionally substituted with hydroxy), N—($C_{1-4}$alkyl)amino (optionally substituted with hydroxy), $C_{1-4}$alkylsulphinyl (optionally substituted with hydroxy), $C_{1-4}$alkylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl)piperazin-1-yl or 4-(2-hydroxypropyl) piperazin-1-yl].

Therefore, in a further aspect of the invention preferably $R^3$ is $C_{1-4}$alkyl (optionally substituted with one or more hydroxy), phenyl [optionally substituted with halo, N—($C_{1-4}$alkyl)$_2$carbamoyl, N—($C_{1-4}$alkyl)carbamoyl, N—($C_{1-4}$alkyl)amino (optionally substituted with hydroxy), $C_{1-4}$alkylsulphonyl, azetidinylcarbonyl, morpholinocarbonyl or pyrrolidinylcarbonyl (optionally substituted with hydroxy)], or carbon-linked pyridyl [optionally substituted with amino].

Particularly $R^3$ is methyl, ethyl (optionally substituted with hydroxy), butyl (optionally substituted with hydroxy), phenyl [optionally substituted with halo, amino, N,N-dimethylcarbamoyl, N,N-diethylcarbamoyl (optionally substituted with hydroxy), N-methyl-N-ethylcarbamoyl (optionally substituted with hydroxy), N-methylcarbamoyl, N-ethylcarbamoyl (optionally substituted with hydroxy), methylamino, ethylamino (optionally substituted with hydroxy), N,N-dimethylamino, N,N-diethylamino (optionally substituted with hydroxy), N-methyl-N-ethylamino (optionally substituted with hydroxy), methylsulphinyl, ethylsulphinyl (optionally substituted with hydroxy), mesyl, ethylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl) piperazin-1-yl, 4-(2-hydroxypropyl)piperazin-1-yl, azetidinylcarbonyl, morpholinocarbonyl or pyrrolidinylcarbonyl (optionally substituted with hydroxy)] or carbon-linked pyridyl [optionally substituted with halo, amino, N,N-dimethylcarbamoyl, N,N-diethylcarbamoyl (optionally substituted with hydroxy), N-methyl-N-ethylcarbamoyl (optionally substituted with hydroxy), N-methylcarbamoyl, N-ethylcarbamoyl (optionally substituted with hydroxy), methylamino, ethylamino (optionally substituted with hydroxy), N,N-dimethylamino, N,N-diethylamino (optionally substituted with hydroxy), N-methyl-N-ethylamino (optionally substituted with hydroxy), methylsulphinyl, ethylsulphinyl (optionally substituted with hydroxy), mesyl, ethylsulphonyl (optionally substituted with hydroxy), 4-acetylpiperazin-1-yl, 4-methylpiperazin-1-yl, 4-(2-hydroxyethyl)piperazin-1-yl, 4-(3-hydroxypropyl) piperazin-1-yl or 4-(2-hydroxypropyl)piperazin-1-yl).

More particularly $R^3$ is methyl, ethyl, 2-hydroxyethyl, 2-hydroxybutyl, 4-fluorophenyl, 4-mesylphenyl, 4-(2-hydroxyethylamino)phenyl, 4-(N-methylcarbamoyl)phenyl, 4-(N-ethylcarbamoyl)phenyl, 4-(N,N-dimethylcarbamoyl)

phenyl, 4-(N-methyl-N-ethylcarbamoyl)phenyl, 4-(azetidinylcarbonyl)phenyl, 4-(morpholinocarbonyl) phenyl, 4-(3-hydroxypyrrolidinylcarbonyl)phenyl or 6-aminopyrid-2-yl.

In another aspect of the invention particularly $R^3$ is methyl, ethyl (optionally substituted with hydroxy), isopropyl, butyl (optionally substituted with hydroxy), phenyl [optionally substituted with halo, N,N-dimethylcarbamoyl, N-methyl-N-ethylcarbamoyl, N-methylcarbamoyl, N-ethylcarbamoyl, ethylamino (optionally substituted with hydroxy), mesyl, azetidinylcarbonyl, morpholinocarbonyl or pyrrolidinylcarbonyl (optionally substituted with hydroxy)] or carbon-linked pyridyl [optionally substituted with amino].

In another aspect of the invention more particularly $R^3$ is methyl, ethyl, 2-hydroxyethyl, isopropyl, 2-hydroxybutyl, 4-fluorophenyl, 4-(2-hydroxyethylamino)phenyl, 4-mesylphenyl, 4-(N,N-dimethylcarbamoyl)phenyl, 4-(N-ethylcarbamoyl)phenyl, 4-(N-methyl-N-ethylcarbamoyl) phenyl, 4-(N-methylcarbamoyl)phenyl, 4-(azetidinylcarbonyl)phenyl, 4-(morpholinocarbonyl) phenyl, 4-(3-hydroxypyrrolidinylcarbonyl)phenyl or 2-aminopyrid-6-yl.

In another aspect of the invention more particularly preferred $R^3$ is methyl, ethyl or isopropyl.

In a further aspect of the invention more particularly preferred $R^3$ is 4-(N-methylcarbamoyl)phenyl or 4-(N,N-dimethylcarbamoyl)phenyl.

In a further aspect of the invention especially particularly preferred $R^3$ is 4-(N,N-dimethylcarbamoyl)phenyl.

In one aspect of the invention, preferably $R^4$ is hydrogen.

In another aspect of the invention, preferably $R^4$ is fluoro.

At the —C(OH)(Me)(CF$_3$) chiral center, the R-configuration is generally the preferred stereochemistry.

Therefore in another aspect of the invention, there is provided a compound of the formula (I) as depicted above wherein:

n is 1 or 2;

$R^1$ is methyl, chloro or fluoro, $R^2$ is chloro, fluoro, bromo, iodo, nitro, amino, methoxy, acetylamino, hydroxy, $C_{1-4}$alkylsulphanyl (optionally substituted with hydroxy), $C_{1-4}$alkylsulphinyl, $C_{1-4}$alkylsulphonyl, N—($C_{1-4}$alkyl)amino (optionally substituted with hydroxy, methoxy, dimethylamino or carbamoyl), morpholino, 4-acetylpiperazin-1-yl, thiomorpholino, 1-oxothiomorpholino, 1,1-dioxothiomorpholino, benzylamino, phenoxy, phenylsulphanyl (optionally substituted with N—($C_{1-4}$alkyl)$_2$ carbamoyl) or phenylsulphinyl (optionally substituted with N—($C_{1-4}$alkyl)$_2$carbamoyl);

$R^3$ is methyl, ethyl (optionally substituted with hydroxy), isopropyl, butyl (optionally substituted with hydroxy), phenyl [optionally substituted with halo, N,N-dimethylcarbamoyl, N-methyl-N-ethylcarbamoyl, N-methylcarbamoyl, N-ethylcarbamoyl, ethylamino (optionally substituted with hydroxy), mesyl, azetidinylcarbonyl, morpholinocarbonyl or pyrrolidinylcarbonyl (optionally substituted with hydroxy)] or carbon-linked pyridyl [optionally substituted with amino]; and $R^4$ is hydrogen;

or a pharmaceutically acceptable salt or an in vivo hydrolysable ester thereof.

Therefore in another aspect of the invention, there is provided a compound of the formula (I) as depicted above wherein:

n is 2;

$R^1$ is chloro;

$R^2$ is methylthio, morpholino, 4-acetylpiperazin-1-yl, 1-oxothiomorpholino or 1,1-dioxothiomorpholino;

$R^3$ is methyl, ethyl or isopropyl;

$R^4$ is hydrogen;

or a pharmaceutically acceptable salt or an in vivo hydrolysable ester thereof.

A preferred compound of the invention is any one of the Examples or a pharmaceutically acceptable salt or an in vivo hydrolysable ester thereof.

More preferred compounds of the invention are Examples 7, 8, 22, 23, 24, 28, 48, 64, 69, 70, 74, 75 or a pharmaceutically acceptable salt or an in vivo hydrolysable ester thereof.

In another aspect of the invention, more preferred compounds of the invention are Examples 32, 35 and 61 or a pharmaceutically acceptable salt or an in vivo hydrolysable ester thereof.

In a further aspect of the invention more preferred compounds of the invention are Examples 17, 18 and 58 or a pharmaceutically acceptable salt or an in vivo hydrolysable ester thereof.

Preferred aspects of the invention are those which relate to the compound or a pharmaceutically acceptable salt thereof.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which elevates PDH activity and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated by those skilled in the art that certain compounds of formula (I) contain one or more asymmetrically substituted carbon and/or sulphur atoms, and accordingly may exist in, and be isolated as enantiomerically pure, a mixture of diastereoisomers or as a racemate. Some compounds may exhibit polymorphism. It is to be understood that the present invention encompasses any racemic, optically-active, enantiomerically pure, mixture of diastereoisomers, polymorphic or stereoisomeric form, or mixtures thereof, which form possesses properties useful in the elevation of PDH activity, it being well known in the art how to prepare optically-active forms (for example, by resolution of the racemic form by recrystallization techniques, by synthesis from optically-active starting materials, by chiral synthesis, by enzymatic resolution, (for example WO 9738124), by biotransformation, or by chromatographic separation using a chiral stationary phase) and how to determine efficacy for the elevation of PDH activity by the standard tests described hereinafter.

It is also to be understood that certain compounds of the formula (I) and salts thereof can exist in solvated as well as unsolvated forms such as, for example, hydrated forms. It is to be understood that the invention encompasses all such solvated forms which elevate PDH activity.

A compound of the formula (I), or salt thereof, and other compounds of the invention (as hereinafter defined) may be prepared by any process known to be applicable to the preparation of chemically-related compounds. Such processes include, for example, those illustrated in European Patent Applications, Publication Nos. 0524781, 0617010, 0625516, and in GB 2278054, WO 9323358 and WO 9738124.

Another aspect of the present invention provides a process for preparing a compound of formula (I) or a pharmaceutically acceptable salt or an in vivo hydrolysable ester thereof, which process (in which variable groups are as defined for formula (I) unless otherwise stated) comprises of:

(a) deprotecting a protected compound of formula (II):

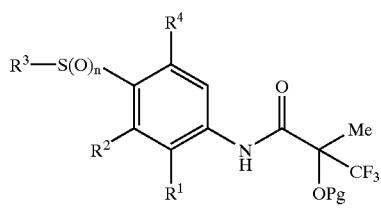

(II)

where Pg is an alcohol protecting group;

(b) oxidising a compound of formula (III):

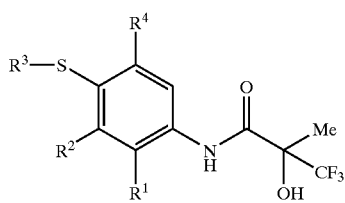

(III)

(c) coupling compounds of formula (IV):

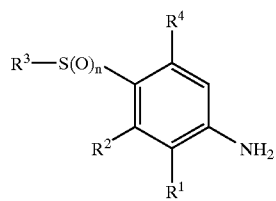

(IV)

with an acid of formula (V):

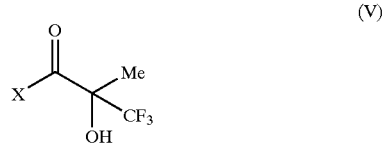

(V)

wherein X is OH;

(d) coupling an aniline of formula (IV) with an activated acid derivative of formula (V); and thereafter if necessary:
i) converting a compound of the formula (I) into another compound of the formula (I);
ii) removing any protecting groups; or
iii) forming a pharmaceutically acceptable salt or in vivo hydrolysable ester.

Suitable values for Pg are a benzyl group, a silyl group (for example a trialkylsilyl group or an alkyldiphenylsilyl group) or an acetyl protecting group.

Where formula (V) is an activated acid derivative, suitable values for X include halo (for example chloro or bromo), anhydrides, aryloxys (for example 4-nitrophenoxy or pentafluorophenoxy) or imidazol-1-yl.

Specific conditions of the above reactions are as follows:

Process a)

Examples of suitable reagents for deprotecting an alcohol of formula (II) are:
1) when Pg is benzyl:
(i) hydrogen in the presence of palladium/carbon catalyst, i.e. hydrogenolysis; or
(ii) hydrogen bromide or hydrogen iodide;
2) when Pg is a silyl protecting group:
(i) tetrabutylammonium fluoride; or
(ii) aqueous hydrofluoric acid;
3) when Pg is acetyl:
i) mild aqueous base for example lithium hydroxide; or
ii) ammonia or an amine such as dimethylamine.

The reaction can be conducted in a suitable solvent such as EtOH, MeOH, acetonitrile, or DMSO and may conveniently be performed at a temperature in the range of 40 to 100° C.

Compounds of formula (II) may be prepared according to the following scheme:

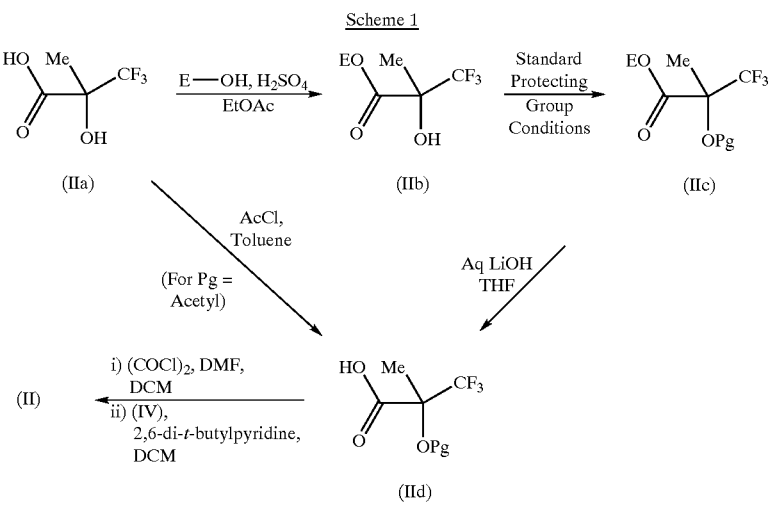

Scheme 1

E is a carboxy protecting group. Suitable values for E include $C_{1-6}$alkyl, such as methyl and ethyl.

Compounds of formula (IIa) are commercially available compounds, or they are known in the literature, or they are prepared by standard processes known in the art. The synthesis of compounds of formula (IV) is described below.

Process b)

Suitable oxidising agents include potassium permanganate, OXONE, sodium periodate, tert-butyl hydroperoxide (as solution in toluene), peracids (such as for example 3-chloroperoxybenzoic acid), hydrogen peroxide, TPAP (tetrapropylammonium perruthenate) or oxygen. The reaction may be conducted in a suitable solvent such as ether, DCM, MeOH, EtOH, water, acetic acid, or mixtures of two or more of these solvents. The reaction may conveniently be performed at a temperature in the range of −40 to 100° C.

Compounds of formula (III) may be prepared according to the following schemes:

Scheme 2

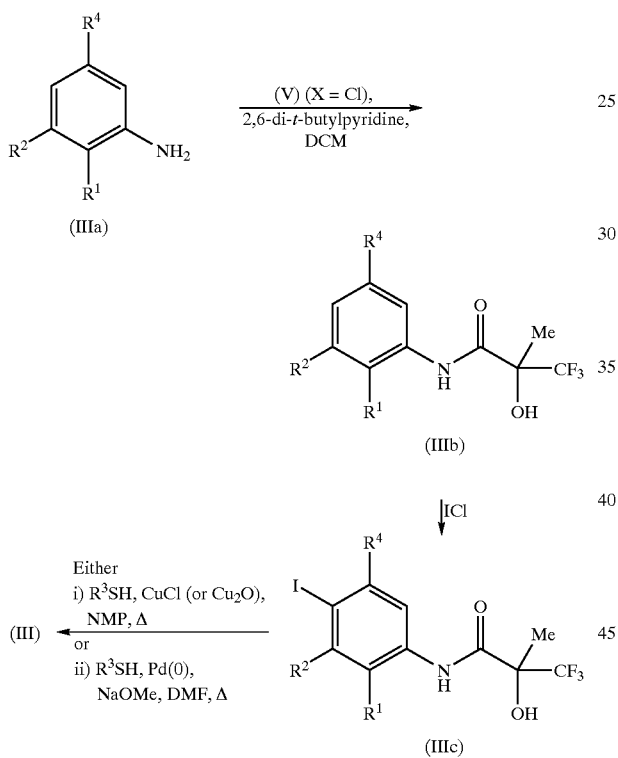

The skilled reader will appreciate that the order of steps 1 and 2 in Scheme 2 may be reversed.

Scheme 3

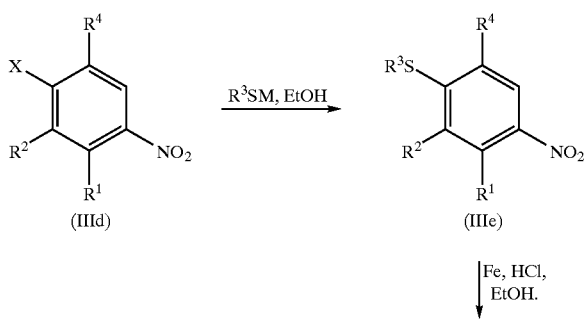

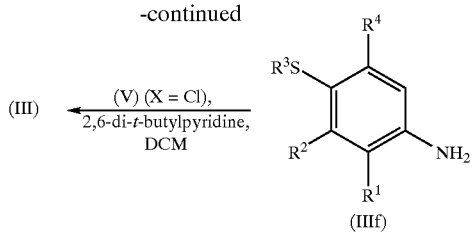

wherein M is an alkali metal. Suitable values for M include lithium, sodium or potassium.

X is a leaving group, suitable values for X include halo, mesyl and tosyl.

Scheme 4

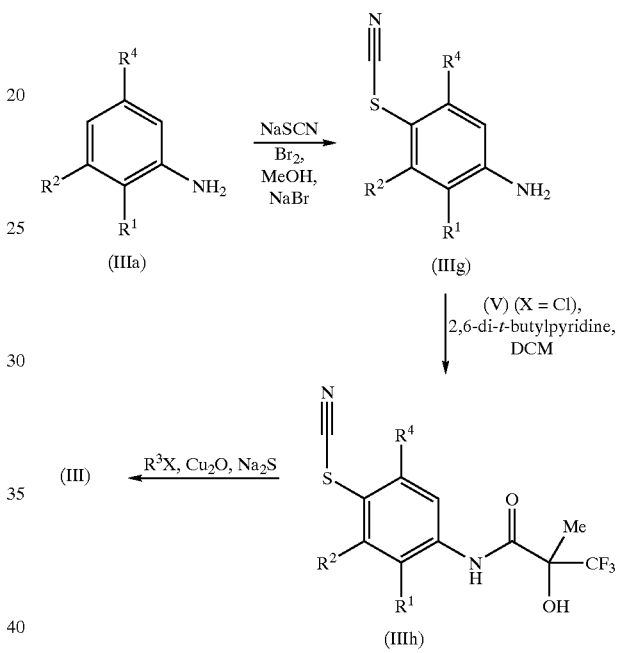

X is a leaving group, suitable values for X include halo, mesyl and tosyl.

Compounds of formula (IIIa) and (IIId) are commercially available compounds, or they are known in the literature, or they are prepared by standard processes known in the art.

Process c)

The reaction can be conducted in the presence of a suitable coupling reagent. Standard peptide coupling reagents known in the art can be employed as suitable coupling reagents, for example conditions such as those described above for the coupling of (IId) and (IV), or for example dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines (such as 2,6-lutidine or 2,6-di-tert-butylpyridine) or 2,6-diphenylpyridine. Suitable solvents include DMA, DCM, benzene, THF, and DMF. The coupling reaction may conveniently be performed at a temperature in the range of −40 to 40° C.

Compounds of formula (IV) are commercially available compounds, or they are known in the literature, or they are prepared by standard processes known in the art, for example they may be prepared by oxidising compounds of formula (IIIf) (with the aniline protected with a suitable protecting group) under standard oxidation conditions, for example with hydrogen peroxide or meta-chloroperoxybenzoic acid (followed by de-protection), or they may be prepared according to the following scheme:

Scheme 5

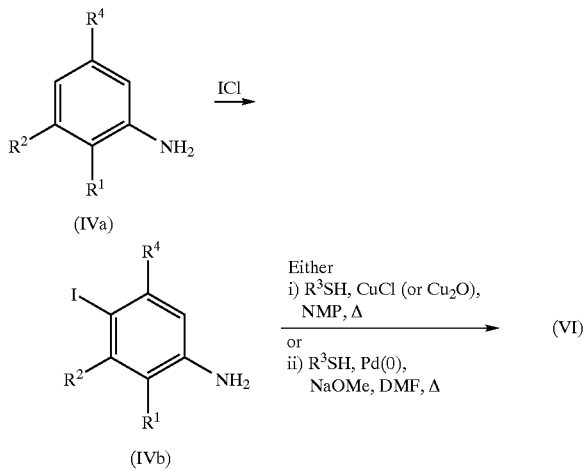

Compounds of formula (IVa) and (V) are commercially available compounds, or they are known in the literature, or they are prepared by standard processes known in the art.

If the resolved acid of formula (V) is required it may be prepared by any of the known methods for preparation of optically-active forms (for example, by recrystallization of the chiral salt {for example WO 9738124}, by enzymatic resolution or by chromatographic separation using a chiral stationary phase). For example if an (R)-(+) resolved acid is required it may be prepared by the method of Scheme 2 in World Patent Application Publication No. WO 9738124 for preparation of the (S)-(−) acid, i.e. using the classical resolution method described in European Patent Application Publication No. EP 0524781, also for preparation of the (S)-(−) acid, except that (1S,2R)-norephedrine may be used in place of (S)-(−)-1-phenylethylamine. The chiral acid may also be prepared by using the enzymatic resolution method as described in Tetrahedron Asymmetry, 1999, 10, 679.

Process d)

This coupling may be achieved optionally in the presence of a base for example triethylamine, pyridine, 2,6-di-alkyl-pyridines (such as 2,6-lutidine or 2,6-di-tert-butylpyridine) or 2,6diphenylpyridine. Suitable solvents include DMA, DCM, benzene, THF, and DMF. The coupling reaction may conveniently be performed at a temperature in the range of −40 to 40° C.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

For example, it will be appreciated that certain of the optional aromatic substituents in the compounds of the present invention may be introduced by standard aromatic substitution reactions or generated by conventional functional group modifications or interconversions either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by, for example, catalytic hydrogenation with a nickel catalyst or treatment with iron in the presence of hydrochloric acid with heating; oxidation of alkylthio to alkylsulphinyl or alkylsulphonyl using, for example, hydrogen peroxide in acetic acid with heating or 3-chloroperbenzoic acid. Particular examples of functional group interconversions are for example conversion of an aniline into a halophenyl by, for example, diazotization in the presence of cuprous halides.

It is noted that many of the starting materials for synthetic methods as described above are commercially available and/or widely reported in the scientific literature, or could be made from commercially available compounds using adaptations of processes reported in the scientific literature.

It will also be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as, for example hydrochloric, sulphuric or phosphoric acid or TFA and an arylmethoxycarbonyl group such as a benzyloxycarbonyl group may be removed, for example, by hydrogenation in the presence of a catalyst such as palladium-on-carbon, or by treatment with a Lewis acid for example boron tris (trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation in the presence of a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as TFA, or for example a benzyl group which may be removed, for example, by hydrogenation over a catalyst such as palladium-on-carbon.

The protecting groups may be removed at any convenient stage in the synthesis using conventional techniques well known in the chemical art.

In cases where compounds of formula (I) are sufficiently basic or acidic to form stable acid or basic salts, administration of the compound as a salt may be appropriate, and pharmaceutically acceptable salts may be made by conventional methods such as those described following. Examples of suitable pharmaceutically acceptable salts are organic acid addition salts formed with acids which form a physiologically acceptable anion, for example, tosylate, methanesulphonate, acetate, tartrate, citrate, succinate, benzoate, ascorbate, α-ketoglutarate, and α-glycerophosphate. Suitable inorganic salts may also be formed such as sulphate, nitrate, and hydrochloride.

Pharmaceutically acceptable salts may be obtained using standard procedures well known in the art, for example by reacting a sufficiently basic compound of formula (I) (or its ester) with a suitable acid affording a physiologically acceptable anion. It is also possible with most compounds of the invention to make a corresponding alkali metal (e.g. sodium, potassium, or lithium) or alkaline earth metal (e.g. calcium) salt by treating a compound of formula (I) (and in some cases the ester) with one equivalent of an alkali metal or alkaline earth metal hydroxide or alkoxide (e.g. the ethoxide or methoxide) in aqueous medium followed by conventional purification techniques.

The compounds of the formula (I) may be administered in the form of a prodrug which is broken down in the human or animal body to give a compound of the formula (I). Examples of prodrugs include in vivo hydrolysable esters of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable in vivo hydrolysable esters for a compound of the formula (I) containing a carboxy group include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable in vivo hydrolysable esters of a compound of the formula (I) containing a hydroxy group includes inorganic esters such as phosphate esters and α-acyloxyalkyl ethers. Examples of α-acyloxyalkyl ethers include acetoxymethoxy and 2,2-dimethylpropionyloxymethoxy. Other in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents for benzoyl include morpholino and piperazino linked from a ring nitrogen atom via a methylene group to the 3- or 4-position of the benzoyl ring.

In vivo cleavable prodrugs of compounds of formula (I) also include in vivo hydrolysable amides of compounds of the formula (I) containing a carboxy group, for example, a N—$C_{1-4}$alkyl or N-di-$C_{1-6}$alkyl amide such as N-methyl, N-ethyl, N-propyl, N-dimethyl, N-ethyl-N-methyl or N-diethyl amide.

The identification of compounds which elevate PDH activity is the subject of the present invention. These properties may be assessed, for example, using one or more of the procedures set out below:

(a) In Vitro Elevation of PDH Activity

This assay determines the ability of a test compound to elevate PDH activity. cDNA encoding PDH kinase may be obtained by Polymerase Chain Reaction (PCR) and subsequent cloning. This may be expressed in a suitable expression system to obtain polypeptide with PDH kinase activity. For example rat PDHkinaseII (rPDHKII) obtained by expression of recombinant protein in *Escherichia coli* (*E. Coli*), was found to display PDH kinase activity.

In the case of the rPDHKII (Genbank accession number U10357) a 1.3 kb fragment encoding the protein was isolated by PCR from rat liver cDNA and cloned into a vector (for example pQE32—Quiagen Ltd.). The recombinant construct was transformed into *E. coli* (for example M15pRep4—Quiagen Ltd.). Recombinant clones were identified, plasmid DNA was isolated and subjected to DNA sequence analysis. One clone which had the expected nucleic acid sequence was selected for the expression work. Details of the methods for the assembly of recombinant DNA molecules and the expression of recombinant proteins in bacterial systems can be found in standard texts for example Sambrook et al, 1989, Molecular Cloning—A Laboratory Manual, $2^{nd}$ edition, Cold Spring Harbour Laboratory Press. Other known PDH kinases for use in assays, may be cloned and expressed in a similar manner.

For expression of rPDHKII activity, *E. coli* strain M15pRep4 cells were transformed with the pQE32 vector containing rPDHKII cDNA. This vector incorporates a 6-His tag onto the protein at its N-terminus. *E. coli* were grown to an optical density of 0.6 (600 nM) and protein expression was induced by the addition of 10 μM isopropylthio-β-galactosidase. Cells were grown for 18 hours at 18° C. and harvested by centrifugation. The resuspended cell paste was lysed by homogenisation and insoluble material removed by centrifugation at 24000×g for 1 hour. The 6-His tagged protein was removed from the supernatant using a nickel chelating nitrilotriacetic acid resin (Ni-NTA: Quiagen Ltd.) matrix (Quiagen) which was washed with 20 mM tris(hydroxymethyl)aminomethane-hydrogen chloride, 20 mM imidazole, 0.5 M sodium chloride pH 8.0, prior to elution of bound protein using a buffer containing 20 mM tris(hydroxymethyl)aminomethane-hydrogen chloride, 200 mM imidazole, 0.15 M sodium chloride pH 8.0. Eluted fractions containing 6-His protein were pooled and stored in aliquots at −80° C in 10% glycerol.

Each new batch of stock enzyme was titrated in the assay to determine a concentration giving approximately 90% inhibition of PDH in the conditions of the assay. For a typical batch, stock enzyme was diluted to 7.5 μg/ml.

For assay of the activity of novel compounds, compounds were diluted with 10% DMSO and 10 μl transferred to individual wells of 96-well assay plates. Control wells contained 20 μl 10% DMSO instead of compound. 40 μl Buffer containing 50 mM potassium phosphate buffer pH 7.0, 10 mM ethylene glycol-bis(β-aminoethyl ether)-N,N-tetracetic acid (EGTA), 1 mM benzamidine, 1 mM phenylmethylsulphonyl fluoride (PMSF), 0.3 mM tosyl-L-lysine chloromethyl ketone (TLCK), 2 mM dithiothreitol (DTT), recombinant rPDHKII and compounds were incubated in the presence of PDH kinase at room temperature for 45 minutes. In order to determine the maximum rate of the PDH reaction a second series of control wells were included containing 10% DMSO instead of compound and omitting rPDHKII. PDH kinase activity was then initiated by the addition of 5 μM ATP, 2 mM magnesium chloride and 0.04 U/ml PDH (porcine heart PDH Sigma P7032) in a total volume of 50 μl and plates incubated at ambient temperature for a further 45 minutes. The residual activity of the PDH was then determined by the addition of substrates (2.5 mM coenzyme A, 2.5 mM thiamine pyrophosphate (cocarboxylase), 2.5 mM sodium pyruvate, 6 mM NAD in a total volume of 80 μl and the plates incubated for 90 minutes at ambient temperature. The production of reduced NAD (NADH) was established by measured optical density at 340 nm using a plate reading spectrophotometer. The $ED_{50}$ for a test compound was determined in the usual way using results from 12 concentrations of the compound.

(b) In Vitro Elevation of PDH Activity in Isolated Primary Cells

This assay determines the ability of compounds to stimulate pyruvate oxidation in primary rat hepatocytes.

Hepatocytes were isolated by the two-step collagenase digestion procedure described by Seglen (Methods Cell Biol. (1976) 13, 29–33) and plated out in 6-well culture plates (Falcon Primaria) at 600000 viable cells per well in Dulbecco's Modified Eagles Medium (DMEM, Gibco BRL) containing 10% foetal calf serum (FCS), 10% penicillin/streptomycin (Gibco BRL) and 10% non-essential amino acids (NEAA, Gibco BRL). After 4 hours incubation at 37° C. in 5% $CO_2$, the medium was replaced with Minimum Essential Medium (MEM, Gibco BRL) containing NEAA and penicillin/streptomycin as above in addition to 10 nM dexamethasone and 10 nM insulin.

The following day cells were washed with phosphate buffered saline (PBS) and medium replaced with 1 ml HEPES-buffered Krebs solution (25 mM HEPES, 0.15M sodium chloride, 25 mM sodium hydrogen carbonate, 5 mM potassium chloride, 2 mM calcium chloride, 1 mM magnesium sulphate, 1 mM potassium dihydrogen phosphate) containing the compound to be tested at the required concentration in 0.1% DMSO. Control wells contained 0.1% DMSO only and a maximum response was determined using a 10 μM treatment of a known active compound. After a preincubation period of 40 minutes at 37° C. in 5% $CO_2$, cells were pulsed with sodium pyruvate to a final concentration of 0.5 mM (containing 1-$^{14}$C sodium pyruvate (Amersham product CFA85) 0.18 Ci/mmole) for 12 minutes. The medium was then removed and transferred to a tube which was immediately sealed with a bung containing a suspended centre well. Absorbent within the centre well was saturated with 50% phenylethylamine, and $CO_2$ in the medium released by the addition of 0.2 μl 60% (w/v) perchloric acid (PCA). Released $^{14}CO_2$ trapped in the absorbent was determined by liquid scintillation counting. The $ED_{50}$ for a test compound was determined in the usual way using results from 7 concentrations of the compound.

(c) In Vivo Elevation of PDH Activity

The capacity of compounds to increase the activity of PDH in relevant tissues of rats may be measured using the test described hereinafter. Typically an increase in the proportion of PDH in its active, nonphosphorylated form may be detected in muscle, heart, liver and adipose tissue after a single administration of an active compound. This may be expected to lead to a decrease in blood glucose after repeated administration of the compound. For example a single administration of DCA, a compound known to activate PDH by inhibition of PDH kinase (Whitehouse, Cooper and Randle (1974) Biochem. J. 141, 761–774) 150 mg/kg, intraperitoneally, increased the proportion of PDH in its active form (Vary et al. (1988) Circ. Shock 24, 3–18) and after repeated administration resulted in a significant decrease in plasma glucose (Evans and Stacpoole (1982) Biochem. Pharmacol.31, 1295–1300).

Groups of rats (weight range 140–180 g) are treated with a single dose or multiple doses of the compound of interest by oral gavage in an appropriate vehicle. A control group of rats is treated with vehicle only. At a fixed time after the final administration of compound, animals are terminally anaesthetised, tissues are removed and frozen in liquid nitrogen. For determination of PDH activity, muscle samples are disrupted under liquid nitrogen prior to homogenisation by one thirty-second burst in a Polytron homogenizer in 4 volumes of a buffer containing 40 mM potassium phosphate pH 7.0, 5 mM EDTA, 2 mM DTT, 1% Triton X-100, 10 mM sodium pyruvate, 10 μM phenylmethylsulphonyl chloride (PMSF) and 2 μg/ml each of leupeptin, pepstain A and aprotinin. Extracts are centrifuged before assay. A portion of the extract is treated with PDH phosphatase prepared from pig hearts by the method of Siess and Wieland (Eur. J. Biochem (1972) 26, 96): 20 μl extract, 40 μl phosphatase (1:20 dilution), in a final volume of 125 μl containing 25 mM magnesium chloride, 1 mM calcium chloride. The activity of the untreated sample is compared with the activity of the dephosphorylated extract thus prepared. PDH activity is assayed by the method of Stansbie et al., (Biochem. J. (1976) 154, 225). 50 μl Extract is incubated with 0.75 mM NAD, 0.2 mM CoA, 1.5 mM thiamine pyrophosphate (TPP) and 1.5 mM sodium pyruvate in the presence of 20 μg/ml p-(p-amino-phenylazo) benzene sulphonic acid (AABS) and 50 mU/ml arylamine transferase (AAT) in a buffer containing 100 mM tris(hydroxymethyl)aminomethane, 0.5 mM EDTA, 50 mM sodium fluoride, 5 mM 2-mercaptoethanol and 1 mM magnesium chloride pH 7.8. AAT is prepared from pigeon livers by the method of Tabor et al. (J. Biol. Chem. (1953) 204, 127). The rate of acetyl CoA formation is determined by the rate of reduction of AABS which is indicated by a decrease in optical density at 460 nm.

Liver samples are prepared by an essentially similar method, except that sodium pyruvate is excluded from the extraction buffer and added to the phosphatase incubation to a final concentration of 5 mM.

Treatment of an animal with an active compound results in an increase in the activity of PDH complex in tissues. This is indicated by an increase in the amount of active PDH (determined by the activity of untreated extract as a percentage of the total PDH activity in the same extract after treatment with phosphatase).

According to a further aspect of the invention there is provided a pharmaceutical composition which comprises a compound of the formula (I) as defined hereinbefore or a pharmaceutically acceptable salt or an in vivo hydrolysable ester thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula (I) or a pharmaceutically acceptable salt or an in vivo hydrolysable ester thereof as defined hereinbefore for use in a method of treatment of the human or animal body by therapy.

We have found that compounds of the present invention elevate PDH activity and are therefore of interest for their blood glucose-lowering effects.

A further feature of the present invention is a compound of formula (I) and pharmaceutically acceptable salts or in vivo hydrolysable esters thereof for use as a medicament.

Conveniently this is a compound of formula (I), or a pharmaceutically acceptable salt or an in vivo hydrolysable ester thereof, for use as a medicament for producing an elevation of PDH activity in a warm-blooded animal such as a human being.

Particularly this is a compound of formula (I), or a pharmaceutically acceptable salt or an in vivo hydrolysable ester thereof, for use as a medicament for treating diabetes mellitus in a warm-blooded animal such as a human being.

In another aspect of the invention, particularly this is a compound of formula (I), or a pharmaceutically acceptable salt or an in vivo hydrolysable ester thereof, for use as a medicament for treating diabetes mellitus, peripheral vascular disease and myocardial ischaemia in a warm-blooded animal such as a human being.

Thus according to a further aspect of the invention there is provided the use of a compound of the formula (I), or a pharmaceutically acceptable salt or an in vivo hydrolysable ester thereof in the manufacture of a medicament for use in the production of an elevation of PDH activity in a warm-blooded animal such as a human being.

Thus according to a further aspect of the invention there is provided the use of a compound of the formula (I), or a pharmaceutically acceptable salt or an in vivo hydrolysable ester thereof in the manufacture of a medicament for use in the treatment of diabetes mellitus in a warm-blooded animal such as a human being.

Thus according to a further aspect of the invention there is provided the use of a compound of the formula (I), or a pharmaceutically acceptable salt or an in viva hydrolysable ester thereof in the manufacture of a medicament for use in the treatment of diabetes mellitus, peripheral vascular disease and myocardial ischaemia in a warm-blooded animal such as a human being.

According to a further feature of the invention there is provided a method for producing an elevation of PDH activity in a warm-blooded animal, such as a human being, in need of such treatment which comprises administering to said animal an effective amount of a compound of formula (I) or a pharmaceutically acceptable salt or an in vivo hydrolysable ester thereof as defined hereinbefore.

According to a further feature of the invention there is provided a method of treating diabetes mellitus in a warm-blooded animal, such as a human being, in need of such treatment which comprises administering to said animal an effective amount of a compound of formula (I) or a pharmaceutically acceptable salt or an in vivo hydrolysable ester thereof as defined hereinbefore.

According to a further feature of the invention there is provided a method of treating diabetes mellitus, peripheral vascular disease and myocardial ischaemia in a warm-blooded animal, such as a human being, in need of such treatment which comprises administering to said animal an effective amount of a compound of formula (I) or a pharmaceutically acceptable salt or an in vivo hydrolysable ester thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The elevation of PDH activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. For example in the treatment of diabetes mellitus chemotherapy may include the following main categories of treatment:

i) insulin;

ii) insulin secretagogue agents designed to stimulate insulin secretion (for example glibenclamide, tolbutamide, other sulphonylureas);

iii) oral hypoglycaemic agents such as metformin, thiazolidinediones;

iv) agents designed to reduce the absorption of glucose from the intestine (for example acarbose);

v) agents designed to treat complications of prolonged hyperglycaemia;

vi) other agents used to treat lactic acidaemia;

vii) inhibitors of fatty acid oxidation;

viii) lipid lowering agents;

ix) agents used to treat coronary heart disease and peripheral vascular disease such as aspirin, pentoxifylline, cilostazol; and/or x) thiamine.

As stated above the compounds defined in the present invention are of interest for their ability to elevate the activity of PDH. Such compounds of the invention may therefore be useful in a range of disease states including diabetes mellitus, peripheral vascular disease, (including intermittent claudication), cardiac failure and certain cardiac myopathies, myocardial ischaemia, cerebral ischaemia and reperfusion, muscle weakness, hyperlipidaemias, Alzheimer's disease and/or atherosclerosis. Alternatively such compounds of the invention may be useful in a range of disease states including peripheral vascular disease, (including intermittent claudication), cardiac failure and certain cardiac myopathies, myocardial ischaemia, cerebral ischaemia and reperfusion, muscle weakness, hyperlipidaemias, Alzheimer's disease and/or atherosclerosis in particular peripheral vascular disease and myocardial ischaemia.

In addition to their use in therapeutic medicine, the compounds of formula (I) and their pharmaceutically acceptable salts are also useful as pharmacological tools in the development and standardisation of in vitro and in vivo test systems for the evaluation of the effects of elevators of PDH activity in laboratory animals such as cats, dogs, rabbits, monkeys, rats and mice, as part of the search for new therapeutic agents.

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C. and under an atmosphere of an inert gas such as argon;

(ii) organic solutions were dried over anhydrous magnesium sulphate; evaporation of solvent was carried out using a rotary evaporator under reduced pressure (6004000 Pascals; 4.5–30 mm Hg) with a bath temperature of up to 60° C.;

(iii) chromatography means flash chromatography on silica gel; thin layer chromatography (TLC) was carried out on silica gel plates; where a silica Mega Bond Elut column is referred to, this means a column containing 10 g or 20 g or 50 g of silica of 40 micron particle size, the silica being contained in a 60 ml disposable syringe and supported by a porous disc, obtained from Varian, Harbor City, Calif., USA under the name "Mega Bond Elut SI"; "Mega Bond Elut" is a trademark; where a Biotage cartridge is referred to this means a cartridge containing KP-SIL™ silica, 60 Å, particle size 32–63 mM, supplied by Biotage, a division of Dyax Corp., 1500 Avon Street Extended, Charlottesville, Va. 22902, USA;

(iv) where a Chem Elut column is referred to, this means a "Hydromatrix" extraction cartridge for adsorption of aqueous material, i.e. a polypropylene tube containing a special grade of flux-calcined, high purity, inert diatomaceous earth, pre-buffered to pH 4.5 or 9.0, incorporating a phase-separation filtering material, used according to the manufacturers instructions, obtained from Varian, Harbor City, Calif., USA under the name of "Extube, Chem Elut"; "Extube" is a registered trademark of International Sorbent Technology Limited;

(v) where an ISOLUTE column is referred to, this means an "ion exchange" extraction cartridge for adsorption of basic or acid material, i.e. a polypropylene tube containing a special grade of ion exchange sorbent, high purity, surface to pH ~7, incorporating a phase-separation filtering material, used according to the manufacturers instructions, obtained from Varian, Harbor City, Calif., USA under the name of "Extube, Chem Elut, ISOLUTE"; "Extube" is a registered trademark of International Sorbent Technology Limited;

(vi) in general, the course of reactions was followed by TLC and reaction times are given for illustration only;

(vii) final products had satisfactory proton nuclear magnetic resonance (NMR) spectra and/or mass spectral data;

(viii) yields are given for illustration only and are not necessarily those which can be obtained by diligent process development; preparations were repeated if more material was required;

(ix) where given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$\delta_6$) as solvent unless otherwise indicated, other solvents (where indicated in the text) include deuterated chloroform —$CDCl_3$; coupling constants (J) are given in Hz; Ar designates an aromatic proton when such an assignment is made;

(x) chemical symbols have their usual meanings; SI units and symbols are used;

(xi) reduced pressures are given as absolute pressures in Pascals (Pa); elevated pressures are given as gauge pressures in bars;

(xii) solvent ratios are given in volume: volume (v/v) terms;

(xiii) mass spectra (MS) were run with an electron energy of 70 electron volts in the chemical ionisation (CI) mode using a direct exposure probe; where indicated ionisation was effected by electron impact (EI), fast atom bombardment (FAB) or electrospray (ESP); values for m/z are given; generally, only ions which indicate the parent mass are reported and unless otherwise stated the value quoted is (M–H)⁻;

(xiv) Oxone is a Trademark of E.I. du Pont de Nemours & Co., Inc., and refers to potassium peroxymonosulphate;

(xv) The following abbreviations are used:

| | |
|---|---|
| ether | diethyl ether; |
| DMF | N,N-dimethylformamide; |
| DMA | N,N-dimethylacetamide; |
| TFA | trifluoroacetic acid; |
| NMP | N-methylpyrrolidin-2-one |
| SM | starting material; |
| DMSO | dimethylsulphoxide; |
| EtOAc | ethyl acetate; |
| MeOH | methanol; |
| EtOH | ethanol; |
| DCM | dichloromethane; and |
| THF | tetrahydrofuran; and |

(xvi) where (R) or (S) stereochemistry is quoted at the beginning of a name, unless further clarified, it is to be understood that the indicated stereochemistry refers to the —NH—C(O)—C*(Me)($CF_3$)(OH) centre as depicted in formula (I).

EXAMPLE 1

(R)-N-(2,3-Dichloro-4-ethylsulphinylphenyl)-2-hydroxy-2-methyl-3,3,3-trifluoropropanamide t-Butyl hydrogen peroxide (2.4 ml of a 5.5M solution in decane) was added to a solution of (R)-N-[2,3-dichloro-4-ethylsulphanylphenyl]-2-hydroxy-2-methyl-3,3,3-trifluoropropanamide Method 1) (0.23 g) and d-10-camphorsulphonic acid (0.018 g) in chloroform (10 ml) and the mixture was stirred for 18 hours. Volatile material was removed by evaporation and the residue was purified by chromatography on a silica gel Mega Bond Elut column eluting with 0–50% EtOAc/isohexane to give the title compound (0.22 g) as a white solid. NMR ($CDCl_3$+1 drop DMSO): 1.21–1.28 (m, 3H), 1.71 (s, 3H), 2.77–2.89 (m, 1H), 3.04–3.16 (m, 1H), 7.14 (s, 1H), 7.78 (d, 1H), 8.66 (d, 1H), 9.73 (s, 1H); m/z: 376.

EXAMPLES 2–8

Following the procedure of Example 1 and using the appropriate starting materials the following compounds were made.

| Ex | Compound | NMR | m/z | SM |
|---|---|---|---|---|
| 2[1] | (R)-N-[4-Methylsulphinyl-3-fluoro-2-chlorophenyl]-2-hydroxy-2-methyl-3,3,3-trifluoropropanamide | 1.62 (s, 3H), 2.86 (s, 3H), 7.71–7.76 (m, 1 H), 8.04–8.10 (m, 1H), 9.94 (brs, 1H) | 346 | Meth 12 |
| 3[1] | (R)-N-[4-Ethylsulphinyl-3-fluoro-2-chlorophenyl]-2-hydroxy-2-methyl-3,3,3-trifluoropropanamide | 1.08 (t, 3H), 1.61 (s, 3H), 2.83–2.94 (m, 1H), 3.08–3.22 (m, 1H), 7.64 (d, 1H), 7.97 (brs, 1H), 8.05–8.09 (m, 1H), 9.94 (brs, 1H) | 360 | Meth 27 |
| 4[2] | (R)-N-[4-Ethylsulphinyl-3-iodo-2-chlorophenyl]-2-hydroxy-2-methyl-3,3,3-trifluoropropanamide | 1.09 (s, 3H), 1.61 (s, 3H), 2.71–2.85 (m, 1H), 3.07–3.19 (m, 1H), 7.62 (d, 1H), 8.27 (d, 1H) | 468 | Meth 28 |
| 5[1] | (R)-N-[4-Methylsulphinyl-2,3-dichlorophenyl]-2-hydroxy-2-methyl-3,3,3-trifluoropropanamide | 1.6 (s, 3H), 2.8 (s, 3H), 7.8 (d, 1H), 7.9 (s, 1H), 8.2 (d, 1H), 9.9 (s, 1H) | 362 | Meth 33 |
| 6[3] | (R)-N-[2-Chloro-3-(1-oxothiomorpholino)-4-(methyl-sulphonyl)phenyl]-2-hydroxy-2-methyl-3,3,3-trifluoropropanamide | 1.61 (s, 3H), 2.83–3.02 (m, 6H), 3.38 (s, 3H), 4.19–4.28 (m, 2H), 7.94 (d, 1H), 8.07 (brs, 1H), 8.23 (d, 1H), 9.95 | 461 | Ex 72 |
| 7[4] | (R)-N-[2-Chloro-3-(1-oxothiomorpholino)-4-(ethyl-sulphonyl)phenyl]-2-hydroxy-2-methyl-3,3,3-trifluoropropanamide | 1.13 (t, 3H), 1.62 (s, 3H), 2.85–2.89 (m, 6H), 3.43–3.50 (q, 2H), 4.17–4.27 (m, 2H), 7.93 (d, 1H), 8.11 (brs, 1H), 8.27 (d, 1H), 9.96 (brs, 1H) | 475 | Ex 65 |
| 8[3] | (R)-N-[2-Chloro-3-(1-oxothiomorpholino)-4-(isopropylsulphonyl)phenyl]-2-hydroxy-2-methyl-3,3,3-trifluoropropanamide | 1.17–1.25 (m, 6H), 1.62 (s, 3H), 2.87 (brm, 6H), 3.71–3.80 (m, 1H), 4.19–4.23 (m, 2H), 7.91 (d, 1H), 8.11 (brs, 1H), 8.26–8.31 (m, 1H), 9.95 (brs, 1H) | 489 | Ex 73 |

[1]Product obtained by addition of DCM to residue after evaporation followed by filtration.
[2]Product was a mixture of two diastereoisomers, Example 4 is the less polar diastereoisomer.
[3]Residue was purified on a 8 g silica Biotage cartridge eluting 3% MeOH/DCM.
[4]Residue was purified on a 8 g silica Biotage cartridge eluting 10% MeOH/EtOAc.

EXAMPLE 9

(R)-N-(2,3-Dichloro-4-ethylsulphonylphenyl)-2-hydroxy-2-methyl-3,3,3-trifluoropropanamide Hydrogen peroxide (15 ml of a 30 wt. % solution in water) was added to a solution of (R)-N-[4-ethylsulphanyl-2,3-dichlorophenyl]-2-hydroxy-2-methyl-3,3,3-trifluoropropanamide (Method 1) (1.88 g) in glacial acetic acid (26 ml) and the mixture was heated at 95° C. for 1.5 hours then cooled. EtOAc (200 ml) was added and the mixture was washed with saturated aqueous sodium hydrogen carbonate solution (4×200 ml) and brine (250 ml) then was dried. Volatile material was removed by evaporation and the residue was purified by chromatography eluting with 0–50% EtOAc/isohexane to give the title compound (1.71 g) as a white solid. NMR: 1.1 (t, 3H), 1.61 (s, 3H), 3.5 (q, 2H), 8.02 (d, 1H), 8.31 (d, 1H); m/z 392.

EXAMPLES 10–26

Following the procedure of Example 9 and using the appropriate starting materials the following compounds were prepared:

| Ex | Compound | NMR | m/z | SM |
|---|---|---|---|---|
| 10 | (R)-N-(3-Acetamido-2-chloro-4-{4-fluorophenylsulphonyl}phenyl)-2-hydroxy-2-methyl-3,3,3-trifluoropropanamide | 1.61 (s, 3H), 1.9 (s, 3H), 7.47 (t, 2H), 7.86 (m, 2H), 8.09 (brs, 1H), 8.22 (d, 1H), 8.40 (d, 1H), 9.81 (brs, 1H), 9.9 (brs, 1H) | 481 | Meth 11 |
| 11 | (R)-N-(2-Chloro-3-fluoro-4-{4-fluorophenylsulphonyl}phenyl)-2-hydroxy-2-methyl-3,3,3-trifluoropropanamide | 1.6 (s, 3H), 7.53 (t, 2H), 7.99–8.2 (m, 5H), 10.0 (brs, 1H) | 442 | Meth 2 |
| 12[1] | (R)-N-[4-(2-Hydroxyethyl-sulphonyl)-2,3-dichloro-phenyl]-2-hydroxy-2-methyl-3,3,3-trifluoropropanamide | 1.62 (s, 3H), 3.66–3.74 (m, 4H), 4.82 (t, 2H), 8.03 (d, 1H), 8.29 (d, 1H), 9.99 (brs, 1H) | 408 | Ex 44 |
| 13 | (R)-N-[4-(2-Hydroxy-n-butyl-sulphonyl)-2,3-dichloro-phenyl]-2-hydroxy-2-methyl-3,3,3-trifluoropropanamide | 0.81 (t, 3H), 1.31–1.52 (m, 2H), 1.62 (s, 3H), 3.50–3.69 (m, 2H), 3.76–3.84 (m, 1H), 0.81 (t, 1H), 8.02 (d, 1H), 8.08 (s, 1H), 8.25–8.29 (m, 1H), 10.01 (s, 1H) | 436 | Meth 34 |
| 14 | (R)-N-(4-Mesyl-3-fluoro-2-chlorophenyl)-2-hydroxy-2-methyl-3,3,3-trifluoropropanamide | 1.62 (s, 3H), 3.35 (s, 3H), 7.84–7.90 (m, 1H), 8.06 (s, 1H), 8.13 (d, 1H), 10.01 (brs, 1H) | 362 | Ex 2 |
| 15 | (R)-N-(4-Ethylsulphonyl-3-fluoro-2-chlorophenyl)-2-hydroxy-2-methyl-3,3,3-trifluoropropanamide | 1.16 (t, 3H), 1.62 (s, 3H), 3.38–3.46 (q, 2H), 7.85 (t, 1H), 8.16 (d, 1H), 10.08 (brs, 1H) | 376 | Meth 27 |
| 16 | (R)-N-(4-Ethylsulphonyl-3-iodo-2-chlorophenyl)-2-hydroxy-2-methyl-3,3,3-trifluoropropanamide | 1.12 (t, 3H), 1.61 (s, 3H), 3.51–3.58 (q, 2H), 8.07 (d, 1H), 8.36 (d, 1H) | 484 | Ex 4 |
| 17 | (R)-N-{2,3-Dichloro-4-[4-(N,N-dimethylcarbamoyl)phenylsulphonyl]phenyl}-2-hydroxy-2-methyl-3,3,3-trifluoropropanamide | 1.60 (s, 3H), 2.85 (s, 3H), 2.95 (s, 3H), 7.60 (d, 2H); 7.95 (d, 2H), 8.10 (s, 1H), 8.40 (dd, 2H), 10.0 (s, 1H) | 511 | Meth 36 |
| 18 | (R)-N-{2-Chloro-3-fluoro-4-[4-(N,N-dimethylcarbamoyl)phenylsulphonyl]phenyl}-2-hydroxy-2-methyl-3,3,3-trifluoropropanamide | 1.60 (s, 3H), 2.95 (s, 3H), 3.00 (s, 3H), 7.65 (d, 2H); 8.05 (d, 2H), 8.05–8.15 (m, 2H), 8.20 (d, 1H), 9.95 (s, 1H) | 495 | Meth 5 |
| 19 | (R)-N-[2-Methyl-3-fluoro-4-(4-fluorophenyl-sulphonyl)phenyl]-2-hydroxy-2-methyl-3,3,3-trifluoropropanamide | 1.61 (s, 3H), 2.05 (s, 3H), 7.50 (t, 2H), 7.62 (d, 1H), 7.66 (brs, 1H), 7.90 (t, 1H), 8.02 (m, 2H), 9.94 (brs, 1 H) | 422 | Meth 43 |
| 20 | (R)-N-(2-Methyl-3-chloro-4-[4-fluorophenyl]sulphonyl phenyl)-2-hydroxy-2-methyl-3,3,3-trifluoropropanamide | 1.60 (s, 3H), 2.20 (s, 3H), 7.46 (t, 2H), 7.60 (brs, 1H), 7.70 (d, 1H), 7.99 (m, 2H), 8.20 (d, 1H), 10.03 (brs, 1H) | 438 | Meth 44 |
| 21 | (R)-N-(2-Methyl-3-fluoro-4-[4-N,N-dimethylcarbamoyl-phenyl]sulphonylphenyl)-2-hydroxy-2-methyl-3,3,3-trifluoropropanamide | 1.60 (s, 3H), 2.07 (s, 3H), 2.85 (s, 3H), 3.00 (s, 3H), 7.66 (m, 4H), 7.98 (m, 3H), 9.90 (brs, 1H) | 475 | Meth 52 |
| 22 | (R)-N-(2-Chloro-3-(1,1-dioxothiomorpholino)-4-(methylsulphonyl)phenyl]-2-hydroxy-2-methyl-3,3,3-trifluoropropanamide | 1.61 (s, 3H), 3.20–3.24 (m, 2H), 3.25–3.39 (m, 4H), 3.37 (s, 3H), 3.89–4.01 (m, 2H), 7.96 (d, 1H), 8.08 (brs, 1H), 8.24 (d, 1H), 9.96 (brs, 1H) | 477 | Ex 72 |

| Ex | Compound | NMR | m/z | SM |
|---|---|---|---|---|
| 23 | (R)-N-[2-Chloro-3-(1,1-dioxothiomorpholino)-4-(ethylsulphonyl)phenyl]-2-hydroxy-2-methyl-3,3,3-trifluoropropanamide | 1.15 (t, 3H), 1.61 (s, 3H), 3.20–3.30 (m, 6H), 3.42–3.49 (q, 2H), 3.87–3.94 (m, 2H), 7.93 (d, 1H), 8.11 (brs, 1H), 8.28 (d, 1H), 9.95 (brs, 1H) | 491 | Ex 65 |
| 24 | (R)-N-[2-Chloro-3-(1,1-dioxothiomorpholino)-4-(isopropylsulphonyl)phenyl]-2-hydroxy-2-methyl-3,3,3-trifluoropropanamide | 1.19–1.23 (m, 6H), 1.61 (s, 3H), 3.24–3.37 (m, 6H), 3.62–3.71 (m, 1H), 3.87–4.01 (m, 2H), 7.91 (d, 1H), 8.12 (brs, 1H), 8.30 (d, 1H), 9.95 (brs, 1H) | 505 | Ex 73 |
| 25[1] | (R)-N-{2-Fluoro-3-chloro-4-[4-(N,N-dimethylcarbamoyl)phenylsulphonyl]phenyl}-2-hydroxy-2-methyl-3,3,3-trifluoropropanamide | 1.6 (s, 3H), 2.8 (s, 6H), 3.0 (s, 3H), 7.6 (d, 2H), 7.8 (d, 1H), 7.95 (d, 2H), 8.1 (dd, 1H), 8.2 (d, 1H), 10.0 (s, 1H) | 495 | Meth 37 |
| 26[1] | (R)-N-{2,3-Difluoro-4-[4-(N,N-dimethylcarbamoyl)phenylsulphonyl]phenyl}-2-hydroxy-2-methyl-3,3,3-trifluoropropanamide | 1.55 (s, 3H), 2.80 (s, 3H), 2.95 (s, 3H), 3.30 (s, 3H), 7.65 (d, 2H), 7.80–7.95 (m, 2H), 8.00 (d, 2H), 10.10 (brs, 1H) | 481 (M + H)+ | Meth 14 |

[1]Water was added to the cooled reaction mixture and the product was obtained by filtration.

EXAMPLE 27

(R)-N-(2-Chloro-4-ethylsulphonyl-3-hydroxyphenyl]-2-hydroxy-2-methyl-3,3,3-trifluoropropanamide Following the procedure of Method 1 using 2-chloro-4-ethylsulphonyl-3-hydroxyaniline (Method 9) as starting material the title compound was obtained (in 10% yield) as a solid. NMR: 0.92 (t, 3H), 1.45 (s, 3H), 3.25 (q, 2H), 7.55 (d, 1H), 7.79 (d, 1H), 7.85 (s, 1H), 9.67 (s, 1H); m/z: 374.

EXAMPLE 28

(R)-N-[2-Chloro-4-ethylsulphonyl-3-methylsulphanylphenyl]-2-hydroxy-2-methyl-3,3,3-trifluoropropanamide Sodium methane thiolate (0.16 g) was added to a stirred solution of (R)-N-[2,3-dichloro-4-ethylsulphonylphenyl]-2-hydroxy-2-methyl-3,3,3-trifluoropropanamide (Example 9) (0.60 g) in anhydrous DMA (10 ml). The reaction mixture was heated under reflux for 3 hours then more sodium methane thiolate (0.27 g) was added and heating was continued a further 18 hours. The reaction mixture was allowed to cool, EtOAc (150 ml) was added, and the mixture was washed with brine (4×100 ml) and dried. Volatile material was removed by evaporation and the residue was purified on a silica gel Mega Bond Elut column eluting with 040% EtOAc/isohexane to give the title compound (0.114 g) as a gum. NMR (CDCl$_3$): 1.26 (t, 3H), 1.78 (s, 3H), 2.50 (s, 3H), 3.64 (q, 2H), 3.75 (s, 1H), 8.13 (d, 1H), 8.67 (d, 1H), 9.44 (s, 1H); m/z: 404.

EXAMPLE 29

(R)-N-{3-Acetamido-2-chloro-4-[4-(2-hydroxyethylamino)phenylsulphonyl]phenyl}-2-hydroxy-2-methyl-3,3,3-trifluoropropanamide (R)-N-[3-Acetamido-2-chloro-4-(4-fluorophenylsulphonyl)phenyl]-2-hydroxy-2-methyl-3,3,3-trifluoropropanamide (683 mg) (Example 10), ethanolamine (177 mg, 2 eq) and acetonitrile (6 ml) were stirred and heated (85° C.) under argon for 24 hours. The solvent was removed and the residual gum was redissolved in MeOH (10 ml) and poured onto deactivated silica (5 g). This was concentrated to give a free flowing powder which was transferred to the top of an ISOLUTE column (50 g silica). This was chromatographed, eluting with MeOH/DCM to give the title compound (247 mg) as a brown solid. NMR (400 MHz): 1.59 (s, 3H), 1.95 (s, 3H), 3.08–3.19 (m, 2H), 3.53 (q, 2H), 4.66–4.73 (t, 1H), 6.62 (d, 2H), 6.67 (t, 1H), 7.0 (brs, 1H), 7.44 (d, 2H), 8.06 (d, 1H), 8.29 (d, 1H), 9.61 (brs, 1H), 9.82 (brs, 1H); m/z 524 (M+H)+.

EXAMPLE 30

(R)-N-[2-Chloro-3-(2-hydroxyethylamino)-4-(4-fluorophenylsulphonyl)phenyl]-2-hydroxy-2-methyl-3,3,3-trifluoropropanamide Ethanolamine (47 mg, 2.5 eq) was added to a solution of (R)-N-(2-chloro-3-fluoro-4-{4-fluorophenylsulphonyl}phenyl)-2-hydroxy-2-methyl-3,3,3-trifluoropropanamide (Example 11) (135 mg) in NMP (1 ml) and the mixture was stirred and heated (oil bath 120° C.) under argon for 24 hours. The reaction mixture was cooled and partitioned between a saturated aqueous solution of ammonium chloride (10 ml) and ether (3×20 ml). The combined ether extracts were washed with water (50 ml), dried and concentrated to give a gum. The residue was dissolved in MeOH/DCM and loaded onto deactivated silica (1 g). It was then concentrated to give a free flowing powder which was poured onto an ISOLUTE column (10 g silica) and chromatographed eluting with EtOAc/isohexane to give the title compound (50 mg) as a gum. NMR: 1.65 (s, 3H), 3.2 (m, 2H), 3.42 (m, 2H), 4.92 (t, 1H), 5.91 (t, 1H), 7.47 (t, 2H), 7.89 (d, 1H), 7.96–8.08 (m, 3H), 9.85 (brs, 1H); m/z: 483.

EXAMPLE 31

(R)-N-{2-Chloro-3-(2-hydroxyethylamino)-4-[4-(2-hydroxyethylamino)phenylsulphonyl]phenyl}-2-hydroxy-2-methyl-3,3,3-trifluoropropanamide The title compound was also isolated from the mixture obtained in Example 30 as a yellow foam. NMR (400 MHz): 1.6 (s, 3H), 3.2 (m, 4H), 3.52 (m, 4H), 4.74 (t, 1H), 4.95 (t, 1H), 5.98 (t, 1H), 6.69 (d, 2H), 6.76 (t, 1H), 7.62 (d, 2H), 8.0 (brs, 1H); m/z: 524.

EXAMPLES 32–39

Following the procedure of Example 30 and using the appropriate starting materials the following compounds were prepared:

| Ex | Compound | NMR | m/z | SM |
|---|---|---|---|---|
| 32 | (R)-N-(2-Chloro-3-(2-hydroxy-ethylamino)-4-[4-(N,N-dimethyl-carbamoyl)phenylsulphonyl]phenyl}-2-hydroxy-2-methyl-3,3,3-trifluoropropanamide | 1.60 (s, 3H), 2.85 (s, 3H), 2.95 (s, 3H), 3.1–3.15 (m, 2H), 3.35–3.4 (m, 2H), 4.9 (dd, 1H), 5.95 (dd, 1H), 7.60 (d, 2H), 7.85 (d, 1H), 7.95–8.05 (m, 4H), 8.10 (s, 1H), 8.40 (dd, 2H), 9.9 (s, 1H) | 536 | Ex 18 |

-continued

| Ex | Compound | NMR | m/z | SM |
|---|---|---|---|---|
| 33 | (R)-N-{2-Chloro-3-(2,3-dihydroxypropylamino)-4-[4-(N,N-dimethylcarbamoyl)phenyl-sulphonyl]phenyl)-2-hydroxy-2-methyl-3,3,3-trifluoropropanamide | 1.60 (s, 3H), 2.80 (s, 3H), 2.85–2.95 (m, 1H), 3.00 (s, 3H), 3.15–3.20 (m, 1H), 3.25–3.35 (m, 2H), 3.40–3.50 (m, 1H), 4.60 (s, 1H), 5.10 (s, 1H), 5.95–6.00 (m, 1H), 7.65 (d, 2H); 7.85 (d, 1H), 7.95–8.05 (m, 4H), 9.85 (s, 1H) | 566 | Ex 18 |
| 34 | (R)-N-{2-Chloro-3-(2-dimethyl-aminoethylamino)-4-[4-(N,N-dimethylcarbamoyl)phenyl-sulphonyl]phenyl}-2-hydroxy-2-methyl-3,3,3-trifluoropropanamide | 1.60 (s, 3H), 2.20 (s, 6H), 2.85 (s, 3H), 2.95 (s, 3H), 3.20–3.25 (m, 2H), 3.30–3.35 (m, 2H), 5.80–5.85 (m, 1H), 7.60 (d, 1H); 7.70 (d, 2H), 7.85–8.05 (m, 4H), 9.95 (s, 1H) | 563 | Ex 18 |
| 35 | (R)-N-{2-Chloro-3-(2-methoxy-ethylamino)-4-[4-(N,N-dimethylcarbamoyl)phenylsulphonyl]phenyl}-2-hydroxy-2-methyl-3,3,3-trifluoropropanamide | (CDCl$_3$): 1.70 (s, 3H), 2.95 (s, 3H), 3.10 (s, 3H), 3.25–3.35 (m, 2H), 3.40 (s, 3H), 3.45–3.55 (m, 2H), 5.80 (dd, 1H), 5.95 (s, 1H), 7.50 (d, 2H); 7.95–8.00 (d, 3H), 8.15 (d, 1H), 9.60 (s, 1H) | 550 | Ex 18 |
| 36 | (R)-N-{2-Chloro-3-thiomorpholino-4-[4-(N,N-dimethylcarbamoyl)phenylsulphonyl)phenyl}-2-hydroxy-2-methyl-3,3,3-trifluoropropanamide | 1.60 (s, 3H), 2.65–2.75 (m, 4H), 2.85 (s, 3H), 2.95 (s, 3H), 3.25–3.30 (m, 2H) 3.40–3.45 (m, 2H), 7.70 (d, 2H); 7.80 (d, 2H), 8.15 (s, 1H), 8.25 (d, 1H), 8.40 (d, 1H), 9.95 (s, 1H) | 578 | Ex 18 |
| 37 | (R)-N-(2-Methyl-3-chloro-4-[4-(2-hydroxyethylamino)phenyl-sulphonyl]phenyl)-2-hydroxy-2-methyl-3,3,3-trifluoropropanamide | 1.65 (s, 3H), 2.22 (s, 3H), 3.20 (m, 2H), 3.60 (m, 2H), 4.76 (t, 1H), 6.73 (d, 2H), 6.81 (t, 1H), 7.63 (m, 4H), 8.13 (d, 1H), 10.04 (brs, 1H) | 479 | Ex 20 |
| 38 | (R)-N-{2-Methyl-3-(2-hydroxy-ethylamino)4-[4-(N,N-dimethyl-carbamoyl)phenylsulphonyl]phenyl}-2-hydroxy-2-methyl-3,3,3-trifluoropropanamide | 1.57 (s, 3H), 2.03 (s, 3H), 2.73 (m, 2H), 2.84 (S, 3H), 2.98 (s, 3H), 3.36 (brs, 2H), 4.87 (brs, 1H), 5.51 (t, 1H), 7.28 (d, 1H), 7.60 (d, 2H), 7.83 (d, 1H), 7.96 (d, 2H), 9.73 (brs, 1H) | 516 | Ex 21 |
| 39 | (R)-N-{2-Fluoro-3-(2-methoxy-ethylamino)-4-[4-(N,N-dimethyl-carbamoyl)phenylsulphonyl]phenyl}-2-hydroxy-2-methyl-3,3,3-trifluoropropanamide | 1.55 (s, 3H), 2.85 (s, 3H), 3.00 (s, 3H), 3.25 (s, 3H), 3.30–3.50 (m, 4H), 6.15 (m, 1H), 7.35 (dd, 1H), 7.60 (d, 2H), 7.80 (d, 1H), 7.80 (s, 1H), 7.90 (d, 1H), 9.65 (brs, 1H) | 534 | Ex 26 |

EXAMPLE 40

(R)-N-[2-Chloro-3-mesyl-4-(4-fluorophenylsulphonyl)phenyl]-2-hydroxy-2-methyl-3,3,3-trifluoropropanamide (R)-N-(2-Chloro-3-fluoro-4-{4-fluorophenylsulphonyl}phenyl)-2-hydroxy-2-methyl-3,3,3-trifluoropropanamide (Example 11) (222 mg) was reacted with sodium methylthiolate (62 mg) in NMP (2 ml) at 120° C. under argon for 18 hours. The cooled reaction mixture was partitioned between a saturated aqueous solution of ammonium chloride (20 ml) and ether (40 ml), the organic layer was separated and the aqueous layer was extracted with more ether (2×40 ml). The combined ether extracts were washed with water (30 ml), dried and concentrated to give a yellow solid (242 mg) which was a mixture of three compounds. This solid was stirred and heated (100° C.) in glacial acetic acid (2 ml) and hydrogen peroxide (100 vol, 0.42 ml) under argon for 80 minutes. The reaction mixture was partitioned between water (20 ml) and EtOAc (50 ml). The organic layer was washed with water (20 ml), dried and concentrated to give a gum. The residue was dissolved in DCM and loaded onto a Biotage cartridge (40 g silica), eluted with 50% EtOAc/isohexane to give the title compound (42 mg) as a white solid. NMR (CDCl$_3$+1 drop DMSO; 500 MHz): 1.63 (s, 3H), 3.37 (s, 3H), 7.09 (t, 2H), 7.49 (s, 1H), 7.76 (m, 2H), 8.45 (d, 1H), 8.89 (d, 1H), 10.1 (brs, 1H); m/z 502.

EXAMPLES 41–42

The other compounds isolated from the above mixture are shown in the following table:

| Ex | Compound | NMR (CDCl$_3$ + 1 drop DMSO; 500 MHz) | m/z | SM |
|---|---|---|---|---|
| 41 | (R)-N-[2-Chloro-3-fluoro-4-(4-mesylphenylsulphonyl)phenyl]-2-hydroxy-2-methyl-3,3,3-trifluoropropanamide | 1.6 (s, 3H), 3.0 (s, 3H), 7.03 (s, 1H), 7.94 (t, 1H), 8.03 (d, 2H), 8.12 (d, 2H), 8.46 (dd, 1H), 9.7 (brs, 1H) | 502 | Ex 11 |
| 42 | (R)-N-[2-Chloro-3-mesyl-4-(4-mesylphenylsulphonyl)phenyl]-2-hydroxy-2-methyl-3,3,3-trifluoropropanamide | 1.65 (s, 3H), 3.0 (s, 3H), 3.38 (s, 3H), 7.4 (s, 1H), 7.89 (d, 2H), 7.98 (d, 2H), 8.54 (d, 1H), 8.97 (d, 1H), 10.1 (brs, 1H) | 562 | Ex 11 |

EXAMPLE 43

(R)-N-[4-Ethylsulphonyl-3-methylsulphinyl-2-chlorophenyl]-2-hydroxy-2-methyl-3,3,3-trifluoropropanamide To a stirred solution of (R)-N-[4-ethylsulphonyl-3-methylsulphanyl-2-chlorophenyl]-2-hydroxy-2-methyl-3,3,3-trifluoropropanamide (Example 28) (0.636 g) in DCM was added metachloroperoxybenzoic acid (0.17 g). After 1 hour at ambient temperature a further portion of meta-chloroperoxybenzoic acid (0.14 g) was added and stirring was continued at ambient temperature for 16 hours. Further meta-chloroperoxybenzoic acid (0.08 g) was added and after 30 minutes sodium hydrogen carbonate solution (50 ml) was added. The organic layer was separated, dried and volatile material was removed by evaporation. The residue was purified by chromatography on a Mega Bond Elut column (20 g) eluting with 10–80% EtOAc/isohexane to give the title compound (0.55 g) as a white foam. NMR: 1.19 (t, 3H), 1.62 (s, 3H), 3.14 (s, 3H), 3.52–3.60 (m, 2H), 8.00 (d, 1H), 8.14 (brs, 1H), 8.45–8.49 (m, 1H), 10.11 (brs, 1H); m/z: 420.

EXAMPLES 44–48

Following the procedure of Example 43 and using the appropriate starting materials the following compounds were made.

| Ex | Compound | NMR | m/z | SM |
|---|---|---|---|---|
| 44 | (R)-N-[2,3-Dichloro-4-(2-hydroxyethylsulphinyl)phenyl]-2-hydroxy-2-methyl-3,3,3-trifluoropropanamide | (CDCl$_3$ + 1 drop DMSO) 1.72 (s, 3H), 2.84–2.91 (m, 1H), 3.39–3.44 (m, 1H), 4.00–4.07 (m, 1H), 4.10–4.18 (m, 1H), 6.99 (s, 1H), 7.85 (d, 1H), 8.70 (d, 1H), 9.73 (brs, 1H) | 392 | Meth 54 |

| Ex | Compound | NMR | m/z | SM |
|---|---|---|---|---|
| 45 | (R)-N-{2-Chloro-4-ethyl-sulphonyl-3-[4-(N,N-dimethyl-carbamoyl)phenylsulphinyl]phenyl}-2-hydroxy-2-methyl-3,3,3-trifluoropropanamide | 1.26–1.31 (m, 3H), 1.58 (s, 3H), 2.86 (s, 3H), 2.97 (s, 3H), 3.64–3.75 (m, 2H), 7.55 (d, 2H), 7.68 (d, 2H), 8.02 (s, 1H), 8.16 (d, 1H), 8.52–8.56 (m, 1H), 10.00 (brs, 1H) | 553 | Ex 51 |
| 46 | (R)-N-{2-Chloro-3-fluoro-4-[4-(N,N-dimethylcarbamoyl)phenylsulphinyl)phenyl}-2-hydroxy-2-methyl-3,3,3-trifluoropropanamide | 1.60 (s, 3H), 2.85 (s, 3H), 2.95 (s, 3H), 7.55 (d, 2H); 7.75 (d, 2H), 7.80–7.85 (m, 1H), 7.90–7.95 (d, 1H), 8.05 (d, 1H), 9.95 (s, 1H) | 479 | Meth 5 |
| 47 | (R)-N-[2,3-Dichloro-4-mesyl-phenyl]-2-hydroxy-2-methyl-3,3,3-trifluoropropanamide | 1.6 (s, 3H), 3.4 (s, 3H), 8.0 (d, 2H), 8.3 (d, 1H), 10.0 (s, 1H) | 378 | Meth 33 |

EXAMPLE 48

(R)-N-(4-Mesyl-3-methylsulphanyl-2-chlorophenyl)-2-hydroxy-2-methyl-3,3,3-trifluoropropanamide Sodium methane thiolate (48 mg) was added to a deoxygenated solution of (R)-N[4-mesyl-3-fluoro-2-chlorophenyl]-2-hydroxy-2-methyl-3,3,3-trifluoropropanamide (Example 14) (0.20 g) in anhydrous NMP (1 ml). The reaction mixture was heated to 120° C. under argon overnight. Further sodium methane thiolate (50 mg) was added and heating was continued for 2 hours and the mixture was allowed to cool to ambient temperature. Saturated ammonium chloride (50 ml) was added and the mixture was extracted into ether (4×50 ml). The ether extracts were combined, washed with brine (50 ml) and dried. Volatile material was removed by evaporation and the residue was purified by chromatography on an 8 g silica gel Biotage cartridge eluting with 3:7 EtOAc/isohexane to give the title compound as a white foam (0.14 g). NMR: 1.62 (s, 3H), 2.47 (s, 3H), 8.05 (d, 1H), 8.36 (d, 1H); m/z: 390.

EXAMPLE 49

(R)-N-[4-Ethylsulphinyl-3-methylsulphanyl-2-chlorophenyl]-2-hydroxy-2-methyl-3,3,3-trifluoropropanamide The title compound was prepared from (R)-N-[4-ethylsulphinyl-3-fluoro-2-chlorophenyl]-2-hydroxy-2-methyl-3,3,3-trifluoropropanamide (Example 3) (0.223 g) by the procedure described in Example 48 to give the title compound as a white solid (55%). NMR: 1.03–1.09 (m, 3H), 1.61 (s, 3H), 2.41 (s, 3H), 2.71–2.82 (m, 1H) 3.08–3.20 (m, 1H), 7.69 (d, 1H), 7.96 (brs, 1H), 8.28–8.32 (m, 1H), 9.92 (brs, 1H); m/z: 388.

EXAMPLE 50

(R)-N-{2-Chloro-3-(2-hydroxyethylthio)-4-[4-(N,N-dimethylcarbamoyl)phenylsulphonyl]phenyl}-2-hydroxy-2-methyl-3,3,3-trifluoropropanamide To (R)-N-{2-chloro-3-fluoro-4-[4-(N,N-dimethylcarbamoyl)phenylsulphonyl]phenyl}-2-hydroxy-2-methyl-3,3,3-trifluoropropanamide (Example 18) (600 mg), as a solution in NMP (5 ml), was added 2-hydroxyethanethiol (0.1 ml) and sodium methoxide (0.65 g), and the reaction mixture was heated at 120° C. overnight under an argon atmosphere. The solution was diluted with saturated brine and extracted with ether (3×30 ml). The ether extracts were combined and dried. The volatile material was removed by evaporation and purified by chromatography on a Mega Bond Elut column (20 g silica) eluting with hexane/EtOAc to yield the title compound as a white solid (60 mg, 12%). NMR: 1.60 (s, 3H), 2.60–2.65 (m, 2H),), 2.85 (s, 3H), 2.95 (s, 3H), 3.10–3.20 (m, 2H), 4.75 (dd, 1H), 7.60 (d, 2H); 7.95 (d, 2N), 8.05 (s, 1H), 8.35 (d, 1H), 8.45 (d, 1H), 9.95 (s, 1H); m/z: 553.

EXAMPLE 51

(R)-N-{4-Ethylsulphonyl-3-[4-(N,N-dimethylcarbamoyl)phenylsulphanyl]-2-chlorophenyl}-2-hydroxy-2-methyl-3,3,3-trifluoropropanamide To a stirred solution of (R)-N-[4-ethylsulphonyl-3-(4-carboxyphenylsulphanyl)-2-chlorophenyl]-2-hydroxy-2-methyl-3,3,3-trifluoropropanamide (Method 59) (0.64 g) in DCM (20 ml) and DMF (3 drops) was added oxalyl chloride (0.25 ml). The reaction mixture was allowed to stir at ambient temperature overnight. Volatile material was evaporated and the residue was redissolved in DCM (20 ml) and dimethylamine (1 ml, 5.6 M solution in EtOH) was added. The mixture was allowed to stir at room temperature for 3 hours. HCl (2M, 50 ml) was added and the organic phase was separated, dried and volatile material was removed by evaporation. The residue was purified by chromatography on a Mega Bond Elut column (50 g silica) eluting with 1–3% MeOH/DCM to give the title compound as a brown foam (0.67 g). NMR (CDCl$_3$) 1.20 (t, 3H), 1.64 (s, 3H), 2.89 (s, 3H), 3.01 (s, 3H), 3.41–3.48 (q, 2H), 5.37 (s, 1H), 7.03 (d, 2H), 7.22 (d, 2H), 8.18 (d, 1H), 8.72 (d, 1H), 9.56 (s, 1H); m/z: 537.

EXAMPLES 52–60

Following the procedure of Example 51 and using the appropriate starting materials the following compounds were made.

| Ex | Compound | NMR | m/z | SM |
|---|---|---|---|---|
| 52 | (R)-N-{2-Chloro-3-[4-(N,N-dimethylcarbamoyl)phenyl-sulphanyl]-(N,N-dimethylcarbamoyl)phenyl-sulphonyl]phenyl}-2-hydroxy-2-methyl-3,3,3-trifluoropropanamide | 1.60 (s, 3H), 2.80–3.00 (m, 12H), 7.40–7.50 (m, 4H); 7.60 (d, 2H), 7.95 (d, 2H), 8.05 (s, 1H), 8.50 (d, 1H), 8.60 (d, 1H), 9.95 (s, 1H) | 656 | Meth 76 |
| 53[1] | (R)-N-{2-Methyl-3-chloro-4-[4-(N,N-dimethylcarbamoyl)phenylsulphonyl]phenyl}-2-hydroxy-2-methyl-3,3,3-trifluoropropanamide | 1.59 (s, 3H), 2.19 (s, 3H), 2.86 (s, 3H), 2.99 (s, 3H), 7.65 (d, 2H), 7.75 (d, 1H), 7.94 (d, 2H), 8.22 (d, 1H), 10.01 (brs, 1H) | 491 | Meth 60 |
| 54 | (R)-N-(2-Methyl-3-bromo-4-[4-(N,N-dimethylcarbamoyl)phenylsulphonyl]phenyl}-2-hydroxy-2-methyl-3,3,3-trifluoropropanamide | 1.60 (s, 3H), 2.25 (s, 3H), 2.84 (s, 3H), 3.00 (s, 3H), 7.62 (d, 2H), 7.75 (d, 1H), 7.93 (d, 2H), 8.26 (d, 1H), 10.06 (brs, 1H) | 535 | Meth 61 |
| 55[2] | (R)-N-(2,3-Dichloro-4-[4-(N-ethylcarbamoyl)phenyl-sulphonyl]phenyl}-2-hydroxy-2-methyl-3,3,3-trifluoropropanamide | 1.1 (t, 3H), 1.6 (s, 3H), 3.3 (q, 2H), 8.0 (s, 4H), 8.1 (s, 1H), 8.4 (q, 4H), 8.7 (t, 1H), 9.9 (s, 1H) | 511 | Meth 66 |

-continued

| Ex | Compound | NMR | m/z | SM |
|---|---|---|---|---|
| 56[2] | (R)-N-{2,3-Dichloro-4-[4-(N-ethyl-N-methylcarbamoyl)phenylsulphonyl]phenyl}-2-hydroxy-2-methyl-3,3,3-trifluoropropanamide | 1.1 (m, 3H), 1.6 (s, 3H), 2.8 (s, 1H), 2.9 (s, 1H), 3.1 (q, 1H), 3.5 (q, 1H), 7.6 (d, 2H), 7.9 (d, 2H), 8.1 (s, 1H), 8.4 (q, 2H), 9.9 (s, 1H) | 525 | Meth 66 |
| 57[2] | (R)-N-{2,3-Dichloro-4-[4-(3-hydroxypyrrolidin-1-ylcarbonyl)phenylsulphonyl]phenyl}-2-hydroxy-2-methyl-3,3,3-trifluoropropanamide | 1.6 (s, 3H), 1.8 (m, 2H), 3.5 (m, 2H), 4.3 (d, 1H), 4.9 (d, 1H), 7.7 (m, 2H), 7.9 (d, 2H), 8.1 (s, 1H), 8.4 (q, 2H), 9.9 (s, 1H) | 553 | Meth 66 |
| 58[2] | (R)-N-(2,3-Dichloro-4-[4-(N-methylcarbamoyl)phenyl-sulphonyl]phenyl}-2-hydroxy-2-methyl-3,3,3-trifluoropropanamide | 1.6 (s, 3H), 2.8 (d, 3H), 8.0 (s, 4H), 8.1 (s, 1H), 8.4 (q, 2H), 8.7 (d, 1H), 9.9 (s, 1H) | 497 | Meth 66 |
| 59[2] | (R)-N-{2,3-Dichloro-4-[4-(azetidin-1-ylcarbonyl)phenylsulphonyyl)phenyl}-2-hydroxy-2-methyl-3,3,3-trifluoropropanamide | 1.6 (s, 3H), 2.2 (m, 2H), 4.1 (t, 2H), 4.3 (t, 2H), 7.8 (d, 2H), 8.0 (d, 2H), 8.1 (s, 1H), 8.4 (q, 2H), 9.9 (s, 1H) | 523 | Meth 66 |
| 60[2] | (R)-N-(2,3-Dichloro-4-[4-(morpholinocarbonyl)phenylsulphonyl)phenyl}-2-hydroxy-2-methyl-3,3,3-trifluoropropanamide | 1.6 (s, 3H), 3.6 (m, 8H), 7.6 (d, 2H), 8.0 (d, 2H), 8.0 (d, 2H), 8.4 (q, 2H) | 553 | Meth 66 |

[1]An oil resulted following chromatography, this was dissolved in EtOAc and washed with water, brine and dried. The volatile material was removed by evaporation and the residue was then triturated with ether.
[2]The residue was chromatographed using graduated solvents of EtOAc/hexane.

EXAMPLE 61

(R)-N-{2-Chloro-3-amino-4-[4-(N,N-dimethylcarbamoyl)phenyl]sulphonylphenyl}-2-hydroxy-2-methyl-3,3,3-trifluoropropanamide Iron (324 mg) and conc. hydrochloric acid (1 drop) was added to a suspension of (R)-N-{2-chloro-3-nitro-4-[4-(N,N-dimethylcarbamoyl)phenyl]sulphonylphenyl}-2-hydroxy-2-methyl-3,3,3-trifluoropropanamide (Example 63) (305 mg) in water (0.25 ml) and EtOH (1 ml). The mixture was stirred for 1.5 hours at 75° C. and allowed to cool to ambient temperature. Saturated NaHCO$_3$ (10 ml) was added and the solution was extracted with EtOAc (100 ml). The extracts were washed with brine (40 ml) and dried. The volatile material was removed by evaporation. The reaction had not gone to completion, so additional iron (324 mg) and conc. hydrochloric acid (3 drop) was added to a suspension of the residue in water (0.25 ml) and EtOH (1 ml). The mixture was stirred for 3 hours at 75° C. After the mixture was allowed to cool to ambient temperature, saturated NaHCO$_3$ (10 ml) was added and the solution was extracted with EtOAc (100 ml). The extracts were washed with brine (40 ml) and dried. The volatile material was removed by evaporation to give a foam. This was purified by chromatography on silica gel, eluted with 4% MeOH in DCM to give the title compound as a foam (250 mg). NMR: 1.58 (s, 3H), 2.81 (s, 3H), 2.95 (s, 3H), 6.31 (s, 2), 7.60 (m, 3H), 7.81 (d, 1H), 7.96 (m, 3H), 9.73 (brs, 1H), m/z 492.

EXAMPLE 62

(R)-N-[4-{2-Aminopyrid-6-ylsulphonyl}-2,3-dichlorophenyl]-2-hydroxy-2-methyl-3,3,3-trifluoropropanamide (R)-N-[4-{2-Nitropyridyl}-6-sulphonyl-2,3,dichlorophenyl]-2-hydroxy-2-methyl-3,3,3-trifluoropropanamide (Method 71) (220 mg, 0.45 mmol) was stirred and heated at 75° C. for 1 hour with iron powder (272 mg), EtOH (0.3 ml), water (0.11 ml) and 1 drop of conc. HCl. The reaction mixture was allowed to cool to room temperature, and the mixture was made basic with saturated Na$_2$CO$_3$ solution. EtOAc was added and the mixture was filtered through a bed of diatomaceous earth and washed through thoroughly with EtOAc/water. The organic layers were washed with brine, poured onto a Chem Elut column and eluted with EtOAc. Purification was achieved with a Mega Bond Elut column and graduated solvent 10–80% EtOAc/hexane to yield the title compound (15 mg) as a white foam. NMR: 1.6 (s, 3H), 6.4 (s, 2H), 7.0 (d, 1H), 7.9 (t, 2H), 8.0 (s, 1H), 8.3 (q, 2H), 9.9 (s, 1H); m/z: 456.

EXAMPLE 63

(R)-N-(2-Chloro-3-nitro-4-[4-N,N-dimethylcarbamoylphenylsulphonyl]phenyl)-2-hydroxy-2-methyl-3,3,3-trifluoropropanamide Oxalyl Chloride (0.07 ml) and DMF (2 drops) were added to a solution of (R)-N-(2-chloro-3-nitro-4-[4-carboxyphenylsulphonyl]phenyl)-2-hydroxy-2-methyl-3,3,3-trifluoropropanamide (Method 62) (260 mg) in DCM (15 ml). The mixture was stirred for 16 hours at ambient temperature. The volatile material was removed by evaporation and the residue was dissolved in DCM (15 ml). Dimethylamine in EtOH (5.6M, 0.6 ml) was added and the solution was stirred for 16 hours at ambient temperature. The volatile material was removed by evaporation and the residue was partitioned between EtOAc (100 ml) and water (50 ml). The organic phase was washed with brine (50 ml) and dried. Volatile material was removed by evaporation to give the title compound (324 mg) as a solid. NMR: 1.58 (s, 3H), 2.83 (s, 3H), 2.97 (s, 3H), 7.66 (d, 2H), 7.93 (d, 2H), 8.08 (brs, 1H), 8.35 (d, 1H), 8.42 (d, 1H); m/z 522.

EXAMPLE 64

(R)-N-[2-Chloro-3-(4-acetylpiperazin-1-yl)-4-(ethylsulphonyl)phenyl]-2-hydroxy-2-methyl-3,3,3-trifluoropropanamide (R)-N-[2-Chloro-3-fluoro-4-(ethylsulphonyl)phenyl]-2-hydroxy-2-methyl-3,3,3-trifluoropropanamide (Example 15; 2.0 g) was added to a solution of 1-acetylpiperazine (2.0 g, 3 eq) in anhydrous NMP (3 ml) under argon and the mixture was stirred and heated to 147° C. for 24 hours. The reaction mixture was cooled and partitioned between a saturated aqueous solution of ammonium chloride (80 ml) and ether (4×200 ml). The combined ether extracts were washed with brine (200 ml), dried and concentrated to give a gum. The residue was purified by chromatography on a Mega Bond Elut column (50 g) eluting with 0–4% MeOH/DCM to give the title compound (0.895 g) as a white foam. NMR: 1.14 (t, 3H), 1.61 (s, 3H), 2.05 (s, 3H), 2.75–2.82 (m, 1H), 2.94 (brm, 2H), 3.25–3.44 (m, 3H), 3.49–3.56 (q, 2H), 3.85 (d, 1H), 4.39 (d, 1H), 7.94 (d, 1H), 8.07 (brs, 1H), 8.26 (d, 1H), 9.94 (brs, 1H); m/z: 484.

EXAMPLES 65–76

Following the procedure of Example 64 and using the appropriate starting materials the following compounds were made.

| Ex No | Compound | NMR | m/z |
|---|---|---|---|
| 65[1] | (R)-N-[2-Chloro-3-thiomorpholino-4-(ethylsulphonyl)phenyl]-2-hydroxy-2-methyl-3,3,3-trifluoropropanamide | 1.15 (t, 3H), 1.61 (s, 3H), 2.50–2.56 (m, 2H), 2.89–2.97 (m, 2H), 3.14–3.20 (m, 2H), 3.47–3.54 (m, 2H), 3.62–3.71 (m, 2H), 7.91 (d, 1H), 8.01 (brs, 1H), 8.25 (d, 1H), 9.90 (brs, 1H) | 459 |
| 66[2,3] | (R)-N-[2-Chloro-3-(2-hydroxyethylamino)-4-(ethylsulphonyl)phenyl]-2-hydroxy-2-methyl-3,3,3,-trifluoropropanamide | 1.10 (t, 3H), 1.61 (s, 3H), 3.37–3.44 (m, 4H), 3.56–3.61 (m, 2H), 4.96 (t, 1H), 5.97 (t, 1H), 7.68 (d, 1H), 7.84 (d, 1H), 8.06 (brs, 1H), 9.92 (brs, 1H) | 417 |
| 67[4,5] | (R)-N-[2-Chloro-3-benzylamino-4-(ethylsulphonyl)phenyl]-2-hydroxy-2-methyl-3,3,3-trifluoropropanamide | (CDCl$_3$) 1.07 (t, 3H), 1.78 (s, 3H), 2.64–2.71 (q, 2H), 3.72 (s, 1H), 4.58 (d, 2H), 6.02 (t, 1H), 7.30–7.34 (m, 5H), 7.73 (d, 1H), 8.14 (d, 1H), 9.35 (s, 1H) | 463 |
| 68[6,7] | (R)-N-[2-Chloro-3-(carbamoylmethylamino)-4-(ethylsulphonyl)phenyl]-2-hydroxy-2-methyl-3,3,3-trifluoropropanamide | 1.08 (t, 3H), 1.61 (s, 3H), 3.36–3.41 (q, 2H), 4.08 (d, 2H), 6.43 (t, 1H), 7.23 (brs, 1H), 7.60 (brs, 1H), 7.66 (d, 1H), 7.82 (d, 1H), 8.06 (brs, 1H), 9.88 (brs, 1H) | 430 |
| 69[8,9] | (R)-N-[2-Chloro-3-(1-(4-acetyl)piperazinyl)-4-(methylsulphonyl)phenyl]-2-hydroxy-2-methyl-3,3,3-trifluoropropanamide | 1.61 (s, 3H), 2.05 (s, 3H), 2.79–2.87 (m, 1H), 2.98 (brm, 2H), 3.40 (s, 3H), 3.30–3.54 (m, 3H), 3.85 (d, 1H), 4.39 (d, 1H), 7.96 (d, 1H), 8.09 (brs, 1H), 8.22 (d, 1H), 9.94 (brs, 1H) | 470 |
| 70[3,8] | (R)-N-[2-Chloro-3-morpholino-4-(methylsulphonyl)phenyl]-2-hydroxy-2-methyl-3,3,3-trifluoropropanamide | 1.61 (s, 3H), 2.80–2.84 (m, 2H), 3.41 (s, 3H), 3.64–3.68 (m, 4H), 3.81–3.83 (m, 2H), 7.94 (d, 1H), 8.05 (brs, 1H), 8.21 (d, 1H), 9.96 (brs, 1H) | 429 |
| 71[8,10,11] | (R)-N-[2-Chloro-3-(2-methoxyethylamino)-4-(methylsulphonyl)phenyl]-2-hydroxy-2-methyl-3,3,3-trifluoropropanamide | 1.61 (s, 3H), 3.28 (s, 3H), 3.38 (s, 3H), 3.51–3.57 (m, 4H), 5.88 (t, 1H), 7.73 (d, 1H), 7.83 (d, 1H), 8.05 (brs, 1H), 9.90 (brs, 1H) | 417 |
| 72[8,12] | (R)-N-[2-Chloro-3-(thiomorpholino)-4-mesylphenyl]-2-hydroxy-2-methyl-3,3,3-trifluoropropanamide | 1.61 (s, 3H), 2.50–2.56 (m, 2H), 2.92–3.00 (m, 2H), 3.16–3.23 (m, 2H), 3.37 (s, 3H), 3.60–3.72 (m, 2H), 7.93 (d, 1H), 8.07 (brs, 1H), 8.21 (d, 1H), 9.94 (brs, 1H) | 445 |
| 73[12,13] | (R)-N-[2-Chloro-3-thiomorpholino-4-(isopropylsulphonyl)phenyl)-2-hydroxy-2-methyl-3,3,3-trifluoropropanamide | 1.17–1.22 (m, 6H), 1.61 (s, 3H), 2.50–2.56 (m, 2H), 2.85–2.94 (m, 2H), 3.13–3.19 (m, 2H), 3.61–3.71 (m, 2H), 3.80–3.90 (m, 1H), 7.90 (d, 1H), 8.09 (brs, 1H), 8.26 (d, 1H), 9.93 (brs, 1H) | 473 |
| 74[13,14] | (R)-N-[2-Chloro-3-(4-acetyl-piperazin-1-yl)-4-(isopropylsulphonyl)-2-hydroxy-2-methyl-3,3,3-trifluoropropanamide | 1.17–1.24 (m, 6H), 1.61 (s, 3H), 2.05 (s, 3H), 2.71–2.78 (m, 1H), 2.94 (brm, 2H), 3.22–3.30 (m, 1H), 3.40–3.53 (m, 2H), 3.82–3.93 (m, 2H), 4.39 (d, 1H), 7.93 (d, 1H), 8.11 (brs, 1H), 8.27 (d, 1H), 9.90 (brs, 1H) | 498 |
| 75[3,13] | (R)-N-[2-Chloro-3-morpholino-4-(isopropylsulphonyl)phenyl]-2-hydroxy-2-methyl-3,3,3-trifluoropropanamide | 1.16–1.22 (m, 6H), 1.61 (s, 3H), 2.74–2.79 (m, 2H), 3.54–3.67 (m, 4H), 3.80–3.83 (m, 2H), 3.90–3.97 (m, 1H), 7.91 (d, 1H), 8.09 (brs, 1H), 8.25 (d, 1H), 9.95 (brs, 1H) | 457 |
| 76[10,11,13] | (R)-N-[2-Chloro-3-(2-methoxyethylamino)-4-phenyl](isopropylsulphonyl)-2-hydroxy-2-methyl-3,3,3-trifluoropropanamide | 1.15–1.23 (m, 6H), 1.61 (s, 3H), 3.33 (s, 3H), 3.53–3.58 (m, 4H), 4.06–4.12 (m, 1H), 5.98 (t, 1H), 7.66 (d, 1H), 7.87 (d, 1H), 8.09 (brs, 1H), 9.89 (brs, 1H) | 445 |

[1]The residue was chromatographed using 0–50% EtOAc/isohexane as eluent
[2]Ethanolamine (1.5 eq) was used at 120° C. for 3 hours
[3]Residue was purified on an 8 g silica Biotage cartridge eluting with 1:1 EtOAc/isohexane
[4]Benzylamine (1.5 eq) was used at 110° C. for 3 hours
[5]Residue purified using 0–40% EtOAc/isohexane as eluent
[6]Glycinamide hydrochloride (3 eq) and triethylamine (3 eq) were used at 120° C. for 24 hours
[7]Residue was purified on a 8 g silica Biotage cartridge eluting with EtOAc
[8]Starting Material: Example 14
[9]After chromatography the residue was filtered from hot EtOAc
[10]Methoxyethylamine (1.5 eq) was used at 120° C. for 3 hours
[11]Residue was purified on an 8 g silica Biotage cartridge eluting 40% EtOAc/isohexane
[12]Residue was purified using 0–50% EtOAc/isohexane as eluent
[13]Starting Material: Example 80
[14]After chromatography the residue was recrystallized from MeOH

EXAMPLE 77

(R)-N-[2-Chloro-3-phenoxy-4-(ethylsulphonyl)phenyl]-2-hydroxy-2-methyl-3,3,3-trifluoropropanamide (R)-N-[2-Chloro-3-fluoro-4-(ethylsulphonyl)phenyl]-2-hydroxy-2-methyl-3,3,3-trifluoropropanamide (Example 15; 0.308 g) was added to a stirred suspension of phenol (0.150 g) and anhydrous potassium carbonate (0.220 g) in anhydrous DMF (2 ml). The reaction mixture was heated to 150° C. under argon for 17 hours and allowed to cool to ambient temperature. EtOAc (50 ml) was added and the organic phase was washed with brine (4×50 ml), separated, dried and volatile material was removed by evaporation. The residue was purified on a 8 g silica Biotage cartridge eluting 40% EtOAc/isohexane to give the title compound (0.073 g) as a pale yellow foam. NMR (CDCl$_3$): 1.18 (t, 3H), 1.69 (s, 3H), 3.23–3.30 (q, 2H), 3.48 (s, 1H), 6.78 (d, 2H), 7.02 (t, 1H), 7.24 (t, 2H), 7.97 (d, 1), 8.50 (d, 1H), 9.24 (brs, 1H); m/z: 450.

EXAMPLE 78

(R)-N-[2-Chloro-3-methoxy-4-(ethylsulphonyl)phenyl]-2-hydroxy-2-methyl-3,3,3-trifluoropropanamide The title compound was prepared from 2-chloro-3-methoxy-4-ethylsulphonylaniline (Method 10) according to the procedure described in Method 11 in 19% yield as a white solid. NMR (CDCl$_3$): 1.15 (t, 3H), 1.71 (s, 3H), 3.27–3.34 (q, 2H), 3.57 (s, 1H), 3.98 (s, 3H), 7.81 (d, 1H), 8.36 (d, 1H), 9.24 (s, 1H); m/z: 388.

EXAMPLE 79

(R)-N-[2-Chloro-3-methylsulphanyl-4-(isopropylsulphonyl)phenyl]-2-hydroxy-2-methyl-3,3,3-trifluoropropanamide Sodium methane thiolate (0.309 g) was added to a stirred solution of (2R)-N-[2-chloro-3-fluoro-4-(isopropysulphonyl)phenyl]-2-hydroxy-2-methyl-3,3,3-trifluoropropanamide (Example 80; 0.862 g) in 1-methyl-2-pyrrolidinone (3 ml). The reaction mixture was heated to 128° C. for 20 hours. The reaction mixture was allowed to cool, EtOAc (100 ml) was added, and the mixture was washed with water (2×50 ml), brine (50 ml) and dried. Volatile material was removed by evaporation to leave an oil. This was dissolved in ether (100 ml) and washed with brine (50 ml). Volatile material was removed by evaporation to leave a foam that was recrystallized from EtOAc/hexane to give the title compound (0.495g) as a solid. NMR: 1.20 (m, 6H), 1.60 (s, 3H), 2.46 (s, 3H), 4.14 (m, 1H), 8.00 (d, 1H), 8.39 (d, 1H); m/z 418.

EXAMPLE 80

(2R)-N-[2-Chloro-3-fluoro-4-(isopropylsulphonyl)phenyl]-2-hydroxy-2-methyl-3,3,3-trifluoropropanamide Hydrogen peroxide (100 vols., 20 ml) was added to a solution of (2R)-N-[2-chloro-3-fluoro-4-(isopropylsulphanyl)phenyl]-2-hydroxy-2-methyl-3,3,3-trifluoropropanamide (Method 80; 1.21 g) in glacial acetic acid (20 ml) and the mixture was stirred for 4.5 hours at 100° C. It was allowed to cool to ambient temperature and volatile material was removed by evaporation. The residue was dissolved in EtOAc (100 ml) washed with water (50 ml), brine (50 ml), dried and volatile material was removed by evaporation to give the title compound (1.196 g) as a solid. NMR: 1.20 (d, 6H), 1.60 (s, 3H), 3.50 (m, 1H), 7.83 (t, 1H), 8.10 (s, 1H), 8.19 (d, 1H), 9.99 (s, 1H); m/z 390.

EXAMPLE 81

(R)-N-{2-Chloro-3-methylsulphanyl-4-[4-(N,N-dimethylcarbamoyl)phenylsulphonyl]phenyl}-2-hydroxy-2-methyl-3,3,3-trifluoropropanamide A mixture of (R)-N-{2-Chloro-3-fluoro-4-[4-(N,N-dimethylcarbamoyl)phenylsulphonyl]phenyl}-2-hydroxy-2-methyl-3,3,3-trifluoropropanamide (Example 18; 300 mg, 0.6 mmol), sodium methane thiolate(135 mg) in DMA (5 ml) was stirred overnight at 100° C. The mixture was allowed to cool to room temp and partitioned between EtOAc/water. The organic layers were washed with water and dried by pouring down a Chem Elut column and eluting with EtOAc. On standing 110 mg of colourless needle like crystals of the title compound were formed and filtered off and washed with hexane. NMR: 1.6 (s, 3H), 1.9 (s, 3H), 2.8 (s, 3H), 3.0 (s, 3H), 7.6 (d, 2H), 7.9 (d, 2H), 8.3 (d, 1H), 8.5 (d, 1H); m/z 523.

EXAMPLE 82

(R)-N-{2-Chloro-3-methylsulphanyl-4-[4-(N-methyl-N-ethylcarbamoyl)phenyl-sulphonyl]phenyl}-2-hydroxy-2-methyl-3,3,3-trifluoropropanamide (R)-N-{2-Chloro-3-fluoro-4-[4-(N-methyl-N-ethylcarbamoyl)phenylsulphonyl]phenyl}-2-hydroxy-2-methyl-3,3,3-trifluoropropanamide (Example 83; 290 mg, 0.57 mmol) was reacted with sodium methane thiolate (1.5 mmol) according to the procedure of Example 81. The residue was purified by chromatography on a Mega Bond Elut column eluting with 10–100% EtOAc/hexane to yield the title compound (220 mg) as a white solid. NMR: 1.1 (m, 3H), 1.6 (s, 3H), 1.9 (s, 3H), 2.9 (d, 3H), 3.1 (d, 1H), 3.5 (d, 1H), 7.6 (d, 2H), 7.9 (d, 2H), 8.1 (s, 1H), 8.4 (d, 1H), 8.5 (d, 1H), 9.9 (s, 1H); m/z 537.

EXAMPLE 83

(R)-N-{2-Chloro-3-fluoro-4-[4-(N-methyl-N-ethylcarbamoyl)phenylsulphonyl]phenyl}-2-hydroxy-2-methyl-3,3,3-trifluoropropanamide A mixture of (R)-N-{2-Chloro-3-fluoro-4-[4-(N-methyl-N-ethylcarbamoyl)phenylsulphanyl]phenyl}-2-hydroxy-2-methyl-3,3,3-trifluoropropanamide (Method 85; 370 mg, 0.77 mmol), glacial acetic acid (5 ml) and hydrogen peroxide (1.8 ml) was stirred at 95° C. for 3 hours and allowed to cool to room temp. The solution was extracted with EtOAc. The organic layers were washed with saturated sodium bicarbonate solution, water and brine and poured onto a Chem Elut column and eluted with EtOAc to yield the title compound (400 mg) as a white solid. NMR: 1.2 (m, 3H), 1.6 (s, 3H), 2.8 (d, 3H), 3.1 (d, 1H), 3.5 (d, 1H), 7.6 (d, 2H), 8.0 (d, 2H), 8.1 (t, 1H), 8.2 (d, 1H); m/z 509.

EXAMPLE 84

(R)-N-{2-Chloro-3-fluoro-4-[4-(N-ethylcarbamoyl)phenylsulphonyl]phenyl}-2-hydroxy-2-methyl-3,3,3-trifluoropropanamide (R)-N-{2-Chloro-3-fluoro-4-[4-(N-ethylcarbamoyl)phenylsulphanyl]phenyl}-2-hydroxy-2-methyl-3,3,3-trifluoropropanamide (Method 86; 90 mg), glacial acetic acid (1.3 ml) and hydrogen peroxide solution (0.45 ml) was heated with stirring at 95° C. for 3 hours. The reaction mixture was allowed to cool to room temp, and extracted with EtOAc. The organic layers were washed with saturated sodium bicarbonate solution. The organic layer was separated and washed with water then dried by pouring onto a Chem Elut column and eluting with EtOAc. The resulting solution was evaporated to dryness and the residue was purified by chromatography on a Bond Elut column eluting with 20–70 % EtOAc/hexane to give the title compound (80 mg) as a white solid. NMR: 1.1 (t, 3H), 1.6 (s, 3H), 3.2 (m, 2H), 8.1 (m, 6H), 8.7 (s, 1H), 9.9 (s, 1H); m/z 495.

Preparation of Starting Materials

The starting materials for the Examples above are either commercially available or are readily prepared by standard methods from known materials. For example the following reactions are illustrations but not limitations of the preparation of some of the starting materials used in the above reactions.

Method 1

(R)-N-(2,3-Dichloro-4-ethylsulphanylphenyl)-2-hydroxy-2-methyl-3,3,3-trifluoropropanamide Oxalyl chloride (0.75 ml) was added to a stirred suspension of (R)-(+)-2-hydroxy-2-methyl-3,3,3-trifluoropropanoic acid (Method 25) (1.37 g) in DCM (10 ml) containing DMF (1 drop). The mixture was stirred at ambient temperature for 18 hours and was then added to a solution of 4-ethylsulphanyl-2,3-dichloroaniline (Method 7) (1.92 g) and 2,6-diphenylpyridine (2.0 g) in DCM (50 ml). The mixture was stirred for 3 hours at room temperature, volatile material was removed by evaporation and the residue was purified by chromatography eluting with 0–20% EtOAc/isohexane to give the title compound (2.12 g) as a solid. NMR (CDCl$_3$) 1.35 (t, 3H), 1.76 (s, 3H), 2.97 (q, 2H), 3.61 (s, 1H), 7.22 (d, 1H), 8.27 (d, 1H), 8.91 (s, 1H); m/z: 360.

Methods 2–5

Following the procedure of Method 1 except that 2,6-di-t-butylpyridine was used in place of 2,6-diphenylpyridine and using the appropriate starting materials the following compounds were made.

| Meth | Compound | NMR | m/z | SM |
|---|---|---|---|---|
| 2 | (R)-N-(2-Chloro-3-fluoro-4-{4-fluorophenylsulphanyl}phenyl)-2-hydroxy-2-methyl-3,3,3-trifluoropropanamide | | 410 | Meth 19 |
| 3 | (R)-N-[3-Nitro-2-chlorophenyl]-2-hydroxy-2-methyl-3,3,3-trifluoropropanamide | (CDCl$_3$) 1.77 (s, 3H), 3.58 (s, 1H), 7.44 (t, 1H), 7.63 (d, 1H), 8.66 (d, 1H), 9.27 (s, 1H) | 311 | Meth 8 |
| 4 | (R)-N-[4-Iodo-2,3-dichlorophenyl]-2-hydroxy-2-methyl-3,3,3-trifluoropropanamide | 1.6 (s, 3H), 7.7 (d, 1H), 7.8 (s, 1H), 8.0 (d, 1H), 9.8 (s, 1H) | 426 | Meth 49 |
| 5 | (R)-N-[2-Chloro-3-fluoro-4-{4-(N,N-dimethylcarbamoyl)phenylsulphanyl}phenyl]-2-hydroxy-2-methyl-3,3,3-trifluoropropanamide | 1.55 (s, 3H), 2.85 (s, 3H), 2.95 (s, 3H), 7.25 (d, 2H); 7.35 (d, 2H), 7.55 (dd, 1H), 7.90 (d, 2H), 9.85 (s, 1H) | 463 | Meth 21 |

Method 6

2,3-Dichloro-4-ethylsulphanylbenzoic Acid

A chilled solution of sodium hypochlorite (120 ml of a solution with 4% available chlorine) was added to a solution of 4-ethylsulphanyl-2,3-dichloroacetophenone (10.0 g, prepared as described in European Patent Application EP 0 195 247) in dioxane (80 ml). The reaction mixture was allowed to stir at ambient temperature for 15 minutes and then slowly heated to 80° C. over 30 minutes and heating was maintained at this temperature for 1 hour. The reaction mixture was allowed to cool to room temperature and aqueous hydrochloric acid (100 ml of a 2M solution) was added and the resultant solid was collected and dried. This solid was redissolved in DCM (200 ml) and MeOH (20 ml), washed with sodium hydroxide (10% w/v, 300 ml) and the aqueous phase was separated and acidified with aqueous hydrochloric acid (2M, 300 ml). The precipitate was collected and dried to give the title compound (5.4 g) as a solid. NMR: 1.28 (t, 3H), 3.05 (q, 2H), 7.36 (d, 1H), 7.68 (d, 1H); m/z: 249.

Method 7

2,3-Dichloro-4-ethylsulphanylaniline

A stirred suspension of 2,3-dichloro-4-ethylsulphanylbenzoic acid (Method 6) (2.71 g) in t-butanol (70 ml) and triethylamine (1.6 ml) was heated to 60° C. Diphenylphosphoryl azide (2.5 ml) was added dropwise and the mixture was heated to 90° C. for 4 hours. The reaction mixture was allowed to cool to room temperature and the solvent was evaporated under reduced pressure. EtOAc (150 ml) was added and the organic phase was washed with saturated aqueous sodium hydrogen carbonate solution (2×100 ml) then dried. Volatile material was removed by evaporation to leave a 1:1 mixture of 2,3-dichloro-4-ethylsulphanylaniline and the t-butylurethane (2.51 g). TFA (6 ml) was added dropwise to this material and the mixture was stirred at ambient temperature for 30 minutes. Sodium hydroxide (20% w/v) was added to adjust the pH to 10–11 and the mixture was extracted with EtOAc (4×250 ml). The extracts were dried, volatile material was removed by evaporation, and the residue was purified by chromatography eluting with 10–50% EtOAc/isohexane to give the title compound (1.9 g) as an oil. NMR (CDCl$_3$): 1.26 (t, 3H), 2.85 (q, 2H), 4.2 (s, 2H), 6.65 (d, 1H), 7.21 (d, 1H); m/z: 220.

Methods 8–10

Following the procedure of Method 7 and using the appropriate starting materials the following compounds were made.

| Meth | Compound | NMR | m/z | SM |
|---|---|---|---|---|
| 8 | 2-Chloro-3-nitroaniline | (CDCl$_3$) 4.41 (brs, 2H), 6.92–6.97 (m, 1H), 7.15–7.19 (m, 2H) | 171 | 2-chloro-3-nitrobenzoicacid |
| 9 | 2-Chloro-4-ethylsulphonyl-3-hydroxyaniline | 1.06 (t, 3H), 3.24 (q, 2H), 6.24 (s, 2H), 6.39 (d, 1H), 7.29 (d, 1H), 10.1 (s, 1H) | 234 | 2-chloro-4-ethylsulphonyl-3-hydroxybenzoic acid (EP 0 195 247) |
| 10 | 2-Chloro-3-methoxy-4-ethylsulphonyl-aniline | 1.02 (t, 3H), 3.19–3.29 (q, 2H), 3.87 (s, 3H), 6.44 (brs, 2H), 6.66 (d, 1H), 7.38 (d, 1H) | 248 | 2-chloro-3-methoxy-4-ethyl-sulphonylbenzoic acid (EP 0 195 247) |

Method 11

(R)-N-(3-Acetamido-2-Chloro-4-{4-fluorophenylsulphanyl}phenyl)-2-hydroxy-2-methyl-3,3,3-trifluoropropanamide A solution of (S)-3,3,3-trifluoro-2-(trimethylsilyloxy)-2-methylpropanoyl chloride (prepared from (R)-3,3,3-trifluoro-2-hydroxy-2-methylpropionic acid (Method 25) as described in *J. Med. Chem.*, 1999, 42, 2741–2746) (1.179 g)

in DCM (10 ml) was added dropwise to a stirred and ice-cooled suspension of 3-acetamido-2-chloro-4-(4-fluorophenylsulphanyl)aniline (Method 18) (1.315 g) in DCM (20 ml) and triethylamine (1.72 ml). The mixture was allowed to warm to ambient temperature overnight. More triethylamine (0.8 ml) followed by (S)-3,3,3-trifluoro-2-(trimethylsilyloxy)-2-methylpropanoyl chloride (0.6 g) in DCM (5 ml) was added. After a further 6 hours the mixture was concentrated by evaporation. MeOH (50 ml) and 2M aqueous HCl (5 ml) were added, the mixture was stirred overnight, and then diluted with water (20 ml). The MeOH was removed by evaporation and 2M aqueous HCl (30 ml) was added. The mixture was then extracted with ether (2×80 ml). The extracts were washed with brine then dried. Volatile material was removed by evaporation and the residue was purified by chromatography on a Biotage cartridge (40 g silica), eluting with 50% EtOAc/isohexane to give the title compound (1.104 g) as a foam. NMR: 1.6 (s, 3H), 2.05 (s, 3H), 7.0 (d, 1H), 7.26 (t, 2H), 7.38–7.48 (m, 2H), 7.8–7.9 (m, 2H), 9.76 (brs, 1H), 9.9 (brs, 1H); m/z: 449.

Methods 12–14

Following the procedure of Method 11 and using the appropriate starting materials the following compounds were made.

| Meth | Compound | NMR | m/z | SM |
| --- | --- | --- | --- | --- |
| 12 | (R)-N-(4-Methylsulphanyl-3-fluoro-2-chlorophenyl)-2-hydroxy-2-methyl-3,3,3-trifluoropropanamide | (CDCl$_3$) 1.76 (s, 3H), 2.47 (s, 3H), 3.59 (s, 1H), 7.21 (d, 1H), 8.15 (dd, 1H), 8.89 (brs, 1H) | 330 | Meth 20 |
| 13 | (R)-N-(4-Thiocyanato-3-chloro-2-fluorophenyl)-2-hydroxy-2-methyl-3,3,3-trifluoropropanamide | 1.4 (s, 3H), 7.40–7.55 (m, 3H), 9.5 (s, 1 H) | 341 | Meth 41 |
| 14 | (R)-N-{2,3-Difluoro-4-[4-(N,N-dimethylcarbamoyl)phenylsulphanyl]phenyl}-2-hydroxy-2-methyl-3,3,3-trifluoropropanamide | 1.55 (s, 3H), 2.70–2.85 (m, 6H), 7.20–7.35 (m, 4H), 7.50 (td, 1H), 7.75 (d, 1H), 9.90 (s, 1H) | 447 | Meth 38 |

Method 15

3-Acetamido-2-chloro-4-(4-fluorophenylsulphanyl) nitrobenzene

4-Fluorobenzenethiol (0.128 ml) was added dropwise to a stirred suspension of sodium hydride (0.049 g of a 60% dispersion in mineral oil) in THF (3 ml). The mixture was stirred for 30 minutes then added dropwise to a stirred and cooled (−65° C.) solution of 3-acetamido-2-amino-4-fluoronitrobenzene (0.233 g) in THF (2 ml). The mixture was stirred for 3 hours at −65° C. then allowed to warm to ambient temperature. Saturated aqueous ammonium chloride solution (5 ml), then water (5 ml) were added and the mixture was extracted with ether (2×25 ml). The extracts were combined, washed with water (25 ml) and brine (25 ml), then dried. Volatile material was removed by evaporation and the residue was purified on a silica gel Mega Bond Elut column eluting with 0–40% EtOAc/isohexane to give the title compound. Chromatography on a Biotage cartridge (40 g silica), eluting with 40% EtOAc/isohexane to give the title compound (0.193 g) as a solid. NMR: 2.14 (s, 3H), 6.76 (d, 1H), 7.4 (t, 2H), 7.6 (m, 2H), 7.88 (d, 1H), 10.1 (brs, 1H); m/z: 339.

Methods 16–17

Following the procedure of Method 15 and using 2-amino-3,4-difluoronitro-benzene and the appropriate starting materials the following compounds were made.

| Meth | Compound | NMR | m/z |
| --- | --- | --- | --- |
| 16 | 2-Amino-3-fluoro-4-(4-fluorophenylsulphanyl) nitrobenzene | 5.98 (dd, 1H), 7.32–7.47 (m, 4H), 7.6–7.68 (m, 2H), 7.76 (d, 1H) | 282 (M$^+$) |
| 17 | 2-Fluoro-3-(4-carboxyphenylsulphanyl)-6-nitroaniline | 6.00 (dd, 1H), 7.35 (s, 2H); 7.45 (d, 2H), 7.75 (d, 1H), 7.95 (d, 2H) | 307 |

Method 18

3-Acetamido-2-chloro-4-(4-fluorophenylsulphanyl) aniline

A mixture of 3-acetamido-2-chloro-4-(4-fluorophenylsulphanyl)nitrobenzene (Method 15) (0.1 g), ferric chloride hexahydrate (0.238 g) and zinc dust (0.192 g in DMF (1 ml) and water (1 ml) was stirred and heated (oil bath 100° C.) for 1 hour then cooled. Water (15 ml) was added and the mixture was basified to pH 11 with saturated aqueous sodium carbonate solution (3 ml) then extracted with DCM (3×15 ml). The extracts were washed with brine then dried. Volatile material was removed by evaporation and the residue was left under high vacuum (2 mm Hg) overnight to give the title compound (0.087 g) as a solid. NMR: 1.95 (s, 3H), 5.72 (brs, 2H), 6.73 (d, 1H), 7.05–7.20 (m, 5H), 9.54 (brs, 1H); m/z: 309.

Methods 19–21

Following the procedure of Method 18 and using the appropriate starting materials the following compounds were made.

| Meth | Compound | NMR | m/z | SM |
| --- | --- | --- | --- | --- |
| 19 | 2-Chloro-3-fluoro-4-(4-fluorophenylsulphanyl)aniline | 6.15 (brs, 2H), 6.67 (d, 1H), 7.15 (d, 4H), 7.22 (t, 1H) | 270 | Meth 22 |
| 20 | 3-Fluoro-4-methylsulphanyl-2-chloroaniline | (CDCl$_3$) 2.37 (s, 3H), 4.19 (brs, 2H), 6.49 (d, 1H), 7.09–7.14 (m, 1H) | 191 (M$^+$) | Meth |
| 21 | 2-Chloro-3-fluoro-4-(4-N,N-dimethylcarbamoylphenylsulphanyl)aniline | 2.95 (d, 6H), 6.20 (s, 2H), 6.70 (d, 1H), 7.05 (d, 2H); 7.25 (d, 1H), 7.30 (d, 2H) | 323 | Meth 75 |

Method 22

2-Chloro-3-fluoro-4-(4-fluorophenylsulphanyl) nitrobenzene

2-Amino-3-fluoro-4-(4-fluorophenylsulphanyl) nitrobenzene (Method 16) (0.846 g) was added portionwise over 5 minutes to a stirred and heated (oil bath 65° C.) mixture of t-butylnitrite (0.59 ml) and cupric chloride (0.484 g) in acetonitrile (12 ml). Heating was continued for 1 hour then the mixture was left to cool and filtered. Ether (60 ml) was added and the mixture was washed with 20% aqueous hydrochloric acid (2×60 ml) then dried. Volatile material was removed by evaporation and the residue was purified by chromatography on a Biotage cartridge (40 g silica), eluting with 5% EtOAc/isohexane to give the title compound (0.574 g) as a solid. NMR: 6.96 (t, 1H), 7.41 (t, 2H), 7.7 (m, 2H), 7.91 (d, 1H); MS (EI): 302 (M+H)$^+$.

Methods 23–24

Following the procedure, of Method 22 and using the appropriate starting materials the following compounds were made.

| Meth | Compound | NMR | m/z | SM |
|---|---|---|---|---|
| 23 | 3-Fluoro-4-methylsulphanyl-2-chloronitrobenzene | (CDCl$_3$) 2.55 (s, 3H), 7.14–7.19 (m, 1H), 7.78 (d, 1H) | 221 (M$^+$) | Meth 26 |
| 24 | 2-Chloro-3-fluoro-4-(4-carboxyphenylsulphanyl)nitrobenzene | 7.35 (dd, 1H); 7.55 (d, 2H), 7.90–8.00 m, 3H) | 327 | Meth 17 |

Method 25

(R)-(+)-2-Hydroxy-2-methyl-3,3,3-trifluoropropanoic Acid

The title compound was resolved according to the resolution method described in European Patent Application No. EP 524781 (described for the preparation of the (S)-(−) acid) except that (1S, 2R)-norephedrine was used in place of (1R, 2S)-norephedrine or (S)-(−)-1-phenylethylamine. NMR analysis of the acid in the presence of (R)-(+)-1-phenylethylamine gave an enantiomerical purity of >98%; NMR (CDCl$_3$): 1.27 (s, 3H) for the (R)-enantiomer, 1.21 (s, 3H) for the (S)-enantiomer.

Method 26

2-Fluoro-3-methylsulphanyl-6-nitroaniline

To a stirred solution of 2,3-difluoro-6-nitroaniline (13.3 g) in DMF (250 ml) under argon was added sodium methane thiolate (5.7 g). The reaction mixture was allowed to stir at ambient temperature for 5 hours. EtOAc (500 ml) was added and the mixture was washed with brine (6×500 ml) and dried. Volatile material was removed by evaporation to give the title compound (14.9 g) as a yellow solid. NMR (CDCl$_3$): 2.51 (s, 3H), 6.09 (brs, 2H), 6.48–6.54 (m, 1H), 7.92 (d, 1H); m/z (EI+): 202 (M$^+$).

Method 27

(R)-N-[4-Ethylsulphanyl-3-fluoro-2-chlorophenyl]-2-hydroxy-2-methyl-3,3,3-trifluoropropanamide A suspension of (R)-N-[4-methylsulphinyl-3-fluoro-2-chlorophenyl]-2-hydroxy-2-methyl-3,3,3-trifluoropropanamide (Example 2) (5.41 g) in trifluoroacetic anhydride (65 ml) was heated under reflux for 30 minutes. The reaction mixture was evaporated and the residue was redissolved in MeOH (32 ml) and triethylamine (32 ml) and ethyl iodide (2.2 ml) was added. The reaction mixture was heated under reflux for 3 hours, allowed to cool to room temperature and volatile material was removed by evaporation. The residue was partitioned between EtOAc (150 ml) and brine (100 ml); the organic phase was separated, dried and volatile material was removed by evaporation. The residue was purified by flash column chromatography eluting with 10–20% EtOAc/isohexane to give the title compound (2.16 g) as a yellow solid. NMR (CDCl$_3$) 1.27 (s, 3H), 1.76 (s, 3H), 2.88–2.95 (q, 2H), 3.55 (s, 1H), 7.32 (t, 1H), 8.15 (d, 1H), 8.92 (s, 1H); m/z: 344.

Method 28

(R)-N-[4-Ethylsulphanyl-3-iodo-2-chlorophenyl]-2-hydroxy-2-methyl-3,3,3-trifluoropropanamide To a stirred solution of (R)-N-[4-mercapto-3-iodo-2-chlorophenyl]-2-hydroxy-2-methyl-3,3,3-trifluoropropanamide (Method 29) (5.85 g) in anhydrous THF (40 ml) under argon was added sodium methoxide (0.44 g) followed by ethyl iodide (0.65 ml) and the mixture was heated under reflux for 1 hour and allowed to cool to ambient temperature. EtOAc (200 ml) was added, the organic phase was washed with brine (100 ml) and dried. Volatile material was removed by evaporation and the residue was purified by flash column chromatography eluting with 5–30% EtOAc/isohexane to give the title compound (2.08 g) as a pale yellow solid. NMR (CDCl$_3$) 1.36 (t, 3H), 1.75 (s, 3H), 2.92–2.99 (q, 2H), 7.15 (d, 1H), 8.34 (d, 1H), 8.89 (s, 1H); m/z: 452.

Method 29

(R)-N-[4-Mercapto-3-iodo-2-chlorophenyl]-2-hydroxy-2-methyl-3,3,3-trifluoropropanamide To a stirred solution of triphenylphosphine (6.41 g) in DCM (35 ml) and DMF (0.30 ml) cooled to 0° C. was added a solution of (R)-N-[4-chlorosulphonyl-3-iodo-2-chlorophenyl]-2-hydroxy-2-methyl-3,3,3-trifluoropropanamide (Method 30) (4.0 g) in DCM (40 ml). The reaction mixture was allowed to stir at ambient temperature for 45 minutes, HCl (50 ml, 2M) was added and stirring was continued for 30 minutes. The organic phase was dried and volatile material was removed by evaporation. Ether (70 ml) was added and the suspension was filtered. The filtrate was evaporated to give the title compound (5.85 g) as a brown foam. M/z: 424.

Method 30

(R)-N-[4-Chlorosulphonyl-3-iodo-2-chlorophenyl]-2-hydroxy-2-methyl-3,3,3-trifluoropropanamide (R)-N-[3-Iodo-2-chlorophenyl]-2-hydroxy-2-methyl-3,3,3-trifluoropropanamide (Method 31) (4.92 g) was added in portions to chlorosulphonic acid (18 ml) at 0° C. The reaction mixture was heated to 80° C. for 4 hours, allowed to cool to ambient temperature and poured onto ice-water (200 g). The mixture was extracted into DCM (2×250 ml), the organic phase was washed with brine (300 ml) and dried. Volatile material was removed by evaporation to give the title compound (4.8 g) as a brown gum. NMR (CDCl$_3$) 1.78 (s, 3H), 3.59 (s, 1H), 8.23 (d, 1H), 8.74 (d, 1H), 9.53 (s, 1H); m/z: 490.

Method 31

(R)-N-[3-Iodo-2-chlorophenyl]-2-hydroxy-2-methyl-3,3,3-trifluoropropanamide

To a cooled solution of (R)-N-[3-amino-2-chlorophenyl]-2-hydroxy-2-methyl-3,3,3-trifluoropropanamide (Method 32) (12.5 g) in concentrated sulphuric acid (25 ml) and water (70 ml) was added a solution of sodium nitrite (3.15 g) in water (70 ml) dropwise. The reaction mixture was allowed to stir for 10 minutes and for 1 hour at ambient temperature. A solution of potassium iodide (22.2 g) in water (70 ml) was added cautiously and the mixture was heated to 100° C. for 2.5 hours. The reaction mixture was allowed to cool to ambient temperature, EtOAc (500 ml) was added and the organic phase was washed with brine (300 ml) and dried. Volatile material was removed by evaporation and the residue was purified by flash column chromatography eluting with 5–20% EtOAc/isohexane to give the title compound (13.5 g) as a cream solid. NMR (CDCl$_3$) 1.76 (s, 3H), 3.63 (s, 1H), 7.05 (t, 1H), 7.68 (d, 1H), 8.36 (d, 1H), 8.97 (brs, 1H); m/z: 392.

Method 32

(R)-N-[3-Amino-2-chlorophenyl]-2-hydroxy-2-methyl-3,3,3-trifluoropropanamide To a stirred solution of (R)-N-[3-nitro-2-chlorophenyl]-2-hydroxy-2-methyl-3,3,3-trifluoropropanamide (Method 3) (14.3 g) in EtOAc (250 ml) under a hydrogen atmosphere was added 10% palladium on carbon (1.6 g). The reaction mixture was allowed to stir at room temperature overnight; the mixture was filtered through a pad of diatomaceous earth and volatile material was removed by evaporation to give the title compound (13 g) as a brown solid. NMR (CDCl$_3$) 1.75 (s, 3H), 4.00 (s, 1H), 4.10 (brs, 2H), 6.61 (d, 1H), 7.08 (t, 1H), 7.72 (d, 1H), 8.77 (brs, 1H); m/z: 281.

Method 33

(R)-N-[4-Methylsulphanyl-2,3-dichlorophenyl]-2-hydroxy-2-methyl-3,3,3-trifluoropropanamide (R)-N-(4-Iodo-2,3-dichlorophenyl)-2-hydroxy-2-methyl-3,3,3-trifluoropropanamide (Method 4) (5.17 g, 12.08 mmol) was dissolved in DMA (30 ml) and heated at 155° C. for 6 hours stirring under argon with sodium methane thiolate (1.1 g, 1.3 eq), and cuprous chloride (670 mg). The reaction mixture was allowed to cool to room temperature and quenched with the addition of EtOAc and water. The reaction mixture was filtered through a bed of diatomaceous earth and washed thoroughly with EtOAc/water. The organic layer was washed with water followed by brine, then dried and evaporated to dryness. The residue was chromatographed on a Mega Bond Elut column eluting with 2–30% EtOAc/hexane and the resulting product was triturated with 10% Et$_2$O/Hexane to give the title compound as a cream solid (2.97 g). NMR: 1.6 (s, 3H), 2.5 (s, 3H), 7.3 (d, 1H), 7.8 (d, 1H); m/z: 346.

Method 34

(R)-N-[4-(2-Hydroxybutylsulphanyl)-2,3-dichlorophenyl]-2-hydroxy-2-methyl-3,3,3-trifluoropropanamide Sodium methoxide (0.075 g) was added to a stirred solution of (R)-N-[2,3-dichloro-4-mercaptophenyl]-2-hydroxy-2-methyl-3,3,3-trifluoropropanamide (Method 35) (0.44 g) in anhydrous THF (10 ml). The reaction mixture was stirred at ambient temperature for 5 minutes and 1,2-epoxybutane (0.11 ml) was added. The mixture was heated under reflux for 2 hours and allowed to cool to ambient temperature. EtOAc (150 ml) was added and the mixture washed with brine (100 ml) and dried. Volatile material was removed by evaporation and the residue was purified on a 20 g silica Mega Bond Elut column eluting with 1–40% EtOAc/isohexane to give the title compound (0.259 g) as an orange solid. NMR: 0.88 (t, 3H), 1.35–1.49 (m, 1H), 1.58 (s, 3H), 2.97–3.08 (m, 1H), 3.53–3.62 (m, 1H), 5.00 (d, 1H), 7.42 (d, 1H), 7.77 (d, 1H), 9.79 (brs, 1H); m/z: 404.

Method 35

(R)-N-[2,3-Dichloro-4-mercaptophenyl]-2-hydroxy-2-methyl-3,3,3-trifluoropropanamide Triisopropylsilane thiol (2.0 ml) was added to a stirred suspension of sodium hydride (0.37 g, 60% mineral oil dispersion) in anhydrous THF (30 ml) cooled to 0° C. under argon. After 20 minutes at this temperature the reaction mixture was added to a stirred suspension of (R)-N-[4-iodo-2,3-dichlorophenyl]-2-hydroxy-2-methyl-3,3,3-trifluoropropanamide (Method 4) (4.0 g) and tetrakis(triphenylphosphine)palladium(0) (0.86 g) in anhydrous toluene (40 ml). The mixture was heated to 85° C. for 5 hours and DMF (10 ml) was added to obtain a clear solution. Heating was continued for a further 17 hours. The mixture was allowed to cool to ambient temperature, EtOAc (200 ml) was added and the mixture washed with brine (3×100 ml) and dried. Volatile material was removed by evaporation and the residue was purified by flash chromatography eluting with 1–50% EtOAc/isohexane to give the title compound (0.448 g) as an orange solid. NMR: 1.58 (s, 3H), 7.55 (d, 1H), 7.66 (d, 1H), 7.73 (s, 1H), 9.80 (s, 1H); m/z: 332.

Method 36

(R)-N-[2,3-Dichloro-4-{4-(N,N-dimethylcarbamoyl)phenylsulphanyl}phenyl]-2-hydroxy-2-methyl-3,3,3-trifluoropropanamide (R)-N[2,3-Dichloro-4-thiocyanatophenyl]-2-hydroxy-2-methyl-3,3,3-trifluoropropanamide (Method 39) (0.5 g) as a solution in DMF was treated with a solution of sodium sulphide (403 mg) in water (2 ml) and the mixture was heated at 50° C. for 1 hour. The reaction mixture was then treated with a solution of N,N-dimethylcarbamoyl-4-iodobenzene (0.455 g) in DMF (5 ml), followed by cuprous oxide (0.121 g). The reaction mixture was heated at 150° C. for 4.5 hours under an argon atmosphere. The reaction mixture was quenched with water (100 ml), and DCM was added (100 ml) and the mixture was filtered through diatomaceous earth. The aqueous layer was separated and washed with DCM (3×50 ml). The organic extracts were combined and dried. The volatile material was removed by evaporation, and the product was purified by chromatography using a Mega Bond Elut column (20 g silica) eluting with 0–5% MeOH/DCM to yield the title compound as a white solid. (0.53 g) 80%. NMR: 1.60 (s, 3H), 2.95 (d, 6H), 7.30 (d, 1H); 7.30–7.50 (m, 4H), 7.85 (s, 1H), 7.90 (d, 1H), 9.90 (s, 1H); m/z: 479.

Methods 37–38

Following the procedure of Method 36 and using the appropriate starting materials the following compounds were made.

| Meth | Compound | NMR | m/z | SM |
|---|---|---|---|---|
| 37 | (R)-N-{2-Fluoro-3-Chloro-4-[4-(N,N-dimethylcarbamoyl)phenylsulphanyl]phenyl}-2-hydroxy-2-methyl-3,3,3-trifluoropropanamide | 1.6 (s, 3H), 2.8–3.0 (brd, 6H), 7.2 (d, 2H), 7.4 (dd, 2H), 7.6 (dd, 1H), 7.8 (d, 1H), 7.95 (s, 1H), 9.90 (s, 1H) | 463 | Meth 13 |

| Meth | Compound | NMR | m/z | SM |
|---|---|---|---|---|
| 38 | 2,3-Difluoro-4-[4-(N,N-dimethylcarbamoyl)phenyl-sulphanyl]phenylaniline | (CDCl$_3$) 2.90–3.15 (m, 6H), 4.05 (brs, 2H), 6.55 (td, 1H), 7.15 (d, 2H), 7.25 (d, 3H) | 309 (M + H)$^+$ | Meth 42 |

Method 39

(R)-N-[2,3-Dichloro-4-thiocyanatophenyl]-2-hydroxy-2-methyl-3,3,3-trifluoropropanamide (R)-(+)-2-Hydroxy-2-methyl-3,3,3-trifluoropropanoic acid (Method 25) (1 g), as a suspension in DCM was treated with anhydrous DMF (1 drop). Oxalyl chloride (1.15 ml) was added dropwise as a solution in DCM over a period of 15 minutes. The mixture was left to stir overnight under an argon atmosphere. The volatile material was removed by evaporation and the residue redissolved in DCM (20 ml). This solution was used to treat a solution of 2,3-dichloro-4-thiocyanatoaniline (Method 40) (1.37 g) and di-t-butylpyridine (1.55 ml) in DCM by addition over 15 minutes. The reaction was left to stir overnight at ambient temperature under an argon atmosphere. The volatile material was removed by evaporation and the residue purified by chromatography on a Mega Bond Elut column (20 g silica), to yield the title compound as a white solid, 1.08 g (48%). NMR (CDCl$_3$) 1.65 (s, 3H), 7.80 (d, 1H), 7.95 (s, 1H), 8.10 (d, 1H), 9.95 (s, 1H), 1.65 (s, 3H); m/z: 357.

Method 40

2,3-Dichloro-4-thiocyanatoaniline

To a cold (0–5° C.) solution of 2,3-dichloroaniline (2 g) and sodium thiocyanate (3 g) in MeOH (30 ml), was added a solution of bromine (2 g) in MeOH (10 ml) saturated with sodium bromide. The solution was left to stir for 1 hour. The reaction mixture was poured into water (200 ml) and neutralised with sodium carbonate to pH 8. The solid was collected by filtration and dried to yield the title compound as a white solid (2.38 g) 88%. NMR: 6.35 (s, 2H), 6.81 (d, 1H), 7.55 (d, 1H); m/z (EI+): 218.

Methods 41–42

Following the procedure of Method 40 and using the appropriate starting materials the following compounds were made.

| Meth | Compound | NMR | m/z (M$^+$) |
|---|---|---|---|
| 41 | 2-Fluoro-3-chloro-4-thiocyanato-aniline | 6.2 (s, 2H), 6.8 (dd, 1H), 7.4 (dd, 1H) | 202 |
| 42 | 2,3-Difluoro-4-thiocyanatoaniline | 6.00 (brs, 2H), 6.50 (td, 1H), 6.85 (td, 1H) | 186 |

Method 43

(R)-N-(2-Methyl-3-fluroro-4-[4-fluorophenyl]sulphanylphenyl)-2-hydroxy-2-methyl-3,3,3-trifluoropropanamide To a solution of (R)-N-(2-methyl-3-fluoro-4-iodophenyl)-2-hydroxy-2-methyl-3,3,3-trifluoropropanamide (Method 45) (782 mg) in DMF (6 ml), was added 4-fluorothiophenol (0.32 ml) and Cu$_2$O (143 mg). The mixture was heated under Argon to 150° C. for 4.5 hours. All volatile material was removed by evaporation and the residue was dissolved in EtOAc (100 ml). This was filtered through diatomaceous earth and all volatile material was removed by evaporation. The residue was purified by chromatography on a silica gel, eluting with 15% EtOAc in isohexane to give the title compound (544 mg) as a solid. NMR: 1.57 (s, 3H), 2.06 (s, 3H), 7.15 (t, 1H), 7.26 (m, 3H), 7.39 (m, 2H), 7.52 (brs, 1H), 9.78 (brs, 1H); m/z: 390.

Method 44

Following the procedure of Method 43 and using the appropriate starting materials the following compound was made.

| Meth | Compound | NMR | m/z | SM |
|---|---|---|---|---|
| 44 | (R)-N-(2-Methyl-3-chloro-4-[4-fluorophenyl]sulphanyl-phenyl)-2-hydroxy-2-methyl-3,3,3-trifluoropropanamide | 1.56 (s, 3H), 2.20 (s, 3H), 6.79 (d, 1H), 7.17 (d, 1H), 7.33 (t, 2H), 7.42 (brs, 1H), 7.52 (m, 2H), 9.85 (brs, 1H) | 406 | Meth 46 |

Method 45

(R)-N-(2-Methyl-3-fluoro-4-iodophenyl)-2-hydroxy-2-methyl-3,3,3-trifluoropropanamide Oxalyl chloride (0.7 ml) was added to a stiffed suspension of (R)-(+)-2-hydroxy-2-methyl-3,3,3-trifluoropropanoic acid (Method 25) (1.26 g) in DCM (40 ml) containing DMF (3 drops). The mixture was stirred at ambient temperature for 4 hours and 2,6-di-t-butylpyridine (2.25 ml) and 4-iodo-3-fluoro-2-methylaniline (Method 48) (1.368 g) were added. The resulting mixture was stirred at ambient temperature for 72 hours. Volatile material was removed by evaporation and the residue was purified by chromatography on a silica gel, eluting with 25% EtOAc/isohexane to give the title compound (1.668 g) as a solid. NMR: 1.56 (s, 3H), 2.08 (s, 3H), 7.03 (d, 1H), 7.66 (t, 1H); m/z: 390.

Methods 46–47

Following the procedure of Method 45 and using the appropriate starting materials the following compounds were made.

| Meth | Compound | NMR | m/z | SM |
|---|---|---|---|---|
| 46 | (R)-N-(2-Methyl-3-chloro-4-iodo-phenyl)-2-hydroxy-2-methyl-3,3,3-trifluoropropanamide | 1.59 (s, 3H), 2.28 (s, 3H), 7.04 (d, 1H), 7.45 (brs, 1H), 7.80 (d, 1H), 9.90 (brs, 1H) | 405 | Meth 50 |
| 47 | (R)-N-(2-Methyl-3-bromo-4-iodo-phenyl)-2-hydroxy-2-methyl-3,3,3-trifluoropropanamide | 1.58 (s, 3H), 2.32 (s, 3H), 7.06 (d, 1H), 7.44 (brs, 1H), 7.81 (d, 1H), 9.89 (brs, 1H) | 450 | Meth 51 |

Method 48

4-Iodo-3-fluoro-2-methylaniline

Iodine monochloride (0.5 ml) was added to a solution of 3-fluoro-2-methylaniline (1.25 g) in glacial acetic acid (15 ml). The mixture was stirred for two hours at 70° C. The mixture was allowed to cool to ambient temperature and saturated sodium sulphite solution (50 ml) was added. The solution was extracted with EtOAc (2×100 ml), and the extracts were combined, washed with saturated sodium bicarbonate solution (100 ml) and dried. The volatile material was removed by evaporation and the residue was purified by chromatography on silica gel, eluted with 0–10% EtOAc in hexane to give the title compound (1.53 g) as a solid. NMR: 1.98 (s, 3H), 5.32 (s, 2H), 6.30 (d, 1H), 7.20 (t, 1H); m/z: 250.

Methods 49–51

Following the procedure of Method 48 and using the appropriate starting materials the following compounds were made.

| Meth | Compound | NMR | m/z |
| --- | --- | --- | --- |
| 49[1] | 2,3-Dichloro-4-iodoaniline | 5.8 (s, 2H), 6.6 (d, 1H), 7.5 (d, 1H) | 286 |
| 50 | 4-Iodo-3-chloro-2-methyl-aniline | 2.18 (s, 3H), 5.31 (s, 2H), 6.20 (d, 1H), 7.34 (d, 1H) | 266 |
| 51 | 4-Iodo-3-bromo-2-methyl-aniline | 2.25 (s, 3H), 5.32 (s, 2H), 6.44 (d, 1H), 7.37 (d, 1H) | 311 (M+) |

[1]Chromatography solvent: 0–15% EtOAc/hexane. Gave a thick dark liquid which solidified when triturated with hexane.

Method 52

(R)-N-(2-Methyl-3-fluoro-4-[4-N,N-dimethylcarbamoylphenyl]sulphanylphenyl)-2-hydroxy-2-methyl-3,3,3-trifluoropropanamide 4-[N,N-Dimethylcarbamoyl]thiophenol (Method 53) (751 mg), (R)-N-(2-methyl-3-fluoro-4-iodo-phenyl)-2-hydroxy-2-methyl-3,3,3-trifluoropropanamide (Method 45) (1.433 g) and $Cu_2O$ (250 mg) were combined in DMF (10 ml). The mixture was stirred for 4.5 hours at 150° C. under Argon. The mixture was allowed to cool to ambient temperature, EtOAc (100 ml) was added and the resulting suspension was filtered through diatomaceous earth, before all volatile material was removed by evaporation. The residue was purified by chromatography eluting with 1–5% MeOH in DCM to give the title compound (1.02 g). NMR: 1.60 (s, 3H), 2.12 (s, 3H), 2.97 (brs, 6H), 7.20 (d, 2H), 7.37 (m, 4H), 9.81 (brs, 1H); m/z 443.

Method 53

4-[N,N-Dimethylcarbamoyl]thiophenol

Di-Phosphorous pentoxide (923 mg) was added to a solution of 4-mercaptobenzoic acid (2000 mg) in DMF (10 ml). The mixture was stirred for sixteen hours at 150° C. under argon. The mixture was allowed to cool then EtOAc (150 ml) was added. The solution was washed with water (100 ml), brine (50 ml) and dried. The volatile material was removed by evaporation and the residue was purified by chromatography on silica gel, eluted with 2.5% MeOH in DCM to give two samples. One sample containing a mixture of thiol and disulphide was purified by chromatography on silica gel, eluted with 1–2.5% MeOH in DCM to give the title compound (760 mg) as a solid. NMR: 2.94 (s, 6H), 5.63 (s, 1H), 7.30 (m, 4H); m/z 180.

Method 54

(R)-N-[4-(2-Hydroxyethylsulphanyl)-2,3-dichlorolphenyl]-2-hydroxy-2-methyl-3,3,3-trifluoropropanamide (R)-N-[4-Iodo-2,3-dichlorophenyl]-2-hydroxy-2-methyl-3,3,3-trifluoropropanamide (Method 4) (1.22 g) was added to a deoxygenated solution of 2-mercaptoethanol (0.26 ml), sodium methoxide (0.20 g) and copper (I) chloride (0.11 g) in quinoline (3 ml) and pyridine (1 ml). The mixture was heated to 190° C. under argon for 18 hours. The mixture was allowed to cool to room temperature EtOAc (200 ml) was added. The mixture was washed with hydrochloric acid (10% v/v, 2×250 ml), brine (200 ml) and dried. Volatile material was removed by evaporation and the residue was purified by chromatography on a 50 g silica gel Mega Bond Elut column eluting with 5–50% EtOAc/isohexane to give the title compound as an orange solid. NMR: 1.59 (s, 3H), 3.15 (t, 2H), 3.60–3.66 (m, 2H), 4.98 (t, 1H), 7.43 (d, 1H), 7.80 (d, 1H), 9.78 (brs, 1H); m/z: 376.

Method 59

(R)-N-[4-Ethylsulphonyl-3-(4-carboxyphenylsulphanyl)-2-chlorophenyl]-2-hydroxy-2-methyl-3,3,3-trifluoropropanamide Following the procedure of Example 48 using 4-mercaptobenzoic acid (1.5 eq) and sodium methoxide instead of sodium methane thiolate, the title compound was produced in 77% yield as a brown foam. NMR: 1.13 (t, 3H), 1.61 (s, 3H), 3.49–3.56 (q, 2H), 7.15 (d, 2H), 8.20 (d, 1H), 8.56 (d, 1H), 9.99 (brs, 1H), 12.9 (brs, 1H); m/z: 510.

Methods 60–62

Following the procedure of Example 9 and using the appropriate starting materials the following compounds were prepared:

| Meth | Compound | NMR | m/z | SM |
| --- | --- | --- | --- | --- |
| 60 | (R)-N-(2-Methyl-3-chloro-4-[4-carboxyphenylsulphonyl]phenyl)-2-hydroxy-2-methyl-3,3,3-trifluoropropanamide | 1.56 (s, 3H), 2.17 (s, 3H), 7.73 (d, 1H), 7.90 (d, 2H), 8.10 (d, 2H), 8.20 (d, 1H), 10.10 (brs, 1H) | 464 | Meth 63 |
| 61 | (R)-N-(2-Methyl-3-bromo-4-[4-carboxyphenylsulphonyl]phenyl)-2-hydroxy-2-methyl-3,3,3-trifluoropropanamide | 1.57 (s, 3H), 2.24 (s, 3H), 7.63 (brs, 1H), 7.76 (d, 1H), 7.96 (d, 2H), 8.10 (d, 2H), 8.26 (d, 1H), 10.08 (s, 1H) | 510 | Meth 64 |
| 62 | (R)-N-(2-Chloro-3-nitro-4-[4-carboxyphenylsulphonyl]phenyl)-2-hydroxy-2-methyl-3,3,3-trifluoropropanamide | 1.59 (s, 3H), 8.00 (d, 2H), 8.15 (d, 2H), 8.34 (d, 1H), 8.45 (d, 1H) | 495 | Meth 65 |

Method 63

(R)-N-(2-Methyl-3-chloro-4-[4-carboxyphenylsulphanyl]phenyl)-2-hydroxy-2-methyl-3,3,3-trifluoropropanamide 4-Mercaptobenzoic acid (308 mg) was added to a suspension of Copper(I) oxide (93 mg) and (R)-N-(2-methyl-3-chloro-4-iodo-phenyl)-2-hydroxy-2-methyl-3,3,3-trifluoropropanamide (Method 46) (530 mg) in DMF (5 ml). The mixture was heated under Argon to 150° C. for 4.5 hours. The mixture was allowed to cool to ambient temperature and EtOAc (100 ml) was added and the resulting suspension was filtered through diatomaceous earth, and volatile material was removed by evaporation. The residue was purified by chromatography, eluting with 5–10% MeOH in DCM to give the title compound (504 mg). NMR: 1.58 (s, 3H), 2.26 (s, 3H), 7.34 (m, 4H), 7.51 (brs, 1H), 7.92 (brs, 2H), 9.94 (s, 1H), 13.00 (brs, 1H); m/z 432.

Methods 64–65

Following the procedure of Method 63 and using the appropriate starting materials the following compounds were prepared:

| Meth | Compound | NMR | m/z | SM |
|---|---|---|---|---|
| 64 | (R)-N-(2-Methyl-3-bromo-4-[4-carboxyphenylsulphanyl)]phenyl)-2-hydroxy-2-methyl-3,3,3-trifluoropropanamide | 1.56 (s, 3H), 2.28 (s, 3H), 7.24–7.36 (m, 4H), 7.45 (brs, 1H), 7.91 (m, 2H), 9.91 (brs, 1H), 12.92 (brs, 1H) | 476 | Meth 47 |
| 65 | (R)-N-(2-Chloro-3-nitro-4-[4-carboxyphenylsulphanyl]phenyl)-2-hydroxy-2-methyl-3,3,3-trifluoropropanamide | 1.60 (s, 3H), 7.31 (d, 2H), 7.70 (d, 1H), 7.89 (d, 2H), 8.10 (d, 1H) | 463 | Meth 68 |

Method 66

(R)-N-[4-(4-Carboxyphenylsulphonyl)-2,3-dichlorophenyl]-2-hydroxy-2-methyl-3,3,3-trifluoropropanamide (R)-N-[4-(4-Carboxyphenylsulphanyl)-2,3,dichlorophenyl]-2-hydroxy-2-methyl-3,3,3-trifluoropropanamide (Method 67) (3.83 g, 8.45 mmol) was suspended with stirring in glacial acetic acid (55 ml). Hydrogen peroxide (19 ml) was added. The mixture was heated with stirring to 95° C. for 3 hours and allowed to cool to room temp. The mixture was evaporated to dryness to yield a cream solid which was triturated with hexane. The solid was filtered and washed to yield the title compound (3.97 g) as a cream solid. NMR: 1.6 (s, 3H), 8.0 (d, 2H), 8.1 (d, 2H), 8.4 (q, 2H), 9.9 (s, 1H); m/z: 484.

Method 67

(R)-N-[4-(4-Carboxyphenylsulphanyl)-2,3-dichlorophenyl]-2-hydroxy-2-methyl-3,3,3-trifluoropropanamide (R)-N-[4-Iodo-2,3-dichlorophenyl]-2-hydroxy-2-methyl-3,3,3-trifluoropropanamide (Method 4) (4.58 g, 10.7 mmol) was heated in DMF (30 ml) with stirring under argon for 4 hours with 4-mercaptobenzoic acid (2.31 g, 14.98 mmol) and cuprous oxide (765 mg) and allowed to cool to room temp. EtOAc and water were added, and the reaction mixture was filtered through a bed of diatomaceous earth, and washed with EtOAc/water. The organic layer was separated, washed with water, brine, dried and evaporated down to dryness. The resulting solid was purified using a Mega Bond Elut column, eluting with 5–50% EtOAc/isohexane to give the title compound (4.0 g) as a pale pink solid. NMR: 1.6 (s, 3H), 7.3 (d, 2H), 7.5 (d, 1H), 7.9 (m, 3H), 8.0 (d, 1H), 9.9 (s, 1H), 13.0 (s, 1H); m/z: 452.

Method 68

(R)-N-(2-Chloro-3-nitro-4-iodophenyl)-2-hydroxy-2-methyl-3,3,3-trifluoropropanamide 2M Hydrochloric acid (2.5 ml) was added to a solution of (R)-N-(2-chloro-3-nitro-4-iodophenyl)-2-trimethylsilyloxy-2-methyl-3,3,3-trifluoropropanamide (Method 69) (1150 mg) in MeOH (25 ml) and the reaction mixture was stirred for 4 hours at ambient temperature. The volatile material was removed by evaporation and the residue was partitioned between EtOAc (150 ml) and water (75 ml). The organic phase was separated, washed with brine (75 ml) and dried. The volatile material was removed by evaporation to give the title compound (943 mg). NMR: 1.58 (s, 3H), 7.70 (d, 1H), 8.00 (d, 1H); m/z 437.

Method 69

(R)-N-(2-Chloro-3-nitro-4-iodophenyl)-2-trimethylsilyloxy-2-methyl-3,3,3-trifluoropropanamide 4-Iodo-3-nitro-2-chloroaniline (Method 70) (1269 mg) and 2,6-di-t-butylpyridine (1.5 ml) were added to a solution of (S)-3,3,3-trifluoro-2-(trimethylsilyloxy)-2-methylpropanoyl chloride (prepared from (R)-3,3,3-trifluoro-2-hydroxy-2-methylpropionic acid (Method 25) as described in J. Med. Chem., 1999, 42, 2741–2746) (6 mmol) in DCM (40 ml). The mixture was stirred for 3 days at ambient temperature. The volatile material was removed by evaporation and the residue was purified by chromatography eluting with 10% EtOAc in hexane to give the title compound (1160 mg). NMR: 0.27 (s, 9H), 1.70 (s, 3H), 7.70 (d, 1H), 8.05 (d, 1H), 9.72 (brs, 1H); m/z 509.

Method 70

4-Iodo-3-nitro-2-chloroaniline

Iodine monochloride (1.25 ml) was added to a solution of 3-nitro-2-chloroaniline (4265 mg) in glacial acetic acid (40 ml). The mixture was stirred for four hours at 70° C. After the mixture was allowed to cool to ambient temperature, saturated sodium sulphite solution (100 ml) was added. The solution was extracted with EtOAc (200 ml), volatile material was removed by evaporation and the residue was redissolved in EtOAc (150 ml), washed with saturated sodium bicarbonate solution (75 ml), brine (75 ml) and dried. The volatile material was removed by evaporation and the residue was purified by chromatography eluting with 5–15% EtOAc in hexane to give a mixture of the title compound and the starting material (1.933 g) (ratio 1:1.75). Iodine monochloride (0.28 ml) was added to a solution of the mixture (1919 mg) in glacial acetic acid (10 ml). The mixture was stirred for four hours at 70° C. After the mixture was allowed to cool to ambient temperature, saturated sodium sulphite solution (50 ml) added. The solution was extracted with EtOAc (100 ml), volatile material was removed by evaporation and the residue was partitioned between EtOAc (100 ml) and saturated sodium bicarbonate solution (50 ml). The organic phase was separated, washed with brine (50 ml) and dried. The volatile material was removed by evaporation and the residue was purified by chromatography eluting with 5–15% EtOAc in hexane to give the title compound (1286 mg) as a solid. NMR: 6.19 (s, 2H), 6.73 (d, 1H), 7.50 (d, 1H); m/z 297.

Method 71

(R)-N-[4-{2-Nitropyrid-6-ylsulphonyl}-2,3-dichlorophenyl]-2-hydroxy-2-methyl-3,3,3-trifluoropropanamide A mixture of (R)-N-[2,3-Dichloro-4-(chlorosulphonyl)phenyl]-2-hydroxy-2-methyl-5 3,3,3-trifluoropropanamide (2 g, 5 mmol) (Method 73), sodium sulphite (1.25 g) and sodium hydrogen carbonate (1.05 g) in water (10 ml) was stirred at 75° C. for 1 hour. The solution was evaporated to dryness giving a white solid. To this was added 2-chloro-6-nitropyridine (Method 72; 713 mg) and DMF (15 ml). The mixture was heated with stirring at 75° C. for 4 hrs then allowed to cool to room temperature. The residue was partitioned between water and EtOAc. The aqueous layer was extracted with EtOAc, the organic layers were combined, washed with brine, dried and volatiles removed by evaporation. Purification was achieved with a Mega Bond Elut column and graduated solvent 0–40% EtOAc/hexane. This yielded the title compound (250 mg) as a pale yellow foam. NMR: 1.6 (s, 3H), 8.1 (s, 1H), 8.4 (q, 2H), 8.6 (d, 1H), 8.9 (d, 1H), 9.4 (s, 1H); m/z: 486.

Method 72

2-Chloro-6-nitropyridine

Copper (II) chloride (5.8 g) and t-butylnitrite (6.1 ml) were stirred in THF (150 ml) under argon and heated to 65° C. 2-Amino-6-nitropyridine (Shurko, O. P., Mamaev, V. P., Chem Heterocycl Comp, 26, 1990,1 47–52; 5 g, 36 mmol) was added portionwise. The reaction was stirred at 65° C. for 1 hour then allowed to cool to room temperature. EtOAc (200 ml) was added and the organic layer was washed with 2M HCl, water and dried. Volatile material was removed by evaporation to give a sticky orange solid which was triturated with hexane to give the title compound (3.4 g) as a brown/orange solid. NMR: 7.8 (d, 1H), 8.6 (d, 1H), 9.2 (s, 1H).

Method 73

(R)-N-[2,3-Dichloro-4-(chlorosulphonyl)phenyl]-2-hydroxy-2-methyl-3,3,3-trifluoropropanamide (R)-N-{2,3-Dichlorophenyl)-2-hydroxy-2-methyl-3,3,3-trifluoropropanamide (Method 74) (5.0 g, 16.6 mmol) was added in portions to cooled (0° C.) chlorosulphonic acid (5.3 ml, 81 mmol) over 15 mins and then the mixture was heated to 85° C. for 4.5 hours. The reaction mixture was cooled in an ice bath and then poured slowly onto a stirred ice-water mixture (60 ml). The mixture was extracted with DCM (2×75 ml), the DCM washed with brine, dried and evaporated. The residue was chromatographed on silica with 20% EtOAc in hexane as eluent to give the title compound as a solid (3.0 g, 7.5 mmol). NMR (CDCl$_3$): 1.8 (s, 3H), 3.4 (s, 1H), 8.15 (d, 1H), 8.65 (d, 1H) and 9.55 (brs, 1H); m/z 400.

Method 74

(R)-N-{2,3-Dichlorophenyl}-2-hydroxy-2-methyl-3,3,3-trifluoropropanamide

To a stirred solution of 2,3-dichloroaniline (6.85 g, 42.5 mmol) and pyridine (5.1 ml, 75 mmol) in DCM (100 ml) was added a solution of S-3,3,3-trifluoro-2-trimethylsilyoxy-2-methylpropanoyl chloride (prepared from (R)-3,3,3-trifluoro-2-hydroxy-2-methylpropionic acid (Method 25) as described in *J. Med. Chem.*, 1999, 42, 2741–2746) (12.2 g, 150 mmol) in DCM (50 ml). The mixture was stirred at ambient temperature for 24 hours, then washed with 1M hydrochloric acid, saturated sodium hydrogen carbonate solution and brine, then dried and evaporated. The residue was dissolved in MeOH (50 ml), treated with 1M hydrochloric acid (25 ml) and the mixture stirred at ambient temperature for 18 hours. The MeOH was evaporated, the aqueous layer extracted with EtOAc (2×25 ml), the EtOAc extracts were washed with saturated sodium hydrogen carbonate solution and brine, then dried and evaporated. The residue was chromatographed on silica with DCM as eluent to give the title compound as a solid (5.2 g, 17.3 mmol). NMR: 1.6 (s, 3H), 7.4 (dd, 1H), 7.5 (d, 1H), 7.8 (s, 1H), 7.9 (d, 1H), 9.8 (s, 1H); m/z 300.

Method 75

2-Chloro-3-fluoro-4-(4-N,N-dimethylcarbamoylphenylsulphanyl)nitrobenzene

The title compound was prepared from 2-chloro-3-fluoro-4-(4-carboxyphenyl-sulphanyl)nitrobenzene (Method 24) by the procedure of Example 51. NMR: 2.95 (d, 6H), 7.20 (dd, 1H); 7.50 (d, 2H), 7.60 (d, 2H), 7.95 (d, 1H); m/z (ES$^+$): 355 (M+H)$^+$.

Method 76

(R)-N-{2-Chloro-3-(4-carboxyphenylsulphanyl)-4-[4-(N,N-dimethylcarbamoyl)phenylsulphonyl]phenyl}-2-hydroxy-2-methyl-3,3,3-trifluoropropanamide (R)-N-{2-Chloro-3-fluoro-4-[4-(N,N-dimethylcarbamoyl)phenylsulphonyl]phenyl}-2-hydroxy-2-methyl-3,3,3-trifluoropropanamide (Example 18) was treated with 4-mercaptobenzoic acid according to the procedure of Example 50 to yield the title compound as a white solid.(0.39 g, 25%). NMR: 1.60 (s, 3H), 2.90 (s, 3H), 3.00 (s, 3H), 7.55–7.65 (m, 4H); 7.90–7.95 (m, 4H), 8.05 (s, 1H), 8.55 (d, 1H), 8.65 (d, 1H), 9.95 (s, 1H); 10.60 (s, 1H); m/z: 629.

Method 77

2-Fluoro-3-(isopropylsulphanyl)-6-nitroaniline

Sodium 2-propanethiolate (5.66 g) was added to a solution of 2,3-difluoro-6-nitroaniline (10.04 g) in DMF (200 ml). The mixture was stirred at ambient temperature for 16 hours and then diluted with EtOAc (300 ml) and washed with brine (500 ml). The washing was extracted with EtOAc (300 ml). The organic phases were combined, washed with brine (500 ml), dried and volatile material was removed by evaporation to give the title compound (14.1 g) as a solid. NMR: 1.30 (d, 6H), 3.70 (septet, 1H), 6.70 (dd, 1H), 7.26 (s, 2H), 7.80 (dd, 1H); m/z 229.

Method 78

2-Chloro-3-fluoro-4-(isopropylsulphanyl)-nitrobenzene

A solution of 2-fluoro-3-(isopropylsulphanyl)-6-nitroaniline (Method 77; 14.0 g) in acetonitrile (100 ml) was added to a stirred mixture of copper (II) chloride (8.95 g) and t-butylnitrite (9.9 ml) in acetonitrile (300 ml) at 65° C. under argon and the mixture was stirred for 2.5 hours. The reaction mixture was allowed to cool, EtOAc (300 ml) was added, and the mixture was washed with 2M hydrochloric acid (2×200 ml), brine (200 ml) and dried. The volatile material was removed by evaporation to leave an oil. This was purified by chromatography on silica gel, eluted with 10–25% EtOAc in hexane to give the title compound (10.16 g). NMR: 1.33 (d, 6H), 3.78 (m, 1H), 7.65 (t, 1H), 7.98 (d, 1H); m/z 249 (M$^+$).

Method 79

2-Chloro-3-fluoro-4-(isopropylsulphanyl)aniline

A solution of iron trichloride hexahydrate (32.7 g) in water (100 ml) was added to a mixture of 2-chloro-3-fluoro- 4-(isopropylsulphanyl)nitrobenzene (Method 78; 10.07 g) and zinc dust (26.36 g) in DMF (100 ml). The mixture was heated to 100° C. for two hours and then allowed to cool to ambient temperature. It was then diluted with EtOAc (500 ml) filtered through diatomaceous earth, washed with brine (4×250 ml), dried over magnesium sulphate and volatile material was removed by evaporation to leave an oil. This was purified by chromatography on silica gel, eluted with 10% EtOAc in hexane to give the title compound (5.29 g) as a solid. NMR: 1.11 (d, 6H), 3.10 (septet, 1H), 5.92 (s, 2H), 6.57 (d, 1H), 7.11 (t, 1H); m/z 219 ($M^+$).

Method 80

(2R)-N-[2-Chloro-3-fluoro-4-(isopropylsulphanyl) phenyl]-2-hydroxy-2-methyl-3,3,3-trifluoropropanamide 1,3-Bis(trimethylsilyl)urea (5.73 g) was added to a solution of (R)-(+)-2-hydroxy-2-methyl-3,3,3-trifluoropropanoic acid (Method 25; 4.424 g) in DCM (75 ml) and the mixture was stirred for 16 hours at ambient temperature. A solid was filtered off and washed with DCM (20 ml). The organic solutions were combined, cooled in an ice bath, and oxalyl chloride (2.7 ml) and DMF (cat) were added. The solution was then warmed to ambient temperature and stirred for 24 hours. Volatile material was removed by evaporation, the residue was dissolved in DCM (50 ml) and added to an ice bath cooled mixture of 2-chloro-3-fluoro-4-(isopropylsulphanyl)aniline (Method 79; 5.105 g) and triethylamine (11.7 ml) in DCM (50 ml). The mixture was allowed to warm to ambient temperature and stirred for 18 hours. Volatile material was removed by evaporation to leave an oil. This was purified by chromatography on silica gel, eluted with 10%–25% EtOAc in hexane to give a solid. This was dissolved in anhydrous THF (15 ml) and cooled to −78° C. 1M tetrabutylammonium fluoride (3.6 ml) was added and the mixture was stirred for 45 minutes at −78° C. under Argon. It was then allowed to warm to ambient temperature and stirred for a further 30 minutes. 2M Hydrochloric acid (50 ml) was added and the mixture extracted with EtOAc (100 ml). The extract was washed with brine (50 ml), dried, and the volatile material was removed by evaporation to leave the title compound (1.23 g) as a solid. NMR: 1.21 (d, 6H), 1.58 (s, 3H), 3.45 (m, 1H), 7.50 (t, 1H), 7.79 (d, 1H), 7.84 (s, 1H), 9.79 (s, 1H); m/z 358.35.

Method 81

2-Chloro-3-fluoro-4-[4-(N-methyl-N-ethylcarbamoyl)phenylsulphanyl]nitrobenzene

2-Chloro-3-fluoro-4-(4-carboxyphenylsulphanyl) nitrobenzene (Method 24; 5.5 g, 16.8 mmol) was suspended with stirring in DCM (100 ml) and oxalyl chloride (3.22 ml) was added. A couple of drops of DMF were added to initiate the reaction and it was left to stir overnight. The mixture was evaporated to dryness and then redissolved in DCM (20 ml). N-ethyl-N-methylamine (0.46 ml, 5.28 mmol) was dissolved in DCM (1 ml) and to this with stirring was added some of the above acid chloride solution (2.4 mmol). The solution was left to stir overnight and then washed with water, brine and dried by pouring onto a Chem Elut column eluting with EtOAc. The resulting solution was evaporated down to dryness and then purified by chromatography on a Mega Bond Elut column eluting with a graduated solvent of hexane/EtOAc to yield the title compound (680 mg). NMR: 1.1 (s, 3H), 2.9 (d, 3H), 3.2 (s, 1H), 3.4 (s, 1H), 7.2 (m, 1H), 7.5 (d, 2H), 7.6 (d, 2H), 8.0 (m, 1H); m/z 369.

Method 82

2-Chloro-3-fluoro-4-[4-(N-ethylcarbamoyl) phenylsulphanyl]nitrobenzene

Ethylamine solution (2M in absolute EtOH; 2.65 ml) was placed in a reaction vessel with DCM (1 ml). To this was added a portion of the acid chloride solution (2.4 mmol) as prepared in Method 81. The solution was left to stir overnight and then washed with water, brine and dried by pouring onto a Chem Elut column eluting with EtOAc. The solution was evaporated to dryness and purified by chromatography on a Mega Bond Elut column eluting with graduated solvent hexane/EtOAc to give the title compound (380 mg). NMR: 1.1 (t, 3H), 3.2 (m, 2H), 7.1 (t, 1H), 7.6 (d, 2H), 7.9 (m, 2H), 8.6 (s, 1H).

Method 83

2-Chloro-3-fluoro-4-[4-(N-methyl-N-ethylcarbamoyl)phenylsulphanyl]aniline

2-Chloro-3-fluoro-4-[4-(N-methyl-N-ethylcarbamoyl) phenylsulphanyl]nitrobenzene (Method 81; 650 mg. 1.76 mmol) was heated with stirring at 75° C. for 45 minutes with of iron powder (1.06 g), EtOH (1.2 ml), water (0.5 ml) and 2 drops of conc. HCl. The mixture was then allowed to cool to room temp, made basic with saturated sodium bicarbonate solution, and EtOAc was added. The reaction mixture was filtered through a bed of diatomaceous earth, washing through thoroughly with water and EtOAc. The organic layers were combined and washed with water, dried, filtered and evaporated to dryness to give the title compound (600 mg) as a pale yellow gum. NMR: 1.0 (s, 3H), 2.8 (s, 3H), 3.2 (d, 2H), 6.2 (s, 1H), 7.0 (m, 2H), 7.2 (m, 3H).

Method 84

2-Chloro-3-fluoro-4-[4-(N-ethylcarbamoyl) phenylsulphanyl]aniline

2-Chloro-3-fluoro-4-[4-(N-ethylcarbamoyl) phenylsulphanyl]nitrobenzene (Method 82; 360 mg, 1.02 mmol), iron powder (617 mg), EtOH (0.68 ml), water (0.28 ml) and 1 drop of conc. HCl were heated at 75° C. with stirring for 45 minutes. The mixture was allowed to cool to room temp and then made basic using saturated sodium bicarbonate solution. EtOAc was added and the solution was poured onto a Chem Elut column and eluted with EtOAc to yield the title compound (260 mg) as a pale yellow sticky solid. NMR: 1.1 (t, 3H), 3.2 (q, 2H), 6.1 (s, 1H), 7.0 (q, 2H), 7.2 (q, 1H), 7.7 (t, 2H), 8.3 (d, 1H).

Method 85

(R)-N-{2-Chloro-3-fluoro-4-[4-(N-methyl-N-ethylcarbamoyl)phenylsulphanyl]phenyl}-2-hydroxy-2-methyl-3,3,3-trifluoropropanamide 2-Chloro3-fluoro-4-[4-(N-methyl-N-ethylcarbamoyl) phenylsulphanyl]aniline (Method 83; 580 mg, 1.7 mmol) was dissolved in DCM (6 ml) and pyridine (0.28 ml) was added. (S)-3,3,3-Trifluoro-2-(trimethylsilyloxy)-2-methylpropanoyl chloride (prepared from (R)-3,3,3-trifluoro-2-hydroxy-2-methylpropionic acid (Method 25) as described in *J. Med. Chem.*, 1999, 42, 2741–2746) (508 mg) was dissolved in DCM (1 ml) and added to the aniline. The solution was stirred for 4 hours and then washed with HCl (2 M) to remove excess pyridine. The organic layer was evaporated to dryness, dissolved in MeOH (17 ml) and HCl (2M, 1.7 ml) was added. The solution was left to stir overnight at room temp. The MeOH was removed and the residue was partitioned between water and EtOAc. The aqueous layer was extracted twice with EtOAc, the organic layers were combined, washed with water, brine and dried by pouring down a Chem Elut column and eluting with EtOAc. The resulting solution was evaporated to dryness and purified by chromatography on a Bond Elut column, eluting with 5–65% EtOAc/hexane to yield the title compound (390 mg) as a white solid. NMR: 1.0 (s, 3H), 1.6 (3, 3H), 2.8 (s, 3H), 3.2 (d, 2H), 7.2 (d, 2H), 7.3 (d, 2H), 7.6 (t, 1H), 7.9 (s, 1H), 9.9 (s, 1H); m/z 477.

Method 86

(R)-N-2-Chloro-3-fluoro-4-[4-(N-ethylcarbamoyl) phenylsulphanyl]phenyl}-2-hydroxy-2-methyl-3,3,3-trifluoropropanamide 2-Chloro-3-fluoro-4-[4-(N-ethylcarbamoyl) phenylsulphanyl]aniline (Method 84) was reacted with (S)-3,3,3-trifluoro-2-(trimethylsilyloxy)-2-methylpropanoyl chloride according to the procedure of Method 85 to yield the title compound as a yellow gum. M/z 463.

EXAMPLE 85

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |
| 1M Sodium hydroxide solution | 15.0% v/v |
| 0.1M Hydrochloric acid | (to adjust pH to 7.6) |
| Polyethylene glycol 400 | 4.5% w/v |
| Water for injection | to 100% |

| -continued | |
|---|---|
| (f): Injection II | 10 mg/ml |
| Compound X | 1.0% w/v |
| Sodium phosphate BP | 3.6% w/v |
| 0.1M Sodium hydroxide solution | 15.0% v/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of formula (I):

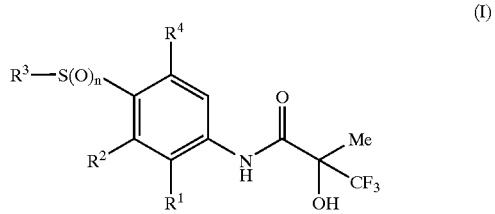

wherein:

n is 1 or 2;

$R^1$ is chloro, fluoro, bromo, methyl or methoxy;

$R^2$ is selected from one of the following three groups:
i) halo, nitro, hydroxy, amino or cyano;
ii) —$X^1$—$R^5$ wherein $X^1$ is a direct bond, —O—, —S—, —SO—, —$SO_2$—, $NR^6$, —CO, —$CONR^6$—, —$NR^6CO$—, —$NR^6SO_2$— or $NR^6CONR^7$—; wherein $R^6$ and $R^7$ are independently hydrogen or $C_{1-4}$alkyl optionally substituted with one or more A; and $R^5$ is selected from $C_{1-6}$alkyl optionally substituted with one or more A, $C_{3-7}$cycloalkyl optionally substituted with one or more A, $C_{3-7}$cycloalkyl$C_{1-6}$alkyl optionally substituted with one or more A, $C_{2-6}$alkenyl optionally substituted with one or more A, $C_{2-6}$alkynyl optionally substituted with one or more A, phenyl optionally substituted with one or more D, phenyl$C_{1-6}$allyl optionally substituted with one or more D, heteroaryl ring optionally substituted on a ring carbon by one or more D or (heteroaryl ring)$C_{1-6}$alkyl optionally substituted on a ring carbon with one or more D; wherein said heteroaryl ring is a carbon linked 6-membered ring containing 1–2 nitrogen atoms or a carbon linked 5-membered ring containing 1–3 heteroatoms selected independently from O, N and S; and wherein if said 5-membered heteroaryl ring contains an —NH— moiety that nitrogen may be optionally substituted with a group selected from G;
iii) a nitrogen-linked 4–8 membered heterocyclic group optionally substituted on a ring carbon by one or more D and wherein if said heterocyclic group contains an —NH— moiety that nitrogen may be optionally substituted with a group selected from G;

$R^3$ is $C_{1-6}$alkyl optionally substituted with one or more A, $C_{3-7}$cycloalkyl optionally substituted with one or more A, phenyl optionally substituted with one or more D, a carbon-linked 6-membered heteroaryl ring containing 1–2 nitrogen atoms optionally substituted on a ring carbon by one or more D, or a carbon linked 5-membered heteroaryl ring containing 1–3 heteroatoms selected independently from O, N and S optionally substituted on a ring carbon by one or more D and wherein if said 5-membered heteroaryl ring contains an —NH— moiety that nitrogen may be optionally substituted with a group selected from G;

A is selected from hydroxy, amino, halo, carboxy, N—($C_{1-4}$alkyl)amino, N,N-di-($C_{1-4}$alkyl)amino, carbamoyl and $C_{1-6}$alkoxy;

D is selected from:
  i) —$X^a$—$R^c$ wherein $X^a$ is a direct bond, —O—, —S—, —SO—, —SO$_2$—, —CO—, —NR$^d$SO$_2$—, —NR$^d$CO—, NR$^d$CONR$^e$—, —NR$^d$— or —CONR$^d$—; wherein $R^d$ and $R^e$ are independently hydrogen or $C_{1-4}$alkyl optionally substituted with one or more hydroxy or $C_{1-4}$alkoxy; and $R^c$ is selected from hydrogen or $C_{1-6}$alkyl optionally substituted with one or more hydroxy or $C_{1-4}$alkoxy;
  ii) a 4–8 membered Het which is optionally substituted on a ring carbon with one or more groups selected from hydroxy, halo, $C_{1-4}$alkoxy, $C_{1-4}$alkyl or cyano and wherein if said 4–8 membered Het contains an —NH— moiety that nitrogen may be optionally substituted with a group selected from G;
  iii) —$X^a$—$C_{1-6}$alkyl-$X^b$—$R^c$ wherein $X^a$ and $R^c$ are as defined hereinbefore and $X^b$ is —S—, —SO— or —SO$_2$—;
  iv) cyano or halo; and
  v) —$X^c$—$R^f$ wherein $X^c$ is —C(O)— or —SO$_2$— and $R^f$ is a nitrogen-linked 4–8 membered heterocyclic group optionally substituted on a ring carbon by one or more groups selected from hydroxy, halo, $C_{1-4}$alkoxy, $C_{1-4}$alkyl or cyano and wherein if said heterocyclic group contains an —NH— moiety that nitrogen may be optionally substituted with a group selected from G;

G is selected from $C_{1-6}$alkyl optionally substituted with one or more A, $C_{1-6}$alkanoyl optionally substituted with one or more A, $C_{1-6}$alkylsulphonyl optionally substituted with one or more A, $C_{1-6}$alkoxycarbonyl optionally substituted with one or more A, carbamoyl, N—($C_{1-6}$alkyl)carbamoyl optionally substituted with one or more A, N—($C_{1-6}$alkyl)$_2$carbamoyl optionally substituted with one or more A and benzoyl optionally substituted with one or more A; and $R^4$ is hydrogen or fluoro;

or a pharmaceutically acceptable salt or an in vivo hydrolysable ester thereof.

2. A compound of formula (I) according to claim 1 wherein n is 2 or a pharmaceutically acceptable salt or an in vivo hydrolysable ester thereof.

3. A compound of formula (I) according to claim 1 wherein $R^1$ is methyl, chloro or fluoro or a pharmaceutically acceptable salt or an in vivo hydrolysable ester thereof.

4. A compound of formula (I) according to claim 1 wherein $R^2$ is chloro, fluoro, bromo, iodo, nitro, amino, methoxy, acetylamino, hydroxy, $C_{1-4}$alkylsulphanyl (optionally substituted with hydroxy), $C_{1-4}$alkylsulphinyl, $C_{1-4}$alkylsulphonyl, N—($C_{1-4}$alkyl)amino (optionally substituted with hydroxy, methoxy, dimethylamino or carbamoyl), morpholino, 4-acetylpiperazin-1-yl, thiomorpholino, 1-oxothiomorpholino, 1,1-dioxothiomorpholino, benzylamino, phenoxy, phenylsulphanyl (optionally substituted with N—($C_{1-4}$alkyl)$_2$ carbamoyl) or phenylsulphinyl (optionally substituted with N—($C_{1-4}$alkyl)$_2$carbamoyl) or a pharmaceutically acceptable salt or an in vivo hydrolysable ester thereof.

5. A compound of formula (I) according to claim 1 wherein $R^3$ is methyl, ethyl (optionally substituted with hydroxy), isopropyl, butyl (optionally substituted with hydroxy), phenyl or carbon-linked pyridyl or a pharmaceutically acceptable salt or an in vivo hydrolysable ester thereof.

6. A compound of formula (I) according to claim 1 wherein $R^4$ is hydrogen or a pharmaceutically acceptable salt or an in vivo hydrolysable ester thereof.

7. A compound of formula (I) selected from:

(R)-N-[2-Chloro-3-(1-oxothiomorpholino)-4-(ethylsulphonyl)phenyl]-2-hydroxy-2-methyl-3,3,3-trifluoropropanamide;

(R)-N-[2-Chloro-3-(1-oxothiomorpholino)-4-(isopropylsulphonyl)phenyl]-2-hydroxy-2-methyl-3,3,3-trifluoropropanamide;

(R)-N-[2-Chloro-3-(1,1-dioxothiomorpholino)-4-(methylsulphonyl)phenyl]-2-hydroxy-2-methyl-3,3,3-trifluoropropanamide;

(R)-N-[2-Chloro-3-(1,1-dioxothiomorpholino)-4-(ethylsulphonyl)phenyl]-2-hydroxy-2-methyl-3,3,3-trifluoropropanamide;

(R)-N-[2-Chloro-3-(1,1-dioxothiomorpholino)-4-(isopropylsulphonyl)phenyl]-2-hydroxy-2-methyl-3,3,3-trifluoropropanamide;

(R)-N-(2-Chloro-4-ethylsulphonyl-3-methylsulphanylphenyl)-2-hydroxy-2-methyl-3,3,3-trifluoropropanamide;

(R)-N-(4-Mesyl-3-methylsulphanyl-2-chlorophenyl)-2-hydroxy-2-methyl-3,3,3-trifluoropropanamide;

(R)-N-[2-Chloro-3-(4-acetylpiperazin-1-yl)-4-(ethylsulphonyl)phenyl]-2-hydroxy-2-methyl-3,3,3-trifluoropropanamide;

(R)-N-{2-Chloro-3-[1-(4-acetyl)piperazinyl]4-(methylsulphonyl)phenyl}-2-hydroxy-2-methyl-3,3,3-trifluoropropanamide;

(R)-N[2-Chloro-3-morpholino-4-(methylsulphonyl) phenyl]-2-hydroxy-2-methyl-3,3,3-trifluoropropanamide;

(R)-N-[2-Chloro-3-(4-acetylpiperazin-1-yl)-4-(isopropylsulphonyl)phenyl]-2-hydroxy-2-methyl-3,3,3-trifluoropropanamide; and (R)-N-[2-Chloro-3-morpholino-4-(isopropylsulphonyl) phenyl]-2-hydroxy-2-methyl-3,3,3-trifluoropropanamide;

or a pharmaceutically acceptable salt or an in vivo hydrolysable ester thereof.

8. A process for preparing a compound of formula (I) according to claim 1 or a pharmaceutically acceptable salt or an in vivo hydrolysable ester thereof, which process (in which variable groups are as defined for formula (I) unless otherwise stated) comprises of:

(a) deprotecting a protected compound of formula (II):

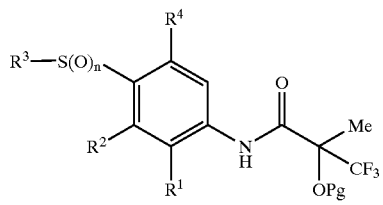

where Pg is an alcohol protecting group;

(b) oxidising a compound of formula (III):

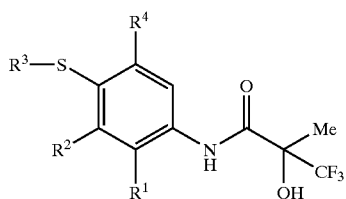

(c) coupling compounds of formula (IV):

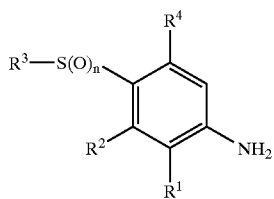

with an acid of formula (V):

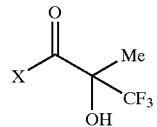

wherein X is OH;

(d) coupling an aniline of formula (IV) with an activated acid derivative of formula (V); and thereafter if necessary:
    i) converting a compound of the formula (I) into another compound of the formula (I);
    ii) removing any protecting groups; or
    iii) forming a pharmaceutically acceptable salt or in vivo hydrolysable ester.

9. A pharmaceutical composition which comprises a compound of formula (I) according to any one of claims 1–7, or a pharmaceutically acceptable salt or in vivo hydrolysable ester thereof in association with a pharmaceutically-acceptable diluent or carrier.

10. A compound of the formula (I) according to any one of claims 1–7, or a pharmaceutically acceptable salt or in vivo hydrolysable ester thereof for use in a method of treatment of the human or animal body by therapy.

11. A method for the treatment of a disease state associated with reduced PDH activity, said method comprising administering to a warm-blooded animal in need thereof a PDH activity-elevating amount of a compound of the formula (I) or a salt or in vivo hydrolysable ester thereof, as claimed in any one of claims 1–7.

12. The method of claim 11 wherein said disease state is selected from the group consisting of diabetes mellitus, peripheral vascular disease and myocardial ischaemia.

13. The method of claim 12 wherein said disease state is diabetes mellitus.

\* \* \* \* \*